United States Patent
Attenni et al.

(10) Patent No.: US 7,781,431 B2
(45) Date of Patent: Aug. 24, 2010

(54) THIENOPYRROLES AS ANTIVIRAL AGENTS

(75) Inventors: Barbara Attenni, Rome (IT); Jose Ignacio Martin Hernando, Pomezia (IT); Savina Malancona, Pomezia (IT); Frank Narjes, Ariccia (IT); Jesus Maria Ontoria Ontoria, Rome (IT); Michael Rowley, Axa (IT)

(73) Assignee: Istituto di Ricerche di Biologia Molecolare P Angeletti SpA, Pomezia, Rome (IT)

( * ) Notice: Subject to any disclaimer, the term of this patent is extended or adjusted under 35 U.S.C. 154(b) by 505 days.

(21) Appl. No.: 10/571,234

(22) PCT Filed: Sep. 7, 2004

(86) PCT No.: PCT/GB2004/003838

§ 371 (c)(1),
(2), (4) Date: Aug. 20, 2008

(87) PCT Pub. No.: WO2005/023819

PCT Pub. Date: Mar. 17, 2005

(65) Prior Publication Data
US 2009/0036443 A1    Feb. 5, 2009

(30) Foreign Application Priority Data
Sep. 9, 2003    (GB)    .................................... 0321003.6

(51) Int. Cl.
| C07D 411/06 | (2006.01) |
|---|---|
| C07D 413/06 | (2006.01) |
| C07D 413/14 | (2006.01) |
| C07D 409/12 | (2006.01) |
| C07D 409/06 | (2006.01) |
| C07D 417/04 | (2006.01) |
| C07D 417/12 | (2006.01) |
| C07D 417/06 | (2006.01) |
| C07D 409/04 | (2006.01) |
| C07D 333/78 | (2006.01) |
| A61K 31/5377 | (2006.01) |
| A61K 31/496 | (2006.01) |
| A61K 31/4436 | (2006.01) |
| A61K 31/4439 | (2006.01) |
| A61K 31/4535 | (2006.01) |
| A61K 31/454 | (2006.01) |
| A61K 31/4155 | (2006.01) |
| A61K 31/4178 | (2006.01) |
| A61K 31/4196 | (2006.01) |
| A61K 31/422 | (2006.01) |
| A61K 31/433 | (2006.01) |
| A61K 31/407 | (2006.01) |

(52) U.S. Cl. ............... 514/233.8; 514/412; 514/254.08; 514/321; 514/397; 514/393; 514/342; 514/340; 514/378; 514/414; 514/383; 514/376; 514/404; 514/361; 514/422; 514/374; 548/453; 548/266.6; 548/134; 548/364.4; 548/232; 548/302.7; 548/303.1; 544/143; 544/124; 544/121; 546/198; 546/276.7; 546/272.1

(58) Field of Classification Search .................. 548/453
See application file for complete search history.

(56) References Cited

U.S. PATENT DOCUMENTS

| 5,340,833 | A | * | 8/1994 | Bridges et al. ............... 514/443 |
| 6,992,092 | B2 | * | 1/2006 | Bussolotti et al. ............ 514/339 |
| 7,141,574 | B2 | * | 11/2006 | Beaulieu et al. .............. 514/256 |
| 2005/0272938 | A1 | * | 12/2005 | Butters et al. ................ 548/453 |

FOREIGN PATENT DOCUMENTS

| JP | 04-356029 A | 12/1992 |
|---|---|---|
| WO | WO 01/47883 A1 | 7/2001 |
| WO | WO 02/04425 A2 | 1/2002 |
| WO | WO 03/000254 A1 | 1/2003 |
| WO | WO 03/007945 A1 | 1/2003 |
| WO | WO 03/010140 A2 | 2/2003 |
| WO | WO 03/010141 A2 | 2/2003 |
| WO | WO 03/026587 A3 | 4/2003 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
P. Geetha et al., "Synthesis of Some Substituted 4H-Thieno[3,2-b]pyrroles," 17B Indian J. Chem. 163-64 (Feb. 1979).

(Continued)

*Primary Examiner*—Rebecca L Anderson
*Assistant Examiner*—Matthew P Coughlin
(74) *Attorney, Agent, or Firm*—Julie M. Lake; Sheldon O. Heber

(57) ABSTRACT

The present invention relates to thienopyrrole compounds of formula (I); wherein A, B, Y, Ar, n, Z and $X^1$ are as defined herein, and pharmaceutically acceptable salts thereof, useful in the prevention and treatment of hepatitis C infections.

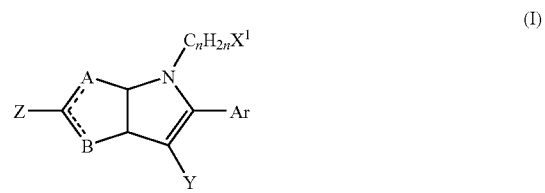

(I)

8 Claims, No Drawings

OTHER PUBLICATIONS

I. Ya. Kvitko et al., "Synthesis, structure, and comparative reactivity of heteroaromatic bicyclic systems of 1-methylthieno(selenopheno)[2,3-b]pyrrole, thieno(selenopheno)[2,3-b]furan, and thieno(selenopheno)[2,3-b]thiophene," 12(7) Zhurnal Organicheskoi Khimii 1574-85 (1976). (English-language abstract incl.).

V.I. Shvedov et al., "New method for synthesizing thieno[3,2-b]pyrrole derivatives," Kimiya Geterotsiklicheskikh Soedinenii (2) 276-77 (1970). (English-language abstract incl.).

English-language translation of: I. Ya. Kvitko & N.B. Sokolova, "Enamines of Formyl Derivatives of Thio- and Selenopyrrolone and Synthesis of Thieno- and Selenopheno[2,3-b]pyrroles," Khimiya Geterotsiklicheskikh Soedinenii (4) 565-66 (Apr. 1973).

English-language translation of: V.I. Shvedov et al., "Functional Derivatives of Thiophene XV. beta-Thienylhydrazine Derivatives in the Synthesis of Thieno[3,2-b]pyrroles," Khimiya Geterotsiklicheskikh Soedinenii (10) 1324-27 (Oct. 1975).

* cited by examiner

THIENOPYRROLES AS ANTIVIRAL AGENTS

This application is the National Stage of International Application No. PCT/GB2004/003838, filed on Sep. 7, 2004, which claims the benefit of United Kingdom Application No. 0321003.6, filed Sep. 9, 2003.

The present invention relates to thienopyrrole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit. International patent applications WO 01147883, WO 02/04425, WO 03/000254, WO 03/007945, WO 03/010140, WO 03/010141 and WO 03/026587 suggest fused ring compounds as possible inhibitors of HCV polymerase and illustrate thousands of possible benzimidazole and indole derivatives that possess HCV polymerase inhibitory properties. However, these patent applications do not describe or reasonably suggest the preparation of any thienopyrroles. Japanese Patent Publications 04356029 and 04179949 and Indian J. Chem. 1979, 17B, 163; J. Chem. Soc., Perkins trans. 1 1977, 2436 and Zhurnal Organichesko, 1976, 12, 1574 disclose various thienopyrroles but none are related to agents for the treatment of Hepatitis C.

The present invention provides compounds of the formula (I):

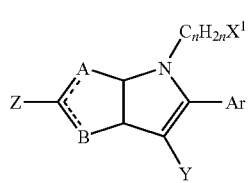

wherein:
one of A and B is S and the other C—$C_rH_{2r}X^2$ and the dotted line indicates a bond that commences at C—$C_rH_{2r}X^2$;

Y is a non-aromatic ring of 3 to 8 ring atoms which may contain a double bond and which may contain a O, S, SO, $SO_2$ or NH moiety and which may be optionally substituted by one or two alkyl groups of up to 2 carbon atoms or by 1 to 3 fluorine atoms;

Ar is a moiety containing at least one aromatic ring and possesses 5-, 6-, 8-, 9- or 10-ring atoms 0 to 4 of which atoms may be N, O or S heteroatoms of which at most 1 will be O or S and when N is present may be a N-oxide thereof; which moiety may be optionally substituted by groups $Q^1$, $Q^2$ or $Q^3$ wherein $Q^1$ is a hydroxy group; fluorine; chlorine; bromine or iodine atom; a $C_{1-6}$ alkyl; $C_{1-6}$ alkyl substituted by not more than 5 fluorine atoms or by $C_{4-10}$aryl; $C_{1-6}$ alkoxyl; $C_{1-6}$ alkoxyl substituted by not more than 5 fluorine atoms; $C_{2-6}$ alkenyl or alkynyl; nitro; nitrile; C(O)H, carboxyl; esterified carboxy wherein the esterifying moiety has up to 4 carbon atoms optionally substituted by not more than 5 fluorine atoms; $C_{4-10}$aryl; $OR^a$; $SR^a$; $(CH_2)_{0-4}NR^a{}_2$; $CONR^a{}_2$; $NR^bCOR^a$; $SO_2R^a$; $SO_2NR^a{}_2$ or $NR^bSO_2R^a$, where $R^a$ is $C_{1-6}$alkyl, $(CH_2)_{0-4}C_{4-10}$aryl or $(CH_2)_{0-4}NR^b{}_2$ and $R^b$ is hydrogen, $C_{1-6}$alkyl or $C_{4-10}$aryl, $Q^2$ is a fluorine; chlorine; bromine or iodine atom; methyl; trifluoromethyl; methoxy; trifluoromethoxy or difluoromethoxy group, $Q^3$ is a fluorine; chlorine; bromine or iodine atom; methyl, methoxy; trifluoromethoxy or difluoromethoxy group;

or Ar is $(CH_2)_{0-3}C_{3-8}$cycloalkyl, optionally substituted by hydroxy, halogen or $C_{1-6}$alkyl;

n is 0, 1, 2, 3, 4, 5 or 6;

t is 0, 1, 2, 3, 4, 5 or 6;

Z is $Het^1$ or is hydrogen; fluorine; chlorine or bromine atom; $C_{1-6}$ alkyl; $C_{2-6}$ alkenyl or alkynyl; $C_{1-6}$ alkoxy; $C_{1-6}$ alkyl or alkoxy substituted by up to 5 fluorine atoms; nitrile; carboxy; $C_{1-6}$ alkoxycarbonyl; $C_{1-6}$ alkyl or $C_{2-6}$ alkenyl substituted by a carboxy or $C_{1-6}$ alkoxycarbonyl group; $P(O)(OR^c)_2$ where $R^c$ is hydrogen or $C_{1-6}$alkyl; or a $SO_2NR^1R^2$, $CONR^1R^2$ or $CONR^{11}SO_2NR^{12}R^{13}$ group where $R^1$ is hydrogen, $C_{1-6}$ alkyl, $SO_2R^3$ or $COR^3$ and $R^2$ is hydrogen, hydroxyl or $C_{1-6}$, alkyl or $R^1$ and $R^2$ are alkylene linked to form a 5- or 6-membered ring, and $R^3$ is $C_{1-6}$ alkyl optionally substituted by up to 5 fluorine atoms or a group independently chosen from within the definitions of the $Ar^1$ group; $R^{11}$, $R^{12}$ and $R^{13}$ are each independently selected from hydrogen, $C_{1-6}$alkyl, $C_{2-6}$alkenyl, $(CH_2)_{0-3}$ $C_{3-8}$cycloalkyl, optionally substituted by hydroxy, carboxy or amino, or $R^{12}$, $R^{13}$ and the nitrogen atom to which they are attached form a heteroaliphatic ring of 4 to 7 ring atoms, which ring optionally contains 1, 2 or 3 additional heteroatoms selected from O or S or a group S(O), $S(O)_2$ or $NR^{14}$, where $R^{14}$ is hydrogen or $C_{1-6}$alkyl; $Het^1$ is a 5 or 6-membered aromatic ring 1, 2, 3 or 4 ring atoms of which may be selected from N, O, S heteroatoms of which at most 1 will be O or S; which ring may be substituted by 1 or 2 groups selected from $C_{1-6}$ alkyl or hydroxy or tautomers thereof, or is 2-hydroxy-cyclobutene-3,4-dione;

$X^1$ and $X^2$ are independently selected from $Het^2$; hydrogen; fluorine; chlorine; bromine or iodine atom; nitrile; hydroxyl; a group $Ar^1$; $C_{1-6}$alkyl; $C_{2-4}$alkenyl or alkynyl; $C_{1-6}$alkoxy; $C_{1-6}$alkyl or alkoxy substituted by up to 5 fluorine atoms or by $C_{1-4}$alkoxy or by hydroxy or by hydroxy and $NR^6R^7$; carboxy; $C_{1-6}$alkoxycarbonyl; $C_{2-6}$alkenyl substituted by a carboxy or $C_{1-6}$alkoxycarbonyl group; a —S—($C_{1-6}$alkyl); $SO_2NR^4R^5$; $CONR^4R^5$ or $NR^6R^7$ group;

$Het^2$ is a 3 to 8 membered non-aromatic ring which may contain a double bond and 1, 2, 3 or 4 of which ring atoms may be selected from N, O, S, SO or $SO_2$ moieties, which ring may be optionally substituted by 1, 2 or 3 groups selected from $Ar^1$, $A^1$, —$C_{1-6}$alkyl$Ar^1$, —$C_{1-6}$alkyl$A^1$, $S(O)_2C_{1-4}$alkyl, oxo or hydroxy or tautomers thereof;

$Ar^1$ is a moiety containing at least one aromatic ring and possesses 5-, 6-, 8-, 9- or 10-ring atoms 0 to 4 of which atoms may be N, O or S heteroatoms of which at most 1 will be O or S and when N is present may be a N-oxide thereof; which aromatic ring may be optionally substituted by groups $Q^{1'}$, $Q^{2'}$ or $Q^{3'}$ wherein $Q^{1'}$ is a hydroxy group or tautomers thereof; fluorine; chlorine; bromine or iodine atom; $C_{1-6}$ alkyl; $C_{1-6}$ alkyl substituted by not more than 5 fluorine atoms or by $C_{4-10}$aryl; $C_{1-6}$ alkoxyl; $C_{1-6}$ alkoxyl substituted by not more than 5 fluorine atoms; $C_{2-6}$ alkenyl or alkynyl; nitro; nitrile; carboxyl; esterified carboxy wherein the esterifying moiety has up to 4 carbon atoms optionally substituted by not more than 5 fluorine atoms; $C_{4-10}$aryl; $OR^a$; $SR^a$; $NR^a{}_2$; $CONR^a{}_2$; $NR^bCOR^a$; $SO_2R^a$; $SO_2NR^a{}_2$ or $NR^bSO_2R^a$, where $R^a$ is $C_{1-6}$alkyl or $C_{4-10}$aryl and $R^b$ is hydrogen, $C_{1-6}$alkyl or $C_{4-10}$aryl, $Q^{2'}$ is a fluorine; chlorine; bromine or iodine atom; a methyl, trifluoromethyl; methoxy; trifluoromethoxy or difluoromethoxy group, Q³' is a fluorine; chlorine; bromine or iodine atom; a methyl; methoxy; trifluoromethoxy or difluoromethoxy group;

A¹ is $C_{1-6}$alkyl; $C_{2-6}$alkenyl; $C_{1-6}$alkoxy; $C_{1-6}$alkyl or $C_{2-6}$alkenyl substituted by $C_{1-4}$alkoxy or up to 5 fluorine atoms; a non-aromatic ring of 3 to 8 ring atoms which may contain a double bond and which may contain 1, 2 or 3 from O, S, SO, $SO_2$ or NH moieties and which may be optionally substituted by one or two alkyl or alkoxy groups of up to 3 carbon atoms or by 1 to 3 fluorine or chlorine atoms or by 1 or 2 oxo groups, hydroxy groups or tautomers thereof;

$R^4$ and $R^5$ are independently hydrogen; a group $Ar^1$; $C_{1-6}$ alkyl; $C_{2-6}$ alkenyl; a $C_{1-6}$ alkyl or $C_{2-6}$ alkenyl group substituted by 1-3 fluorine atoms, a $OR^8$, $NR^8R^9$, $CO_2H$, $Ar^1$ or $A^1$ group; or $R^4$ and $R^5$ are joined to form a non-aromatic ring of 3 to 8 ring atoms which may contain a double bond and 1, 2 or 3 of which ring atoms may be selected from N, O, S, SO, or $SO_2$ moieties, which ring may be substituted by oxo; $Ar^1$; $A^1$; —$C_{1-6}$ alkyl $Ar^1$; —$C_{1-6}$ alkyl $A^1$; $(CH_2)_{0-3}N(C_{1-4}alkyl)_2$; or a further ring of 5-6 ring atoms 1, 2 or 3 of which may be selected from N, O, S which further ring may be substituted by $C_{1-6}$ alkyl substituted by 1-3 fluorine atoms, $OR^8$, $NR^8R^9$ or $CO_2H$ group; $R^8$ is hydrogen or $C_{1-6}$ alkyl, $R^9$ is hydrogen, $C_{1-6}$ alkyl optionally substituted by hydroxy, carboxy, amino, mono$C_{1-6}$ alkyl or di$C_{1-6}$ alkyl wherein the alkyl groups may be joined to form a 5- or 6-membered unsaturated ring which may contain a O, S, NH or $NCH_3$ group;

$R^6$ and $R^7$ are independently hydrogen; $C_{1-6}$alkyl; $C_{2-6}$alkenyl; $(CH_2)_{0-3}C_{3-8}$cycloalkyl; or a $C_{1-6}$alkyl or $C_{2-6}$alkenyl group substituted by 1-3 fluorine atoms, $OR^8$, $NR^8R^9$, $CO_2H$, $Ar^1$ or $A^1$; or a $COAr^1$ or $SO_2NR^8R^9$ or $(CO)_2NR^8R^9$ group;

or a pharmaceutically acceptable salt thereof.

The group $C_nH_{2n}$ or $C_tH_{2t}$ may be straight or branched such as a —$CH_2$—, —$(CH_2)_2$—, —$(CH_2)_3$—, —$(CH_2)_4$—, —$CH(CH_3)$—, —$CH_2$—$CH(CH_3)$—, —$CH(CH_3)$—$CH_2$— or the like straight or branched butyl, pentyl or hexyl group. Most suitably the $C_nH_{2n}$ or $C_tH_{2t}$ group is a —$CH_2$— group.

When used herein $C_{1-6}$alkyl means methyl, ethyl, 1-propyl, 2-propyl or a straight or branched butyl, pentyl or hexyl group. Particularly apt $C_{1-6}$ alkyl groups are methyl, ethyl, propyl and butyl groups. Favoured alkyl groups are ethyl, methyl and 2-propyl groups. The methyl group is the preferred alkyl group.

Most suitably a $C_{1-6}$ alkyl group substituted by up to 5 fluorine atoms will include a $CF_3$, $CHF_2$ and/or $CF_2$ moiety. Favoured fluoroalkyl groups are the $CF_3$, $CH_2F$ and $CF_2CF_3$ groups. The $CF_3$ group is the preferred fluoroalkyl group.

When used herein $C_{2-4}$ alkenyl means a —CH=$CH_2$, —C($CH_3$)=$CH_2$, —CH=C($CH_3$), —C($CH_3$)=C($CH_3$) or straight or branched pentenyl or hexenyl groups.

When used herein $C_{2-6}$alkynyl means a —C≡CH, —C≡$CCH_3$, —C≡$CCH_2CH_3$, —C≡$CCH_2CH_2CH_3$, —C≡$CCH(CH_3)_2$ or straight or branched hexynyl groups.

When used herein $C_{1-6}$ alkoxy and fluorinated $C_{1-6}$ alkoxy are analogous to the alkyl and fluoroalkyl groups described above so that, for example, preferred groups include $OCH_3$, $OCF_3$ and $OCHF_2$ groups.

When used herein $C_{4-10}$ aryl means phenyl or naphthyl. The phenyl group is the preferred aryl group.

In one embodiment A is C—$C_nH_{2n}X^2$ and B is S. In another embodiment A is S and B is C—$C_tH_{2t}X^2$.

The Ar or $Ar^1$ moiety may contain a single aromatic ring or one aromatic ring to which a further aromatic or non-aromatic ring is fused.

Ar is aptly phenyl, naphthyl, indolyl, tetrahydronaphthyl, pyridyl or N-oxides thereof, furyl, thienyl, pyrrolyl, oxazolyl, thiazolyl, pyrazolyl, pyridazolyl, triazolyl, imidazolyl, tetrazolyl, oxadiazolyl, thiodiazolyl or quinonyl, any of which may be optionally substituted by group $Q^1$, $Q^2$ or $Q^3$ as hereinbefore defined.

Alternatively, Ar is cyclopropyl, cyclobutyl, cyclopentyl or cyclohexyl, optionally substituted by hydroxy, halogen, methyl or ethyl.

Favourably, Ar is a phenyl, pyridyl, furyl, oxazolyl or thienyl group or a group of the formula $C_6H_2Q^1Q^2Q^3$. One particularly favoured Ar group is the phenyl group.

Other particularly favoured Ar groups are optionally substituted phenyl groups of the formula $C_6H_3Q^1Q^2$ of which phenyl, fluorophenyl, chlorophenyl, hydroxyphenyl, trifluoromethylphenyl, methoxyphenyl, difluorophenyl, methylphenyl, benzyloxyphenyl, formylphenyl, methoxychlorophenyl, dimethylaminomethylphenyl, dimethylaminoethoxyphenyl and the like are preferred. Preferably Ar is phenyl, fluorophenyl, or chlorophenyl of which chlorophenyl is particularly apt. Specific favoured Ar groups include phenyl, 3-fluorophenyl, 4-fluorophenyl, 4-chlorophenyl and pyrid-2-yl.

Particularly suitable groups Y include those groups of the formula:

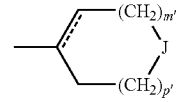

wherein m'+p' is 0, 1, 2, 3 or 4, preferably 1 or 2, the dotted line represents an optional bond and J is $CH_2$, O, S, SO, $SO_2$ or NH which group of the above formula may optionally be substituted by one or two methyl groups or fluorine atoms.

Favoured groups Y include cycloalkyl and cycloalkenyl groups of 5 or 6 ring members. Preferred groups Y include cyclopentyl and cyclohexyl groups. Cyclohexyl is a particularly preferred group.

Preferably, Z is $C(O)OR^{10}$ or $C(O)NR^{10}R^{11}$ where $R^{10}$ is hydrogen or $C_{1-6}$alkyl and $R^{11}$ is hydrogen, $C_{1-6}$alkyl or $S(O)_2 C_{1-6}$alkyl. More preferably, Z is $C(O)OH$, $C(O)OCH_3$, $C(O)NHCH_3$ or $C(O)NHS(O)_2CH_2CH_3$. Most preferably, Z is $CO_2H$.

Preferably n is 0, 1 or 2. More preferably, n is 1.

Preferably t is 0, 1 or 2. More preferably, t is 0 or 1.

Favoured values for $X^1$ include hydrogen, methoxy, $C_{1-6}$alkyl, $C_{1-6}$alkyl$C_{1-6}$alkoxy, carboxy, $C(OH)HCH_2NH(C_{1-6}alkyl)$; or (i) a moiety containing at least one aromatic ring and possesses 5-, 6-, 8-, 9- or 10-ring atoms up to 4 of which may be selected from O, N or S of which not more than one may be O or S and when N is present may be a N-oxide thereof; which ring may be substituted by $C_{1-6}$alkyl, $C_{4-10}$aryl, $C_{4-10}$aryl$C_{1-6}$alkyl, fluorine or chlorine; (ii) a non-aromatic ring of 3 to 8 ring atoms up to 4 of which may be selected from O, N or S and which ring may be substituted by one or more groups selected from $C_{1-6}$alkyl, $C_{2-6}$alkenyl, $C_{1-6}$alkoxy, oxo, hydroxy or tautomers thereof; (iii) $CONR^4R^5$; or (iv) $NR^6R^7$, wherein $R^4$, $R^5$, $R^6$ and $R^7$ are as hereinbefore defined.

Favoured values for 5 or 6 membered optionally substituted aromatic rings include phenyl, pyridyl or N-oxides thereof, furyl, thienyl, pyrrolyl, oxazolyl, isoxazolyl, thiazolyl, isothiazolyl, pyrazinyl, pyridazinyl, pyrazolyl, pyridazolyl, pyrimidinyl, triazolyl, tetrazolyl, oxadiazolyl, thiodiazolyl or imidazolyl. Particularly favoured groups include optionally substituted phenyl, imidazolyl, pyridyl or N-oxides thereof, triazolyl and oxazolyl.

Favoured 5 or 6 membered aromatic rings include phenyl, 3-fluorophenyl, 4-fluorophenyl, 4-chlorophenyl, imidazo-1-yl, 1-benzylimidazo-2-yl, pyrid-2-yl, pyrid-3-yl, pyrid-4-yl, N-oxidepyrid-4-yl, 5-methyl-1,2,4-triazo-3-yl, 1-methyl-1,2,4-triazo-3-yl and 2-methyloxazo-4-yl.

Favoured values for 8, 9 or 10 membered optionally substituted aromatic rings include naphthyl, tetrahydronaphthyl, indolyl, quinolinyl, isoquinolinyl, benzothienyl, benzofuryl, benzimidazolyl, imidazo[1,2-b]thiazole and imidazo[1,2-a]pyridine. The imidazo[1,2-b]thiazole and imidazo[1,2-a]pyridine group are the preferred groups.

Preferably non-aromatic rings are saturated or monounsaturated.

Favoured values for 3 to 8 membered optionally substituted non-aromatic rings include oxirane, cyclopentyl, cyclohexyl, pyrrolidinyl, pyrazolinyl, oxazolidinyl, tetrahydrothiadiazolyl, tetrahydrothiophenyl, tetrahydrofuryl, piperidinyl, piperazinyl, pyranyl, dioxanyl, morpholinyl, thiomorpholinyl, diazacyclohexyl and diazacyclohexenyl. Particularly favoured groups include optionally substituted oxirane, cyclopentyl, cyclohexyl, pyrrolidinyl, pyrazolinyl, oxazolidinyl, tetrahydrothiadiazolyl, tetrahydrothiophenyl, tetrahydrofuryl, piperidinyl, piperazinyl and morpholinyl.

Favoured 3 to 8 membered non-aromatic rings include:

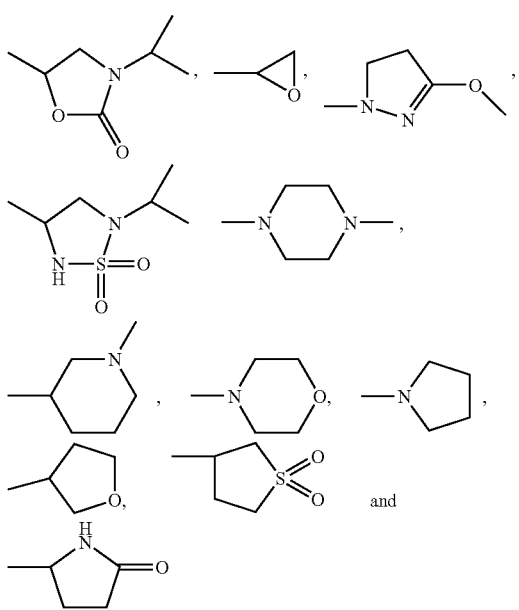

Preferably $R^4$ and $R^5$ are independently selected from hydrogen, $C_{1-6}$alkyl, —$C_{1-6}$alkylAr$^1$ or —$C_{1-6}$alkylA$^1$ or $R^4$ and $R^5$ are joined to form a non-aromatic ring of 5 or 6 atoms which may contain a double bond, and 1 or 2 of which ring atoms may be selected from N, O or S, which ring may be optionally substituted by oxo or A$^1$.

More preferably $R^4$ is hydrogen or $C_1$alkyl and $R^5$ is hydrogen, $C_{1-6}$alkyl, N-oxide pyridyl$C_{1-6}$alkyl, $C_{1-6}$alkylpiperidyl$C_{0-6}$alkyl or $C_{1-6}$alkylpyrrolidinyl; or $R^4$ and $R^5$ are joined to form an optionally substituted ring selected from piperazinyl, morpholinyl or

The optional substituents on such rings include $C_{1-6}$alkyl, $C_{1-6}$alkoxy, $C_{2-6}$alkenyl, oxo, $(CH_2)_{0-3}N(C_{1-4}$alkyl$)_2$ or pyrrolidinyl, of which methyl and OCH$_3$ are preferred.

Favourably $R^4$ is hydrogen or methyl and $R^5$ is hydrogen, methyl, N-oxidepyrid-4-ylmethyl, 1-methylpiperidin-3-ylmethyl or 1-methylpiperidin-4-yl; or $R^4$ and $R^5$ are joined to form a ring selected from 4-methylpiperazin-1-yl, morpholinyl, 4-pyrrolidinyl-piperazin-1-yl, dimethylaminomethyl-2-morpholin-4-yl or

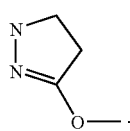

Favoured values for $X^2$ include hydrogen, hydroxy or $NR^6R^7$ wherein $R^6$ and $R^7$ are as hereinbefore defined or an optionally substituted non-aromatic ring selected from morpholinyl or piperazinyl. The optional substituents on such rings include $C_{1-6}$alkyl, $C_{1-6}$alkoxy, $C_{2-6}$alkenyl, oxo, hydroxy or tautomers thereof, of which methyl, OCH$_3$ and oxo are preferred.

Alternatively, $R^6$, $R^7$ and nitrogen atom to which they are attached form a morpholinyl, pyrrolidinyl, piperazinyl or isoindolinyl ring, which ring is optionally substituted by $C_{1-4}$alkyl or $S(O)_2C_{1-4}$alkyl.

Preferably $R^6$ and $R^7$ are independently selected from hydrogen, $C_{1-6}$alkyl, —$C_{1-6}$alkylAr$^1$, —$C_{1-6}$alkylA$^1$, —CO-phenyl, —SO$_2$N($C_{1-6}$alkyl$)_2$ or —(CO)$_2$N($C_{1-6}$alkyl$)_2$.

More preferably $R^6$ is hydrogen or $C_{1-6}$alkyl and $R^7$ is $C_{1-6}$alkyl, —CO-phenyl, —SO$_2$N($C_{1-6}$alkyl$)_2$, —(CO)$_2$N($C_{1-6}$alkyl$)_2$ or $C_{1-6}$alkyl substituted by phenyl, pyridyl or N-oxides thereof or by an optionally substituted ring selected from triazolyl, tetrahydrothiophenyl or pyrrolidinyl. The optional substituents on such rings include 1 or 2 $C_{1-2}$alkyl, $C_{1-2}$alkoxy, fluorine, chlorine, oxo or hydroxy of which methyl, OCH$_3$ and oxo are preferred.

Favourably $X^2$ is hydrogen, hydroxyl, morpholinyl or $NR^6R^7$ wherein $R^6$ is hydrogen or methyl and $R^7$ is methyl, butyl, —CO-phenyl, —SO$_2$N(CH$_3$)$_2$, —(CO)$_2$N(CH$_3$)$_2$ or methyl substituted by a ring selected from cyclopropyl, phenyl, pyrid-2-yl, pyrid-4-yl, N-oxide pyrid-4-yl, 5-methyl-1,2,4-triazo-3-yl,

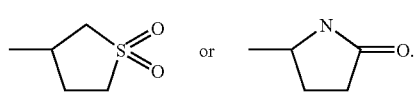

Certain particularly suitable compounds of the invention are represented by the formula (II):

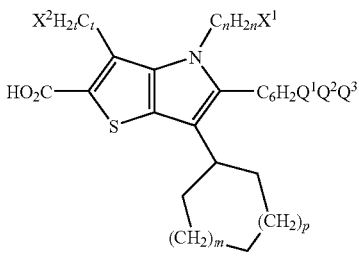

(II)

wherein m+p is 0, 1, 2, 3, 4; is favourably 1 or 2 and preferably is 2;
n is 0, 1 or 2 and is preferably 1;
t is 0, 1 or 2 and is preferably 1;
$Q^1$, $Q^2$ and $Q^3$ are as defined in relation to formula (I); and
$X^1$ and $X^2$ are independently selected from hydrogen, hydroxy, carboxy, $C_{1-6}$alkyl, $C_{1-2}$ alkoxymethyl, C(OH)HCH$_2$NH($C_{1-6}$ alkyl)
or (i) a moiety containing at least one aromatic ring and possesses 5-, 6-, 8-, 9- or 10-ring atoms 0 to 4 of which may be N, O or S heteroatoms of which at most 1 will be O or S and when N is present may be a N-oxide thereof; which group may be optionally substituted by 1 or 2 groups selected from $C_{1-6}$alkyl, $C_{4-10}$aryl, $C_{4-10}$ aryl$C_{1-6}$alkyl, fluorine or chlorine;
or (ii) a non-aromatic ring of 3 to 8, preferably 3, 5 or 6 ring atoms which may contain a double bond and up to 4 of which ring atoms may be a O, S or N atom and which ring may be optionally substituted by 1, 2 or 3 groups selected from $C_{1-6}$alkyl, $C_{2-6}$alkenyl, oxo, hydroxy or tautomers thereof;
or (iii) CONR$^4$R$^5$;
or (iv) NR$^6$R$^7$, wherein R$^4$, R$^5$, R$^6$ and R$^7$ are as hereinbefore defined;
or a pharmaceutically acceptable salt thereof.

In one embodiment $X^2$ represents hydrogen, hydroxy or $C_{1-2}$alkoxymethyl and $X^1$ represents hydrogen, carboxy, $C_{1-6}$alkyl, $C_{1-2}$alkoxymethyl, C(OH)HCH$_2$NH($C_{1-6}$alkyl) or (i), (ii), (ii) or (iv).

Aptly $X^1$ is a group (i). Aptly $X^1$ is a group (ii). Aptly $X^1$ is a group (iii). Aptly $X^1$ is (iv).

Certain particularly suitable compounds of the invention are represented by the formula (IIa):

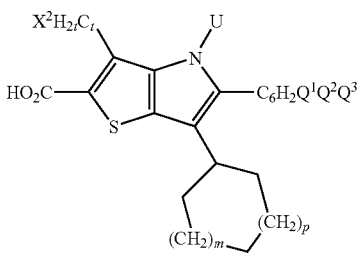

wherein m+ p is 0, 1, 2, 3, 4; is favourably 1 or 2 and preferably is 2;
t is 0, 1 or 2 and is preferably 1;
U is hydrogen, carboxy, $C_{1-6}$alkyl, $C_{1-2}$alkoxymethyl or C(OH)HCH$_2$NH($C_{1-6}$alkyl);

$Q^1$, $Q^2$ and $Q^3$ are as defined in relation to formula (I); and
$X^2$ is hydrogen, hydroxy, morpholinyl or NR$^6$R$^7$, wherein R$^6$ and R$^7$ are as hereinbefore defined;
or a pharmaceutically acceptable salt thereof.

Certain particularly suitable compounds of the invention are represented by the formula (III):

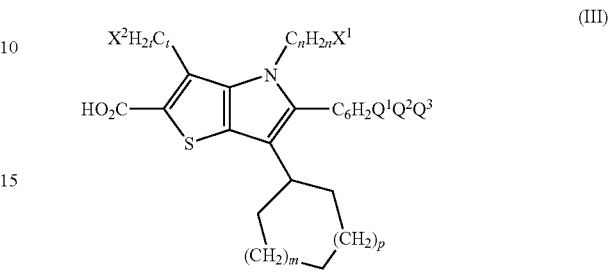

wherein m+p, n, $X^1$, $Q^1$, $Q^2$ and $Q^3$ are as defined in relation to formulas (I), (II) or (IIa) or a pharmaceutically acceptable salt thereof.

In other apt compounds of formulae (II), (IIa) and (III), $Q^1$, $Q^2$ and $Q^3$ are independently hydrogen, fluorine, chlorine, methyl, methoxyl or trifluoromethyl. In certain apt compounds of formulae (II), (IIa) and (III) $Q^1$ and $Q^2$ are each hydrogen and $Q^3$ is hydrogen, fluorine or chlorine.

Specific compounds within the scope of the present invention include:
6-cyclohexyl-5-phenyl-4H-thieno[3,2-b]pyrrole-2-carboxylic acid;
6-cyclohexyl-4-[2-(dimethylamino)-2-oxoethyl]-5-phenyl-4H-thieno[3,2-b]pyrrole-2-carboxylic acid;
6-cyclohexyl-4-(2-morpholin-4-yl-2-oxoethyl)-5-phenyl-4H-thieno[3,2-b]pyrrole-2-carboxylic acid;
3-{[[(2-carboxy-6-cyclohexyl-5-phenyl-4H-thieno[3,2-b]pyrrol-4-yl)acetyl](methyl)amino]methyl}-1-methylpiperidinium trifluoroacetate;
4-benzyl-6-cyclohexyl-5-phenyl-4H-thieno[3,2-b]pyrrole-2-carboxylic acid;
3-[(2-carboxy-6-cyclohexyl-5-phenyl-4H-thieno[3,2-b]pyrrol-4-yl)methyl]pyridinium trifluoroacetate;
1-[2-(2-carboxy-6-cyclohexyl-5-phenyl-4H-thieno[3,2-b]pyrrol-4-yl)ethyl]pyrrolidinium trifluoroacetate;
6-cyclohexyl-4-methyl-5-phenyl-4H-thieno[3,2-b]pyrrole-2-carboxylic acid;
6-cyclopentyl-5-phenyl-4H-thieno[3,2-b]pyrrole-2-carboxylic acid;
[2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl]methanaminium trifluoroacetate;
3-[(benzylamino)methyl]-6-cyclohexyl-4-(methoxymethyl)-5-phenyl-4H-thieno[3,2-b]pyrrole-2-carboxylic acid;
6-cyclohexyl-3-[(dimethylamino)methyl]-5-phenyl-4H-thieno[3,2-b]pyrrole-2-carboxylic acid;
5-(4-chlorophenyl)-6-cyclohexyl-)-4H-thieno[3,2-b]pyrrole-2-carboxylic acid;
5-(4-chlorophenyl)-6-cyclohexyl-4-[2-(dimethylamino)-2-oxoethyl]-4H-thieno[3,2-b]pyrrole-2-carboxylic acid;
methyl 6-benzyl-4-cyclohexyl-5-phenyl-6H-thieno[2,3-b]pyrrole-2-carboxylate;
and pharmaceutically acceptable salts thereof.

Further specific compounds within the scope of the present invention include:

5-(4-chlorophenyl)-6-cyclohexyl-3-[(isobutylamino)methyl]-4-{2-[(1-isopropylpyrrolidin-3-yl)(methyl)amino]-2-oxoethyl}-4H-thieno[3,2-b]pyrrole-2-carboxylic acid;

methyl 5-(4-chlorophenyl)-6-cyclohexyl-4-(2-morpholin-4yl-2-oxoethyl)-4H-thieno[3,2-b]pyrrole-2-carboxylate;

methyl 5-(4-chlorophenyl)-6-cyclohexyl-N-methyl-4-(2-morpholin-4yl-2-oxoethyl)-4H-thieno[3,2-b]pyrrole-2-carboxylate;

methyl 5-(4-chlorophenyl)-6-cyclohexyl-N-(ethylsulfonyl)-4-(2-morpholin-4yl-2-oxoethyl)-4H-thieno[3,2-b]pyrrole-2-carboxylate;

6-cyclohexyl-5-(3-furyl)-(4-{2-[(1-isopropylpyrrolidin-3-yl)methyl)amino]-2-oxoethyl}-4H-thieno[3,2-b]pyrrole-2-carboxylic acid;

6-cyclohexyl-4-methyl-5-(1,3-oxazol-5-yl)-4H-thieno[3,2-b]pyrrole-2-carboxylic acid;

4-cyclohexyl-5-phenyl-6H-thieno[2,3-b]pyrrole-2-carboxylic acid;

4-cyclohexyl-6-[2-(dimethylamino)-2-oxoethyl]-5-phenyl-6H-thieno[2,3-b]pyrrole-2-carboxylic acid;

and pharmaceutically acceptable salts thereof.

Additional specific compounds within the scope of the present invention include:

6-cyclohexyl-5-(4-fluorophenyl)-4-[2-oxo-2-(4-pyrrolidin-1-ylpiperidin-1-yl)ethyl]-4H-thieno[3,2-b]pyrrole-2-carboxylic acid;

6-cyclohexyl-5-(4-chlorophenyl)-4-[2-oxo-2-(4-pyrrolidin-1-ylpiperidin-1-yl)ethyl]-4H-thieno[3,2-b]pyrrole-2-carboxylic acid;

5-(4-chlorophenyl)-6-cyclohexyl-4-{2-[(1-isopropylpyrrolidin-3-yl)(methyl)amino]-2-oxoethyl}-4H-thieno[3,2-b]pyrrole-2-carboxylic acid;

5-(4-chlorophenyl)-6-cyclohexyl-4-(2-{2-[(dimethylamino)methyl]morpholin-4-yl}-2-oxoethyl)-4H-thieno[3,2-b]pyrrole-2-carboxylic acid;

5-(4-chlorophenyl)-6-cyclohexyl-4-{2-[methyl(1-methylpiperidin-4-yl)amino]-2-oxoethyl}-4H-thieno[3,2-b]pyrrole-2-carboxylic acid;

5-(4-chlorophenyl)-6-cyclohexyl-4-(2-{methyl[(1-methylpiperidin-3-yl)methyl]amino}-2-oxoethyl)-4H-thieno[3,2-b]pyrrole-2-carboxylic acid;

5-(4-chlorophenyl)-6-cyclohexyl-4-methyl-4H-thieno[3,2-b]pyrrole-2-carboxylic acid;

5-(3-chlorophenyl)-6-cyclohexyl-4-(2-morpholin-4-yl-2-oxoethyl)-4H-thieno[3,2-b]pyrrole-2-carboxylic acid;

5-(3-chlorophenyl)-6-cyclohexyl-4-[2-(dimethylamino)-2-oxoethyl]-4H-thieno[3,2-b]pyrrole-2-carboxylic acid;

6-cyclohexyl-5-(4-methoxyphenyl)-4-(2-morpholin-4-yl-2-oxoethyl)-4H-thieno[3,2-b]pyrrole-2-carboxylic acid;

5-[4-(benzyloxy)phenyl]-6-cyclohexyl-4-(2-morpholin-4-yl-2-oxoethyl)-4H-thieno[3,2-b]pyrrole-2-carboxylic acid;

6-cyclohexyl-5-(4-methylphenyl)-4-(2-morpholin-4-yl-2-oxoethyl)-4H-thieno[3,2-b]pyrrole-2-carboxylic acid;

6-cyclohexyl-5-(4-formylphenyl)-4-(2-morpholin-4-yl-2-oxoethyl)-4H-thieno[3,2-b]pyrrole-2-carboxylic acid;

5-(3-chloro-4-methoxyphenyl)-6-cyclohexyl-4-(2-morpholin-4-yl-2-oxoethyl)-4H-thieno[3,2-b]pyrrole-2-carboxylic acid;

6-cyclohexyl-4-[2-(dimethylamino)-2-oxoethyl]-5-(4-formylphenyl)-4H-thieno[3,2-b]pyrrole-2-carboxylic acid;

6-cyclohexyl-4-[2-(dimethylamino)-2-oxoethyl]-5-(3-formylphenyl)-4H-thieno[3,2-b]pyrrole-2-carboxylic acid;

6-cyclohexyl-5-{3-[(dimethylamino)methyl]phenyl}-4-[2-(dimethylamino)-2-oxoethyl]-4H-thieno[3,2-b]pyrrole-2-carboxylic acid;

6-cyclohexyl-4-[2-(dimethylamino)-2-oxoethyl]-5-(3-furyl)-4H-thieno[3,2-b]pyrrole-2-carboxylic acid;

6-cyclohexyl-4-[2-(dimethylamino)-2-oxoethyl]-5-(6-methoxypyridin-3-yl)-4H-thieno[3,2-b]pyrrole-2-carboxylic acid;

6-cyclohexyl-5-{4-[2-(dimethylamino)ethoxy]phenyl}-4-[2-(dimethylamino)-2-oxoethyl]-4H-thieno[3,2-b]pyrrole-2-carboxylic acid;

6-cyclohexyl-4-[2-(dimethylamino)-2-oxoethyl]-5-(3-methoxyphenyl)-4H-thieno[3,2-b]pyrrole-2-carboxylic acid;

3-{[benzyl(methyl)amino]methyl}-6-cyclohexyl-4-(methoxymethyl)-5-phenyl-4H-thieno[3,2-b]pyrrole-2-carboxylic acid;

5-(4-chlorophenyl)-6-cyclohexyl-4-methyl-3-(pyrrolidin-1-ylmethyl)-4H-thieno[3,2-b]pyrrole-2-carboxylic acid;

5-(4-chlorophenyl)-6-cyclohexyl-4-methyl-3-[(4-methylpiperazin-1-yl)methyl]-4H-thieno[3,2-b]pyrrole-2-carboxylic acid;

5-(4-chlorophenyl)-6-cyclohexyl-3-(1,3-dihydro-2H-isoindol-2-ylmethyl)-4-methyl-4H-thieno[3,2-b]pyrrole-2-carboxylic acid;

5-(4-chlorophenyl)-6-cyclohexyl-4-methyl-3-{[4-(methylsulfonyl)piperazin-1-yl]methyl}-4H-thieno[3,2-b]pyrrole-2-carboxylic acid;

5-(4-chlorophenyl)-6-cyclohexyl-4-methyl-3-{[(pyridin-4-ylmethyl)amino]methyl}-4H-thieno[3,2-b]pyrrole-2-carboxylic acid;

5-(4-chlorophenyl)-6-cyclohexyl-3-[(dimethylamino)methyl]-4-methyl-4H-thieno[3,2-b]pyrrole-2-carboxylic acid;

5-(4-chlorophenyl)-6-cyclohexyl-3-[(dimethylamino)methyl]-4-(2-morpholin-4-yl-2-oxoethyl)-4H-thieno[3,2-b]pyrrole-2-carboxylic acid;

5-(4-chlorophenyl)-6-cyclohexyl-4-(2-morpholin-4-yl-2-oxoethyl)-3-(pyrrolidin-1-ylmethyl)-4H-thieno[3,2-b]pyrrole-2-carboxylic acid;

5-(4-chlorophenyl)-6-cyclohexyl-3-[(4-methylpiperazin-1-yl)methyl]-4-(2-morpholin-4-yl-2-oxoethyl)-4H-thieno[3,2-b]pyrrole-2-carboxylic acid;

5-(4-chlorophenyl)-6-cyclohexyl-3-{[4-(methylsulfonyl)piperazin-1-yl]methyl}-4-(2-morpholin-4-yl-2-oxoethyl)-4H-thieno[3,2-b]pyrrole-2-carboxylic acid;

5-(4-chlorophenyl)-6-cyclohexyl-4-(2-morpholin-4-yl-2-oxoethyl)-3-{[(pyridin-4-ylmethyl)amino]methyl}-4H-thieno[3,2-b]pyrrole-2-carboxylic acid;

5-(4-chlorophenyl)-6-cyclohexyl-3-{[(cyclopropylmethyl)amino]methyl}-4-(2-morpholin-4-yl-2-oxoethyl)-4H-thieno[3,2-b]pyrrole-2-carboxylic acid;

5-(4-chlorophenyl)-6-cyclohexyl-3-(1,3-dihydro-2H-isoindol-2-ylmethyl)-4-(2-morpholin-4-yl-2-oxoethyl)-4H-thieno[3,2-b]pyrrole-2-carboxylic acid;

5-(4-chlorophenyl)-6-cyclohexyl-3-[(isopropylamino)methyl]-4-(2-morpholin-4-yl-2-oxoethyl)-4H-thieno[3,2-b]pyrrole-2-carboxylic acid;

5-(4-chlorophenyl)-6-cyclohexyl-3-[(isobutylamino)methyl]-4-(2-morpholin-4-yl-2-oxoethyl)-4H-thieno[3,2-b]pyrrole-2-carboxylic acid;

4-cyclohexyl-6-(2-{methyl[(1-methylpiperidin-3-yl)methyl]amino}-2-oxoethyl)-5-phenyl-6H-thieno[2,3-b]pyrrole-2-carboxylic acid;

and pharmaceutically acceptable salts thereof.

The compounds of the formula (I) may be in the form of a pharmaceutically acceptable salt such as a sodium, potassium, calcium, magnesium or ammonium salt or a salt with a pharmaceutically acceptable organic base. If the compounds of the formula (I) also contain a basic group, the compound may be zwitterionic or in the form of a salt with a pharmaceutically acceptable acid such as hydrochloric, sulphuric, phosphoric, methane sulfonic, oxalic, p-toluenesulphonic acid, and the like acid.

The present invention provides a process for the preparation of compounds of formula (I) and their salts which comprises the reaction of compounds of the formulas (IV) and (V):

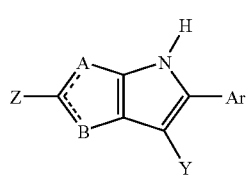
(IV)

L—$C_nH_{2n}X^1$
(V)

wherein A, B, Z, Ar, $X^1$, n and Y are as defined in formula (I) and L is a good leaving group such as chlorine, bromine, iodine, methanesulfonate, tolyenesulfonate, triflate or the like.

The compound of formula (IV) may be prepared by the reaction of the corresponding compound of formula (VI) with a compound of formula (VII) followed by reduction:

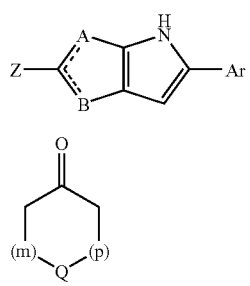
(VI)

(VII)

wherein Q is $CH_2$, NH, O or S and m+p is 1 or 2.

In an alternative synthesis, the compound of formula (IV) may be prepared by the reaction of a compound of formula (VI) with a compound of formula (VIII):

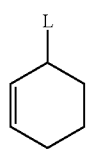
(VIII)

wherein L is as defined above.

The compound of formula (VI) wherein A is $C_rH_{2r}X^2$ and B is S may be prepared by the cyclizing reaction of a corresponding compound of formula (IX) with $(EtO)_3P$:

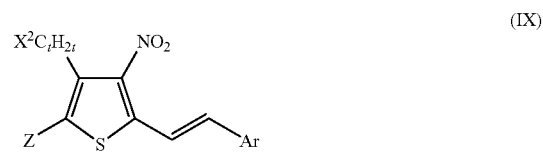
(IX)

The compound of formula (IX) may be formed from a corresponding compound of formula (X) by reaction with ArCHO:

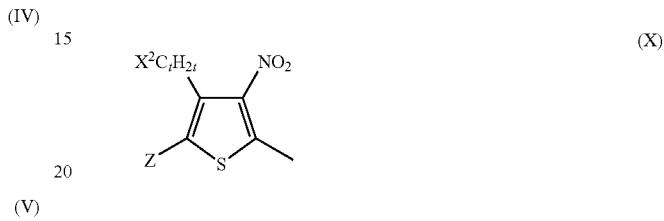
(X)

In an alternative process the compounds of formula (IV) may be prepared from the corresponding compound of formula (XI):

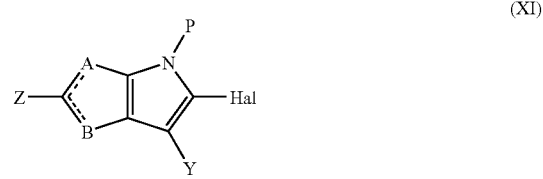
(XI)

wherein P is a protecting group such as but not limited to Boc group and Hal is preferably bromine or iodine, by reaction with $ArB(OH)_2$ or $ArSnBu_3$ in a transition-metal mediated coupling reaction or using related synthetic procedures. The transition-metal is preferably palladium.

The compound of formula (XI) may be prepared from a corresponding compound of formula (XII) by reaction with an appropriate protecting group such as but not limited to Boc, followed by reaction with NBS or NIH:

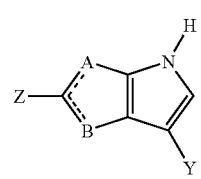
(XII)

The compound of formula (XII) may be prepared by the reaction of a corresponding compound of formula (XIII) with a compound of formula (VII) followed by reduction:

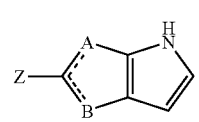
(XIII)

In addition, the compound of formula (XIII) where B is S and A is C—$C_tH_{2t}X_2$ can be prepared by reaction of a corresponding compound of formula (XIV) with $Bu_4NF$:

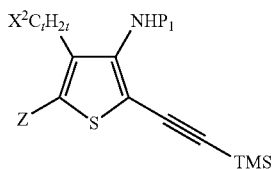

(XIV)

wherein $P_1$ is a protecting group such as but not limited to Boc, $CH_3CO$ or $CF_3CO$ groups.

The compound of the formula (XIV) may be prepared from compounds of the formulae (XV) and (XVI) under Sonogashira coupling conditions:

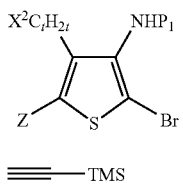

(XV)

(XVI)

wherein $P_1$ is as described above.

In an alternative synthesis the compound of formula (XVII) may be prepared by the following reaction scheme:

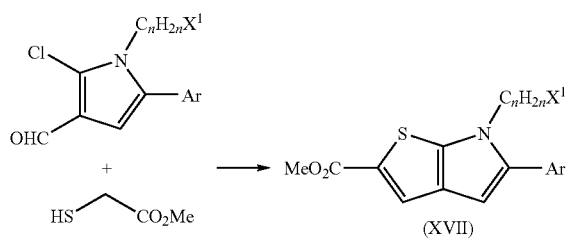

(XVII)

which may be followed by reaction with a compound of formula (VII) as described hereinbefore and subsequent hydrolysis of the carboxylic ester derivative.

In an alternative synthesis, the compound of formula (XIX) may be prepared by the following reductive amination reaction.

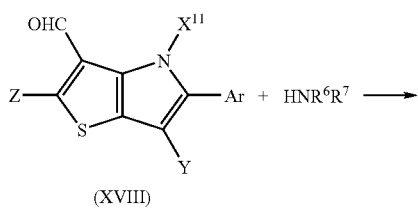

(XVIII)

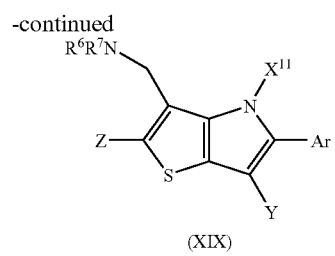

(XIX)

wherein Z, Ar, Y, $R^6$ and $R^7$ are as defined in formula (I) and $X^{11}$ is a suitable protecting group such as but not limited to methoxymethyl.

The compounds of formula (XIX) wherein $R^7$ is hydrogen may be further elaborated by amidation, sulfonylation or related processes.

The compound of formula (XVIII) may be prepared by protection of the corresponding compound of formula (IV) wherein A is C—H and B is S with an appropriate protecting groups such as but not limited to methoxymethyl, followed by metalation and formylation.

In all reactions described herein any reaction groups that require masking during reaction may be protected in conventional manner and the protecting group removed thereafter. For example, if the desired compound of the formula (I) contains a $CO_2H$ group, then the compound of the formula (IV) may contain a $CO_2CH_3$ group and the resulting compound of the formula (I) may be hydrolysed in conventional manner, for example with sodium hydroxide in aqueous methanol or $BBr_3$ in DCM to yield the compound containing the carboxylate or its sodium salt.

The compounds of formulas (I)-(III) may be used for the inhibition of HCV polymerase and so may be used for the manufacture of medicaments which may be used to treat or prevent HCV infection.

Accordingly this invention provides a pharmaceutical composition comprising a compound of the formula (I) as hereinbefore described or a pharmaceutically acceptable salt thereof together with a pharmaceutically acceptable carrier.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of infection due to hepatitis C, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. Most suitably the administration is orally using a unit done as previously indicated.

In a further aspect this invention provides the use of a compound of Formula (I) or a pharmaceutically acceptable salt thereof in the manufacture of a medicament for the treatment or prevention of infection by hepatitis C virus. Most suitably the medicament is in unit dose form adapted for oral administration as indicated hereinbefore.

In another aspect this invention provides the use of a compound of Formula (I) or a pharmaceutically acceptable salt thereof for the treatment or prevention of infection by hepatitis C virus in a mammal and preferably in a human. Most suitably the treatment is effected by oral administration of a unit dose form as indicated hereinbefore.

Useful references in the literature for synthetic preparations include: Srinivasan et al, Synthesis, 1973, 313; Freter, J. Org. Chem., 1975, 40, 2525; Olesen et al, J. Heterocyclic. Chem., 1995, 32, 1641; and Wensbo et al, Tetrahedron Lett., 1993, 26, 2823; and Carpenter et al, Tetrahedron Lett., 1985, 26, 1777.

The following Examples are illustrative of this invention.

The compounds of the invention were tested for inhibitory activity against the HCV RNA dependent RNA polymerase (NS5B) in an enzyme inhibition assay (example i)) and an cell based sub-genomic replication assay (describe in example ii)). The compounds generally have IC50's below 5 μM in the enzyme assay and EC50's below 50 in the cell based assay.

i) In-vitro HCV NS5B Enzyme Inhibition Assay

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{60}$ values by utilising the formula:

$$\% \text{ Residual activity}=100/(1+[I]/IC_{50})^S$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described by De Francesco, Raffaele; Migliaccio, Giovanni; Paonessa, Giacomo. Hepatitis C virus replicons and replicon enhanced cells. PCT Int. Appl. WO 0259321 A2 20020801). Cells were seeded into 96 well plates at a density of $10^4$ cells per well in a final volume of 0.1 ml of DMEM/10% FCS. Two hours after plating, 50 μl of DMEMA10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+0.1% Triton X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition}=1-(Ai-b)/(A_0-b)=[I]^n/([I]^n+IC_{50})$$

where:
Ai=absorbance value of HBI10 cells supplemented with the indicated inhibitor concentration.
$A_0$=absorbance value of HBI10 cells incubated without inhibitor.
b=absorbance value of Huh-7 cells plated at the same density in the same microtiter plates and incubated without inhibitor.
n=Hill coefficient.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage corporation and Jones Flashmaster) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H nmr spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; br, broad, and combinations thereof); coupling constant(s) in hertz; number of protons. Mass spectral (MS) data were obtained on a Perkin Elmer API 100 operating in negative (ES$^-$) or positive (ES$^+$) ionization mode and results are reported as the ratio of mass over charge (m/z) for the parent ion only. Preparative scale HPLC separations were carried out on a Waters Delta Prep 4000 separation module, equipped with a Waters 486 absorption detector or on a Thermoquest P4000 equipped with a Uv1000 absorption detector. In all cases compounds were eluted with linear gradients of water and acetonitrile both containing 0.1% TFA using flow rates between 15 and 25 ml/min.

The following abbreviations are used in the examples, the schemes and the tables:

DMF: dimethylformamide; DCM: dichloromethane; DMSO: dimethylsulfoxide; TFA: trifluoroacetic acid; THF: tetrahydrofuran; MeOH: methanol; EtOH: ethanol; AcOEt: ethyl acetate; MeCN: acetonitrile; Et$_2$O: diethyl ether; DME: 1,2-dimethoxyethane; DCE: 1,2-dichloroethane; HCl: hydrogen chloride; NaOH: sodium hydroxide; NaHCO$_3$: sodium hydrogencarbonate; Na$_2$CO$_3$: sodium carbonate; K$_2$CO$_3$: potassium carbonate; Na$_2$S$_2$O$_3$: sodium thiosulfate; in: minutes; h: hour(s); eq.: equivalent(s); wt: weight; RT: room temperature; TLC: thin-layer chromatography; RP-HPLC: reversed phase high-pressure liquid chromatography; DIEA: diisopropylethyl amine; Et$_3$N: triethylamine; DMAP: dimethylaminopyridine; TMEDA: N,N,N',N'-tetramethylethylenediamine; DBU: 1,8-Diazabicyclo[5.4.0]undec-7-ene; HATU: O-(7-azabenzotriazol-1-yl)-N,N,N',N'-tetramethyluronium hexafluorophosphate; TPAP: tetrapropylammonium perruthenate; BEMP: 2-tert-butylimino-2-diethylamino-1,3-dimethylperhydro-1,3,2-diazaphosphorine; NBS: N-bromosuccinimide; POCl$_3$: phosphorus oxychloride; TosMIC: (p-tolylsulfonyl)methyl isocyanide); BBr$_3$: boron tribromide; NaH: sodium hydride; Boc$_2$O: Di-tert-butyl dicarbonate; sec-BuLi: sec-butyllithium; n-Bu$_4$NF: tetra-n-butylammonium fluoride; p-TsOH: p-toluenesulfonic acid; MeI: iodomethane; CDI: 1,1-carbonyldiimidazole; LiCl: lithium chloride; ZnCl$_2$: zinc chloride; CuI: copper(I) iodide; P(t-Bu)$_3$: tri-tert-butylphosphine; Pd(PPh$_3$)$_4$: tetrakis(triphenylphosphine)palladium(0); Pd(PhCN)$_2$Cl$_2$: dichlorobis (benzonitrile)palladium(II); PdCl$_2$(PPh)$_2$: dichlorobis(triphenylphosphine)palladium(II); PdCl$_2$(dppf)$_2$: dichloro[1,1'-bis(diphenylphosphino)ferrocene]palladium(II); Pd(dba)$_3$: tris(dibenzylideneacetone)dipalladium(0); NaBH$_3$CN: sodium cyanoborohydride.

EXAMPLE 1

6-cyclohexyl-5-phenyl-4H-thieno[3,2-b]pyrrole-2-carboxylic acid

Step 1: methyl 5-methyl-4-nitrothiophene-2-carboxylate

A solution (0.5 M) of 5-methyl-4-nitrothiophene-2-carboxylic acid in methanol was treated with sulfuric acid (3.5 eq.). The reaction mixture was heated to reflux for 48 h. After cooling down, solvent was evaporated giving a residue that was dissolved in AcOEt and water was added. The organic phase was separated and the aqueous layer was extracted with AcOEt. The combined organic phase was washed sequentially with aqueous NaHCO$_3$ (saturated solution) and brine, then dried and concentrated giving the title compound (69%) as solid.

$^1$H NMR (300 MHz, CDCl$_3$, 300 K) δ 2.84 (s, 3H), 3.91 (s, 3H), 8.20 (s, 1H); MS (ES$^+$) m/z 202 (M+H)$^+$.

Step 2: methyl 4-nitro-5-[(E)-2-phenylethenyl]thiophene-2-carboxylate

A solution (0.33 M) of methyl 5-methyl-4-nitrothiophene-2-carboxylate in MeOH, was treated with benzaldehyde (1.5 eq.). The reaction mixture was heated to reflux and when it became a clear solution a catalytic amount of pyrrolidine (0.01 eq.) was added. After 18 h at reflux additional pyrrolidine (0.01 eq.) was added. The reaction was heated to reflux for 40 h. After cooling down, evaporation of the solvent gave a residue that was purified by flash chromatography on silica gel (1:9 AcOEt/petroleum ether) to afford the title compound (67%) as a solid.

$^1$H NMR (400 MHz, CDCl$_3$, 300 K) δ 3.94 (s, 3H), 7.32 (d, J=16.2 Hz, 1H), 7.4-7.5 (m, 3H), 7.59 (d, J=7.13 Hz, 2H), 8.12 (d, J=16.2 Hz, 1H), 8.22 (s, 1H); MS (ES$^+$) m/z 290 (M+H)$^+$.

Step 3: methyl 5-phenyl-4H-thieno[3,2-b]pyrrole-2-carboxylate

A solution (1 M) of methyl 4-nitro-5-[(E)-2-phenylethenyl]thiophene-2-carboxylate in triethyl phosphite was heated to reflux for 28 h. After cooling down a part of the solvent was evaporated under high vacuum (2 mbar, water bath 60° C.) then the residue was purified by flash chromatography on silica gel (1:4 acetone/toluene) to afford the title compound (32%) as a solid.

$^1$H NMR (400 MHz, DMSO-d$_6$, 300 K) δ 3.86 (s, 3H), 7.01 (s, 1H), 7.34 (t, J=6.9 Hz, 1H), 7.49 (t, J=7.6 Hz, 2H), 7.71 (s, 1H), 7.82 (d, J=8.2 Hz, 2H), 12.08 (s, 1H); MS (ES$^+$) m/z 258 (M+H)$^+$.

Step 4: methyl 6-cyclohex-1-en-1-yl-5-phenyl-4H-thieno[3,2-b]pyrrole-2-carboxylate A solution (0.2 M) of methyl 5-phenyl-4H-thieno[3,2-b]pyrrole-2-carboxylate in acetic acid was treated with acetic anhydride (10 eq.), cyclohexanone (10 eq.) and 85% phosphoric acid (2.3 eq.). The mixture was heated at 80° C. for 3 h, then was poured into ice cold ammonium hydroxide. The product was extracted with AcOEt and the combined organic layers were washed sequentially with aqueous HCl (1 N), aqueous NaHCO$_3$ (saturated solution) and brine then dried and concentrated. The crude was purified by flash chromatography on silica gel (1:4 AcOEt/petroleum ether) affording the title compound (69%) as a solid.

¹H NMR (300 MHz, CDCl₃, 300 K) δ 1.67 (m, 4H) 2.18 (m, 4H), 3.89 (s, 3H), 5.95 (m, 1H), 7.39 (m, 3H), 7.53 (m, 2H), 7.67 (s, 1H), 8.25 (bs, 1H); MS (ES⁺) m/z 338 (M+H)⁺.

Step 5: methyl 6-cyclohexyl-5-phenyl-4H-thieno[3,2-b]pyrrole-2-carboxylate

A solution (0.1 M) of methyl 6-cyclohex-1-en-1-yl-5-phenyl-4H-thieno[3,2-b]pyrrole-2-carboxylate in TFA at 0° C. was treated with triethylsilane (1.5 eq.). The reaction mixture was stirred at 0° C. for 1 h then solvent was evaporated to give the title compound (95%) as a solid.

¹H NMR (300 MHz, CDCl₃, 300 K) δ 1.34 (m, 3H), 1.85 (m, 7H), 2.84 (m, 1H), 3.90 (s, 3H), 7.39 (m, 1H), 7.46 (m, 4H), 7.68 (s, 1H), 8.18 (bs, 1H); MS (ES⁺) m/z 340 (M+H)⁺.

Step 6: 6-cyclohexyl-5-phenyl-4H-thieno[3,2-b]pyrrole-2-carboxylic acid

A solution (0.07 M) of methyl 6-cyclohexyl-5-phenyl-4H-thieno[3,2-b]pyrrole-2-carboxylate in THF/MeOH (1:1) was treated with aqueous NaOH (2 N solution, 15 eq.). The mixture was heated to reflux for 90 min then concentrated and acidified to pH 1 with aqueous HCl (6 N) and extracted with AcOEt. The combined organic phase was washed with brine then dried and concentrated to give the title compound (93%) as a solid.

¹H NMR (600 MHz, DMSO-d₆, 300 K) δ 1.2-1.4 (m, 3H), 1.6-1.9 (m, 7H), 2.4-2.8 (t, J=11.6 Hz, 1H), 7.2-7.3 (m, 1H), 7.4-7.5 (m, 4H), 7.6 (s, 1H), 12.80 (bs, 1H); MS (ES⁺) m/z 326 (M+H)⁺.

EXAMPLE 2

6-cyclohexyl-4-[2-(dimethylamino)-2-oxoethyl]-5-phenyl-4H-thieno[3,2-b]pyrrole-2-carboxylic acid Step 1: methyl 4-(2-tert-butoxy-2-oxoethyl)-6-cyclohexyl-5-phenyl-4-thieno[3,2-b]pyrrole-2-carboxylate A solution (0.5 M) of methyl 6-cyclohexyl-5-phenyl-4H-thieno[3,2-b]pyrrole-2-carboxylate in DMF was treated with NaH (2 eq., 60% dispersion in mineral oil), and the suspension was stirred at RT for 30 min then tert-butyl bromoacetate (3 eq.) was added. The reaction mixture was heated at 50° C. for 1 h and 25 min then it was diluted with AcOEt and ammonium chloride (saturated solution) was added. The aqueous phase was separated and extracted with AcOEt. The combined organic phase was washed sequentially with aqueous HCl (1 N), aqueous NaHCO₃ (saturated solution) and brine then dried and evaporated. The residue was purified by flash chromatography on silica gel (1:8 AcOEt/petroleum ether) to afford the title compound (95%) as a solid.

¹H NMR (300 MHz, CDCl₃, 300 K) δ 1.1-1.2 (m, 3H), 1.33 (s, 9H), 1.6-1.8 (m, 7H), 2.46 (m, 1H), 3.80 (s, 3H), 4.39 (s, 2H), 7.25-7.29 (m, 2H), 7.30-7.40 (m, 3H), 7.60 (s, 1H); MS (ES⁺) m/z 454 (M+H)⁺.

Step 2: [6-cyclohexyl-2-(methoxycarbonyl)-5-phenyl-4H-thieno[3,2-b]pyrrol-4-yl]acetic acid A solution (0.1 M) of methyl 4-(2-tert-butoxy-2-oxoethyl)-6-cyclohexyl-5-phenyl-4H-thieno[3,2-b]pyrrole-2-carboxylate in DCM/TFA (1:1) was stirred at RT for 4 h. Evaporation of the solvent gave the title compound (100%) as a solid.

¹H NMR (300 MHz, DMSO-d₆, 300 K) δ 1.1-1.2 (m, 3H), 1.5-1.7 (m, 7H), 2.39 (t, J=12 Hz, 1H), 3.78 (s, 3H), 4.68 (s, 2H), 7.28 (d, J=6.6 Hz, 2H), 7.4-7.5 (m, 3H), 7.90 (s, 1H); MS (ES⁺) m/z 398 (M+H)⁺.

Step 3: 6-cyclohexyl-4-[2-(dimethylamino)-2-oxoethyl]-5-phenyl-4H-thieno[3,2-b]pyrrole-2-carboxylic acid A solution (0.08 M) of 6-cyclohexyl-2-(methoxycarbonyl)-5-phenyl-4H-thieno[3,2-b]pyrrol-4-yl]acetic acid in DMF was treated with were DIEA (3 eq.), dimethylamine (1.1 eq.) and HATU (1.1 eq.). The mixture was stirred at RT for 18 h then it was diluted with AcOEt and washed sequentially with aqueous NaHCO₃ (saturated solution) and brine then dried. Evaporation of the solvent gave a residue that was dissolved in DCM. The resulting solution (0.08 M) was treated with BBr₈ (1 M solution in DCM, 3 eq.) and the mixture was stirred at RT for 18 h. The solution was quenched with aqueous HCl (1 N) then the solvent was evaporated to give a residue that was purified by RP-HPLC (Conditions: Waters X-TERRA MS C18, 10 micron, 19×150 mm; flow: 18 mL/min; Gradient: A: H₂O+0.05% TFA; B: MeCN+0.05% TFA; 80% A isocratic for 2 min, linear to 70% A in 2 min, linear to 60% A in 2 min, linear to 50% A in 2 min, isocratic for 6 min, linear to 45% A in 2 min, isocratic for 2 min then linear to 35% A in 1 min) to afford the title compound (51%) as a solid.

¹H NMR (300 MHz, DMSO-d₆, 300 K) δ 1.1-1.3 (m, 3H), 1.6-1.9 (m, 7H), 2.47 (m, 1H), 2.82 (s, 3H), 2.89 (s, 3H), 4.83 (s, 2H), 7.3-7.4 (m, 2H), 7.4-7.6 (m, 3H), 7.78 (s, 1H); MS (ES⁺) m/z 411 (M+H)⁺.

EXAMPLE 3

6-cyclohexyl-4-(2-morpholin-4-yl-2-oxoethyl)-5-phenyl-4H-thieno[3,2-b]pyrrole-2-carboxylic acid Following the procedure described above for 6-cyclohexyl-4-[2-(dimethylamino)-2-oxoethyl]-5-phenyl-4N-thieno[3,2-b]pyrrole-2-carboxylic acid (step 3), treatment of a solution (0.08 M) of [6-cyclohexyl-2-(methoxycarbonyl)-5-phenyl-4H-thieno[3,2-b]pyrrol-4-yl]acetic acid in DMF with morpholine (1.1 eq.), DIEA (3 eq.) and HATU (1.1 eq.) followed by treatment of a solution (0.1 M) of the resulting residue in DCM with BBr₃ (1 M solution in DCM, 3 eq.) gave a residue that was purified by RP-HPLC (Conditions: Waters X-TERRA MS C18, 5 micron, 19×150 mm; flow: 17 mL/min; Gradient: A: H₂O+0.05% TFA; B: MeCN+0.05% TFA; 60% A isocratic for 4 min, linear to 50% A in 2 min, linear to 40% A in 2 min then isocratic for 2 min, linear to 35% A in 2 min isocratic for 1 min then linear to 30% A isocratic for 1 min then linear to 0% A in 3 min) to afford the title compound (43%) as a solid.

¹H NMR (300 MHz, DMSO-d₆, 300 K) δ 1.1-1.3 (m, 3H), 1.5-1.7 (m, 7H), 2.45 (m, 1H), 3.3-3.5 (m, 8H), 4.85 (s, 2H), 7.3-7.4 (m, 2H), 7.4-7.5 (m, 3H), 7.78 (s, 1H), 12.7 (bs, 1H); MS (ES⁺) m/z 453 (M+H)⁺.

EXAMPLE 4

3-{([[(2-carboxy-6-cyclohexyl-5-phenyl-4H-thieno[3,2-b]pyrrol-4-yl)acetyl] (methyl)amino]methyl}-1-methylpiperidinium trifluoroacetate Following the procedure described above for 6-cyclohexyl-4-[2-(dimethylamino)-2-oxoethyl]-5-phenyl-4H-thieno[3,2-b]pyrrole-2-carboxylic acid (step 8), treatment of a solution (0.1 M) of [6-cyclohexyl-2-(methoxycarbonyl)-5-phenyl-4H-thieno[3,2-b]pyrrol-4-yl]acetic acid in DMF with 1-N-methyl-1-(1-methylpiperidin-3-yl)methanamine (1.1 eq.), DIEA (3 eq.) and HATU (1.1 eq.) followed by treatment of a solution (0.1 M) of the resulting residue in DCM with BBr₃ (1 M solution in DCM, 3 eq.) gave a residue that was purified by RP-HPLC (Conditions: Waters X-TERRA MS C18, 5 micron, 19×150 mm; flow: 20 mL/min; Gradient: A: H$_2$O+0.05% TFA; B: MeCN+0.05% TFA; 95% A isocratic for 2 min, linear to 93% A in 1 min, linear to 90% in 2 min, linear to 85% A in 2 min, linear to 75% A in 3 min, linear to 50% A in 2 min, linear to 30% A in 2 min, linear to 0% A in 2 min) to afford the title compound (57%) as a solid.

$^1$H NMR (600 MHz, pyridine-d$_5$, 300 K) 2 rotamer 4.6:1*, δ 0.8-0.9*, 0.9-1.0 (m, 1H), 1.1-1.3 (m, 3H), 1.4-1.42*, 1.45-1.5 (m, 1H), 1.5-1.6 (m, 1H), 1.6-1.7 (m, 3H), 1.8-1.95 (m, 5H), 2.0-2.1*, 2.15-2.22*, 2.25-2.3*, 2.35-2.5 (m, 3H), 2.70 (s, 3H), 2.7-2.8 (m, 1H), 2.83 (s, 3H), 2.89*, 2.95-3.05 (m, 1H), 3.15-3.25*, 3.25-3.30 (m, 1H), 3.35-3.45 (m, 1H), 3.6-3.65 (m, 1H), 5.02 (dd, J=65.6 Hz, J$_2$=17.2 Hz, 2H), 5.03-5.04*, 7.4-7.5 (m, 1H), 7.5-7.6 (m, 2H), 7.6-7.7 (m, 2H), 8.27*, 8.34 (s, 1H); $^{13}$C NMR (600 MHz, pyridine-d$_5$, 300 K) 2 rotamer δ 23.10, 26.25, 26.79, 33.43, 33.68*, 33.76, 34.21, 36.05, 44.01, 47.75, 48.01*, 50.56, 51.62*, 54.44, 55.31*, 57.73, 117.50, 117.67*, 121.21, 127.01, 128.85, 129.10, 131.02, 131.16*, 132.36, 132.81, 138.81, 140.66, 166.17, 167.67*, 168.39; MS (ES$^+$) m/z 510 (M+H)$^+$.

EXAMPLE 5

4-benzyl-6-cyclohexyl-5-phenyl-4H-thieno[3,2-b]pyrrole-2-carboxylic acid

A solution (0.15 M) of methyl 6-cyclohexyl-5-phenyl-4H-thieno[3,2-b]pyrrole-2-carboxylate in DMF at 0° C. was treated with NaH (3.5 eq., 60% dispersion in mineral oil), and the suspension was stirred at RT for 30 min then it was treated with benzyl bromide (2.5 eq.). The reaction mixture was stirred at RT for 3 h then it was diluted with Et$_2$O and water then the layers were separated and the aqueous phase was extracted with AcOEt. The combined organic phase was dried and concentrated giving a residue that was purified by flash chromatography on silica gel (1:10 MeOH/DCM) affording the title compound (22%) as a solid.

$^1$H NMR (400 MHz, DMSO-d$_6$, 300 K) δ 1.1-1.3 (m, 3H), 1.6-1.8 (m, 7H), 2.49 (m, 1H), 5.20 (s, 2H), 6.9-7.0 (m, 2H), 7.2-7.3 (m, 3H), 7.3-7.4 (m, 2H), 7.4-7.6 (m, 4H); MS (ES$^+$) m/z 416 (M+H)$^+$.

EXAMPLE 6

3-[(2-carboxy-6-cyclohexyl-5-phenyl-4H-thieno[3,2-b]pyrrol-4-yl)methyl]pyridinium trifluoroacetate A solution (0.1 M) of methyl 6-cyclohexyl-5-phenyl-4H-thieno[3,2-b]pyrrole-2-carboxylate in DMF at 0° C. was treated with NaH (8 eq., 60% dispersion in mineral oil), and the suspension was stirred at RT for 30 min then it was treated with 3-(chloromethyl)pyridine hydrochloride (4 eq.). The reaction mixture was heated to 80° C. for 1 h and left at RT for 18 h then it was quenched with ammonium chloride (saturated solution) and extracted with AcOEt. The combined organic phase was dried and concentrated giving a residue that was dissolved in MeOH. The resulting solution (0.06 M) was treated with aqueous NaOH (2 N solution, 17 eq.) then the mixture was heated to reflux for 2 h. After cooling down, the mixture was concentrated and the residue was purified by RP-HPLC (Conditions: Waters X-TERRA MS C18, 5 micron, 19×150 mm; flow: 20 mL/min; Gradient: A: H$_2$O+ 0.05% TFA; B: MeCN+0.05% TFA; 90% A isocratic for 1 min, linear to 0% A in 3 min) to afford the title compound (38%) was obtained as a solid.

$^1$H NMR (400 MHz, DMSO-d$_6$, 300 K) δ 1.1-1.3 (m, 3H), 1.6-1.8 (m, 7H), 2.4-2.5 (m, 1H), 5.37 (s, 2H), 7.3-7.6 (m, 7H), 7.87 (s, 1H), 8.20 (s, 1H), 8.55 (d, J=4.71 Hz, 1H); MS (ES$^+$) m/z 418 (M+H)$^+$.

EXAMPLE 7

1-[2-(2-carboxy-6-cyclohexyl-5-phenyl-4H-thieno[3,2-b]pyrrol-4-yl)ethyl]pyrrolidinium trifluoroacetate A solution (0.1 M) of methyl 6-cyclohexyl-5-phenyl-4H-thieno[3,2-b]pyrrole-2-carboxylate in DMF at 0° C. was treated with NaH (1.5 eq., 60% dispersion in mineral oil), and the suspension was stirred at RT for 30 min then it was treated with 1-(2-chloroethyl)pyrrolidine (3 eq.). The mixture was heated to 80° C. for 16 h then it was quenched with ammonium chloride (saturated solution), basified with aqueous NaOH (1 N) and extracted with AcOEt. The combined organic phase was washed with brine and dried. Evaporation of the solvent gave a residue that was purified by flash chromatography on silica gel (5:95 MeOH/DCM) to afford methyl 6-cyclohexyl-5-phenyl-4-(2-pyrrolidin-1-ylethyl)-4H-thieno[3,2-b]pyrrole-2-carboxylate as a solid that was dissolved in MeOH. The resulting solution (0.06 M) was treated with aqueous NaOH (2 N solution, 16 eq.) then the mixture was heated to reflux for 2 h. After cooling down, the mixture was concentrated and the residue was purified by RP-HPLC (Conditions: Waters X-TERRA MS C18, 5 micron, 10×100 mm; flow: 5 mL/min; Gradient: A: H$_2$O+ 0.05% TFA; B: MeCN+0.05% TFA; 60% A isocratic for 2 min, linear to 60% A in 3 min, linear to 50% in 2 min then linear to 40% A in 3 min) to afford the title compound (62%) as a solid.

$^1$H NMR (400 MHz, DMSO-d$_6$, 300 K) δ 1.1-1.3 (m, 3H), 1.5-1.8 (m, 9H), 1.9-2.0 (m, 2H), 2.4 (t, J=11.9 Hz, 1H), 2.8-3.0 (m, 2H), 3.3-3.4 (m, 4H), 4.2 (t, J=7.6 Hz, 2H), 7.4-7.5 (m, 2H), 7.5-7.6 (m, 3H), 8.0 (s, 1H), 9.6 (bs, 1H); MS (ES$^+$) m/z 423 (M+H)$^+$.

EXAMPLE 8

6-cyclohexyl-4-methyl-5-phenyl-4H-thieno[3,2-b]pyrrole-2-carboxylic acid

A solution (0.1 M) of methyl 6-cyclohexyl-5-phenyl-4H-thieno[3,2-b]pyrrole-2-carboxylate in THF at 0° C. was treated with NaH (4 eq., 60% dispersion in mineral oil), and the suspension was stirred at RT for 30 min then it was treated dimethyl sulfate (3 eq.). The mixture was stirred at RT for 2 h then it was quenched with water and extracted with AcOEt. The combined organic phase was washed with aqueous NaHCO$_3$ (saturated solution) then dried. Evaporation of the solvent gave a residue that was dissolved in MeOH. The resulting solution (0.13 M) was treated with aqueous NaOH (2 N solution, 8 eq.) then the mixture was heated to reflux for 2 h. After cooling down, the mixture was concentrated and the residue was purified by RP-HPLC (Conditions: Waters X-TERRA MS C18, 5 micron, 19×150 mm; flow: 18 mL/min; Gradient: A: H$_2$O+0.05% TFA; B: MeCN+0.05% TFA; 95% A linear to 90% A in 2 min, linear to 60% A in 2 min, linear to 40% in 2 min, linear to 30% A in 2 min, linear to 0% A in 2 min) to afford the title compound (42%) as a solid.

$^1$H NMR (300 MHz, DMSO-d$_6$, 300 K) δ 1.1-1.3 (m, 3H), 1.5-1.8 (m, 7H), 2.4-2.5 (m, 1H), 3.59 (s, 3H), 7.4-7.6 (m, 5H), 7.88 (s, 1H); MS (ES$^+$) m/z 340 (M+H)$^+$.

EXAMPLE 9

6-cyclopentyl-5-phenyl-4H-thieno[3,2-b]pyrrole-2-carboxylic acid

Step 1: methyl 6-cyclopentyl-5-phenyl-4H-thieno[3,2-b]pyrrole-2-carboxylate

Following the procedure described above for methyl 6-cyclohexyl-5-phenyl-4H-thieno[3,2-b]pyrrole-2-carboxylate (Example 1, steps 4 & 5), treatment of a solution (0.1 M) for methyl 5-phenyl-4H-thieno[3,2-b]pyrrole-2-carboxylate with acetic anhydride (10 eq.), cyclopentanone (10 eq.) and 85% phosphoric acid (8 eq.) and then treatment of a solution (0.1 M) of the resulting residue in TFA with triethylsilane (1.5 eq.) gave a crude that was purified by flash chromatography on silica gel (1:4 AcOEt/petroleum ether) affording the title compound (23%) as a solid.

$^1$H NMR (300 MHz, CDCl$_8$, 300 K) δ 1.6-2.0 (m, 8H), 3.2-3.3 (m, 1H), 3.90 (s, 3H), 7.3-7.5 (m, 5H), 7.70 (s, 1H), 8.21 (bs, 1H); MS (ES$^+$) m/z 326 (M+H)$^+$.

Step 2: 6-cyclopentyl-5-phenyl-4H-thieno[3,2-b]pyrrole-2-carboxylic acid

A solution (0.015 M) of methyl 6-cyclopentyl-5-phenyl-4H-thieno[3,2-b]pyrrole-2-carboxylate in THF/MeOH (1:1) was treated with aqueous NaOH (2 N solution, 20 eq.) then the mixture was heated to reflux for 45 min. After cooling down, the mixture was concentrated then the residue diluted with water and acidified to pH 2-3 with aqueous HCl (1 N) and extracted with AcOEt. The combined organic phase was dried and concentrated to give a residue that was purified by RP-HPLC (Conditions: Waters X-TERRA MS C18, 10 micron, 19×150 mm; flow: 20 mL/min; Gradient: A: H$_2$O+ 0.05% TFA; B: MeCN+0.05% TFA; 90% A isocratic for 2 min then linear to 10% A in 9 min) to afford the title compound (73%) as a solid.

$^1$H NMR (400 MHz, DMSO-d$_6$, 300 K) δ 1.6-1.7 (m, 2H), 1.7-1.9 (m, 4H), 1.9-2.0 (m, 2H), 3.2-3.3 (m, 1H), 7.4-7.5 (m, 1H), 7.5-7.6 (m, 4H), 7.62 (s, 1H), 11.57 (s, 1H), 12.62 (bs, 1H); MS (ES$^+$) m/z 312 (M+H)$^+$.

EXAMPLE 10

[2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl]methanaminium trifluoroacetate Step 1: methyl 6-cyclohexyl-4-(methoxymethyl)-5-phenyl-4H-thieno[3,2-b]pyrrole-2-carboxylate A solution (0.25 M) of methyl 6-cyclohexyl-5-phenyl-4H-thieno[3,2-b]pyrrole-2-carboxylate in DMF at 0° C. was treated with NaH (1.5 eq., 60% dispersion in mineral oil), and the suspension was stirred at 0° C. for 60 min then it was treated with chloromethyl methyl ether (5 eq.). The mixture was stirred at RT for 2 h then it was quenched with ice/water and extracted with AcOEt. The combined organic phase was washed with brine and dried. Evaporation of the solvent under reduced pressure gave a residue that was purified by flash chromatography on silica gel (1:12 acetone/toluene) to afford the title compound (92%) as an oil.

$^1$H NMR (400 MHz, CDCl$_3$, 300 K) δ 1.2-1.3 (m, 3H), 1.6-1.8 (s, 7H), 2.5-2.6 (m, 1H), 3.23 (s, 3H), 3.91 (s, 3H), 5.15 (s, 2H), 7.4-7.5 (m, 5H), 7.80 (s, 1H); MS (ES$^+$) m/z 384 (M+H)$^+$.

Step 2: 6-cyclohexyl-4-(methoxymethyl)-5-phenyl-4H-thieno[3,2-b]pyrrole-2-carboxylic acid A solution (0.1 M) of methyl 6-cyclohexyl-4-(methoxymethyl)-5-phenyl-4H-thieno[3,2-b]pyrrole-2-carboxylate in THF/MeOH (1:1) was treated with aqueous NaOH (1 N solution, 5 eq.). The mixture was stirred at RT for 21 h then concentrated and acidified to pH 4-5 with aqueous HCl (1 N) and extracted with AcOEt. The combined organic phase was dried and concentrated to give a residue that was triturated with MeCN/Et$_2$O (20:1) and filtered to afford the title compound (93%) as a solid.

$^1$H NMR (400 MHz, DMSO-d$_6$, 300 K) δ 1.2-1.3 (m, 3H), 1.6-1.8 (m, 7H), 2.4-2.5 (m, 1H), 3.16 (s, 3H), 5.27 (s, 2H), 7.4-7.6 (m, 5H), 7.97 (s, 1H), 12.80 (bs, 1H); MS (ES$^+$) m/z 370 (M+H)$^+$.

Step 3: 6-cyclohexyl-3-formyl-4-(methoxymethyl)-5-phenyl-4H-thieno[3,2-b]pyrrole-2-carboxylic acid A solution (0.2 M) of 6-cyclohexyl-4-(methoxymethyl)-5-phenyl-4H-thieno[3,2-b]pyrrole-2-carboxylic acid in THF was added dropwise to a solution (0.6 M) of sec-BuLi (3 eq.) and TMEDA (3 eq.) in THF at −78° C. After 5 min at −78° C., the resulting solution was treated with DMF (10 eq.) then was allowed to warm up at −10° C. The mixture was quenched with water and poured into aqueous HCl (0.1 N) and extracted with AcOEt. The combined organic phase was dried and concentrated to give the title compound (85%) as a solid, that was used as such.

$^1$H NMR (400 MHz, DMSO-d$_6$, 300 K) δ 1.2-1.3 (m, 3H), 1.6-1.8 (m, 7H), 2.4-2.5 (m, 1H), 2.92 (s, 3H), 5.45 (s, 2H), 7.4-7.5 (m, 2H), 7.5-7.6 (m, 3H), 10.73 (s, 1H); MS (ES$^+$) m/z 398 (M+H)$^+$.

Step 4: [2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl]methanaminium trifluoroacetate A solution (0.03 M) of 6-cyclohexyl-3-formyl-4-(methoxymethyl)-5-phenyl-4H-thieno[3,2-b]pyrrole-2-carboxylic acid in 1,2-dichloroethane at RT was treated with [(1,1-dioxidotetrahydro-3-thienyl)methyl]amine (1.2 eq.) and sodium triacetoxyborohydride (1.5 eq.). The mixture was stirred at RT for 2 h then quenched with aqueous NaHCO$_3$ (saturated solution), diluted with phosphate buffer (pH 5.5) and extracted with AcOEt. The combined organic phase was dried and evaporated to give a residue that was purified by RP-HPLC (Conditions: Waters X-TERRA MS C18, 10 micron, 19×150 mm; flow: 20 mL/min; Gradient: A: H$_2$O+0.05% TFA; B: MeCN+0.05% TFA; 90% A isocratic for 2 min then linear to 10% A in 9 min) to afford the title compound (32%) as a solid.

$^1$H NMR (400 MHz, DMSO-d$_6$, 300 K) δ 1.18-1.26 (m, 3H), 1.55-1.76 (m, 7H), 1.86-1.94 (m, 1H), 2.36-2.46 (m, 2H), 2.81-2.87 (m, 1H), 2.96-3.01 (m, 1H), 3.01 (s, 3H), 3.08-3.16 (m, 1H), 3.24-3.41 (m, 4H), 4.61 (bq, J=6.4 Hz, 2H), 5.26 (d, J=11.2 Hz, 1H), 5.30 (d, J=11.2 Hz, 1H), 7.38-7.62 (m, 5H), 8.86 (bs, 1H), 13.5 (bs, 1H); MS (ES$^+$) m/z 531 (M+H)$^+$.

EXAMPLE 11

3-[(benzylamino)methyl]-6-cyclohexyl-4-(methoxymethyl)-5-phenyl-4H-thieno[3,2-b]pyrrole-2-carboxylic acid Following the procedure described above for [2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl]methanaminium trifluoroacetate (step 4), treatment of a solution (0.02 M) of 6-cyclohexyl-3-formyl-4-(methoxymethyl)-5-phenyl-4H-thieno[3,2-b]pyrrole-2-carboxylic acid in 1,2-dichloroethane with benzylamine (1.2 eq.) and sodium triacetoxyborohydride (1.5 eq.) gave a residue that was purified by RP-HPLC (Conditions: Waters X-TERRA MS C18, 10 micron, 19×150 mm; flow: 20 mL/min; Gradient: A: $H_2O$+ 0.05% TFA; B: MeCN+0.05% TFA; 90% A isocratic for 2 min then linear to 10% A in 9 min) to afford the title compound (39%) as its TFA salt.

$^1$H NMR (400 MHz, DMSO-$d_6$, 300 K) δ 1.2-1.3 (m, 3H), 1.6-1.8 (m, 7H), 2.38-2.46 (m, 1H), 2.88 (s, 3H), 4.30 (bs, 2H), 4.50 (bs, 2H), 5.08 (s, 2H), 7.35-7.58 (m, 10H), 10.2 (bs, 1H), 13.6 (bs, 1H); MS (ES$^+$) m/z 589 (M+H)$^+$.

EXAMPLE 12

6-cyclohexyl-3-[(dimethylamino)methyl]-5-phenyl-4H-thieno[3,2-b]pyrrole-2-carboxylic acid Following the procedure described above for [2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl] methanaminium trifluoroacetate (step 4), treatment of a solution (0.03 M) of 6-cyclohexyl-3-formyl-4-(methoxymethyl)-5-phenyl-4H-thieno[3,2-b]pyrrole-2-carboxylic acid in 1,2-dichloroethane with dimethylamine (2 M solution in THF, 1.2 eq.) and sodium triacetoxyborohydride (1.5 eq.) gave a residue that was dissolved in THF. The resulting solution (0.1 M) was treated with aqueous of HCl (1 N, 8 eq.) and the mixture was heated to 60° C. for 26 h. After cooling down, the mixture was concentrated to give a residue that was purified by RP-HPLC (Conditions: Waters X-TERRA MS C18, 10 micron, 19×150 mm; flow: 20 mL/min; Gradient: A: $H_2O$+ 0.05% TFA; B: MeCN+0.05% TFA; 90% A isocratic for 2 min then linear to 10% A in 9 min) to afford the title compound (29%) as its TFA salt.

$^1$H NMR (400 MHz, DMSO-$d_6$, 300 K) δ 1.2-1.4 (m, 3H), 1.6-1.9 (m, 7H), 2.8 (bs, 7H), 4.64 (s, 2H), 7.4-7.6 (m, 5H), 10.1 (bs, 1H), 11.70 (s, 1H), 13.4 (bs, 1H); MS (ES$^+$) m/z 383 (M+H)$^+$.

EXAMPLE 13

5-(4-chlorophenyl)-6-cyclohexyl-3-[(isobutylamino) methyl]-4-{2-[(1-isopropylpyrrolidin-3-yl)(methyl) amino]-2-oxoethyl}-4H-thieno[3,2-b]pyrrole-2-carboxylic acid Step 1: methyl 5-[(E)-2-(4-chlorophenyl)vinyl]4-nitrothiophene-2-carboxylate A solution (1.74 M) of methyl 5-methyl-4-nitrothiophene-2-carboxylate (prepared as described in example 1, step 1) in MeOH, was treated with 4-chlorobenzaldehyde (1.5 eq.). The reaction mixture was heated to reflux and when it became a clear solution, a catalytic amount of pyrrolidine (0.10 eq.) was added. The reaction mixture was heated to reflux overnight. After cooling down, evaporation of the solvent gave a residue that was triturated with petroleum ether/$Et_2O$ and filtered to afford the title compound title compound (67%) as a solid.

$^1$H NMR (400 MHz, acetone-$d_6$, 300 K) δ 3.94 (s, 3H), 7.50-7.59 (m, 3H), 7.74-7.79 (m, 2H), 8.09-8.12 (m, 2H).

Step 2: methyl 5-(4-chlorophenyl)-4H-thieno[3,2-b]pyrrole-2-carboxylate

A solution (1 M) of methyl 5-[(E)-2-(4-chlorophenyl)vinyl]-4-nitrothiophene-2-carboxylate in triethyl phosphite was heated to reflux for 20 h. After cooling down a part of the solvent was evaporated under high vacuum (2 mbar, water bath 60° C.) then the residue was purified by flash chromatography on silica gel (1:20 acetone/toluene). Fractions containing the title compound along with some phosphorous impurities were concentrated to give a residue that was triturated with AcOEt/petroleum ether (1:9) and filtered to afford the title compound (16%) as a solid.

$^1$H NMR (300 MHz, CDCl$_3$, 300 K) δ 3.88 (s, 3H), 6.72 (s, 1H), 7.38 (d, J=8.5 Hz, 2H), 7.49 (d, J=8.5 Hz, 2H), 7.68 (s, 1H), 8.51 (bs, 1H).

Step 3: methyl 5-(4-chlorophenyl)-6-cyclohex-1-en-1-yl-4H-thieno[3,2-b]pyrrole-2-carboxylate A solution (0.2 M) of methyl 5-(4-chlorophenyl)-4H-thieno[3,2-b]pyrrole-2-carboxylate in acetic acid was treated with acetic anhydride (2.5 eq.), cyclohexanone (10 eq.) and 85% phosphoric acid (2.1 eq.). The mixture was heated at 80° C. for 3.5 days. After cooling down it was poured into ice cold ammonium hydroxide. The product was extracted with AcOEt and the combined organic layers were washed sequentially with aqueous HCl (1 N), aqueous NaHCO, (saturated solution) and brine then dried and concentrated. The crude was purified by flash chromatography on silica gel (1:9 to 1:4 AcOEt/petroleum ether) affording the title compound (91%) as a solid.

$^1$H NMR (400 MHz, CDCl$_3$, 300 K) δ 1.66 (m, 4H) 2.15 (m, 4H), 3.88 (s, 3H), 5.91 (bs, 1H), 7.36 (d, J=8.6 Hz, 2H), 7.44 (d, J=8.6 Hz, 2H), 7.64 (s, 1H), 8.17 (bs, 1H); MS (ES$^+$) m/z 372, 374 (M+H)$^+$.

Step 4: methyl 5-(4-chlorophenyl)-6-cyclohexyl-4H-thieno[3,2-b]pyrrole-2-carboxylate A solution (0.11 M) of methyl 5-(4-chlorophenyl)-6-cyclohex-1-en-1-yl-4H-thieno[3,2-b]pyrrole-2-carboxylate in TFA at 0° C. was treated with triethylsilane (1.5 eq.). The reaction mixture was stirred at 0° C. for 2 h then solvent was evaporated to give the title compound (99%) as a solid.

$^1$H NMR (300 MHz, CDCl$_3$, 300 K) δ 1.32 (m, 3H), 1.85 (m, 7H), 2.76 (m, 1H), 3.88 (s, 3H), 7.36 (d, J=8.4 Hz, 2H), 7.43 (d, J=8.4 Hz, 2H), 7.66 (s, 1H), 8.09 (bs, 1H); MS (ES$^+$) m/z 374, 376 (M+H)$^+$.

Step 5: 5-(4-chlorophenyl)-6-cyclohexyl-4-(methoxymethyl)-4H-thieno[3,2-b]pyrrole-2-carboxylic acid A solution (0.20 M) of methyl 5-(4-chlorophenyl)-6-cyclohexyl-4H-thieno[3,2-b]pyrrole-2-carboxylate in DMF was treated at 0° C. with NaH (1.5 eq., 60% dispersion in mineral oil), and the suspension was stirred at RT for 45 min then cooled again to 0° C., and treated with chloromethyl methyl ether (5 eq.). The reaction mixture was stirred at RT for 1.5 h then was cooled at 0° C. and quenched with aqueous NaHCO$_3$ (saturated solution) and extracted with AcOEt. The combined organic phase was washed with brine and dried. Evaporation of the solvent under reduced pressure gave a residue that was purified by flash chromatography on silica gel (1:9 acetone/toluene) to afford methyl 5-(4-chlorophenyl)-6-cyclohexyl-4-(methoxymethyl)-4H-thieno[3,2-b]pyrrole-2-carboxylate (100%). This compound was dissolved in THF/MeOH (2:3), and the resulting solution (0.08 M) was treated at RT with aqueous NaOH (2N solution, 5 eq.). The mixture was heated at 85° C. for 1.5 h. After cooling down, the reaction mixture was concentrated and acidified to pH 1 with aqueous HCl (1 N) and extracted with AcOEt. The combined organic phase was washed with brine and dried. Evaporation of the solvent under reduced pressure afforded the title compound (96%) as a solid.

¹H NMR (400 MHz, DMSO-d₆, 300 K) δ 1.17-1.21 (m, 3H), 1.60-1.74 (m, 7H), 2.41-2.50 (m, 1H), 3.13 (s, 3H), 5.23 (s, 2H), 7.45 (d, J=7.4 Hz, 2H), 7.58 (d, J=7.4 Hz, 2H), 7.95 (s, 1H), 12.80 (bs, 1H); MS (ES⁺) m/z 404, 406 (M+H)⁺.

Step 6: methyl 5-(4-chlorophenyl)-6-cyclohexyl-3-formyl-4-(methoxymethyl)-4H-thieno[3,2-b]pyrrole-2-carboxylate A solution (0.27 M) of 5-(4-chlorophenyl)-6-cyclohexyl-4-(methoxymethyl)-4H-thieno[3,2-b]pyrrole-2-carboxylic acid in THF was added dropwise to a solution of n-BuLi (3 eq.) and TMEDA (3 eq.) in THF (50 mL) at −78° C. The reaction mixture was stirred at −78° C. for 1.5 h then the resulting solution was treated with DMF (10 eq.). The mixture was stirred at −78° C. for 2 h, then quenched with aqueous NH₄Cl (saturated solution), quickly diluted with AcOEt and poured into aqueous HCl (1 N). The aqueous layer was separated and extracted with AcOEt. The combined organic phase was dried and concentrated under vacuum. The resulting residue was azeotropically dried by co-evaporation with toluene, giving a crude that was dissolved in DMF. The resulting solution (0.22 M) was treated with K₂CO₃ (1.5 eq.) and MeI (5 eq.). The mixture was stirred at RT overnight then diluted with AcOEt and washed with water and brine. Evaporation of the solvent under reduced pressure afforded a residue that was purified by flash chromatography on silica gel (1:9 AcOEt/petroleum ether and AcOEt) to afford the title compound (72%) as a solid.

¹H NMR (400 MHz, acetone-d₆, 300 K) δ 1.26-1.32 (m, 3H), 1.67-1.80 (m, 7H), 2.55 (m, 1H), 2.98 (s, 3H), 3.07 (s, 3H), 5.52 (s, 2H), 7.51 (d, J=8.6 Hz, 2H), 7.58 (d, J=8.6 Hz, 2H), 10.76 (s, 1H); MS (ES⁺) m/z 468, 470 (M+H)⁺.

Step 7: methyl 5-(4-chlorophenyl)-6-cyclohexyl-3-formyl-4H-thieno[3,2-b]pyrrole-2-carboxylate A solution (0.11 M) of methyl 5-(4-chlorophenyl)-6-cyclohexyl-3-formyl-4-(methoxymethyl)-4H-thieno[3,2-b]pyrrole-2-carboxylate in dioxane/aqueous HCl (6 N) (1:1) was heated at 130° C. under microwave irradiation for 10 min. After dilution with AcOEt, the resulting solution was basified with solid NaHCO₃ and extracted with AcOEt. The combined organic phase was washed with brine, dried and concentrated under reduced pressure. The crude was triturated with Et₂O/petroleum ether (1:9) to afford the title compound (70%) as a solid.

¹H NMR (400 MHz, DMSO-d₆, 300 K) δ 1.26-1.32 (m, 3H), 1.60-1.80 (m, 7H), 2.72 (m, 1H), 3.91 (s, 3H), 7.52-7.55 (m, 4H), 10.62 (s, 1H), 11.84 (s, 1H); MS (ES⁺) m/z 402, 404 (M+H)⁺.

Step 8: methyl 5-(4-chlorophenyl)-6-cyclohexyl-3-(1,3-dioxolan-2-yl)-4-methyl-4H-thieno[3,2-b]pyrrole-2-carboxylate A solution (0.15 M) of methyl 5-(4-chlorophenyl)-6-cyclohexyl-3-formyl-4H-thieno[3,2-b]pyrrole-2-carboxylate, ethylene glycol (10 eq.) and a catalytic amount of p-TsOH in toluene was refluxed (Dean-Stark) for 3 h. After cooling down to RT solid NaHCO₃ was added and the mixture was diluted with AcOEt and water. The layers were separated and the aqueous layer was extracted with AcOEt. The combined organic phase was dried. Evaporation of the solvent under reduced pressure afforded a residue that was purified by flash chromatography on silica gel (1:3 AcOEt/petroleum ether) to afford the title compound (89%) as a yellow solid.

¹H NMR (400 MHz, CDCl₃, 300 K) δ 1.26-1.32 (m, 3H), 1.65-1.80 (m, 7H), 2.72 (m, 1H), 3.88 (s, 3H), 4.10-4.17 (m, 4H), 6.53 (s, 1H), 7.36 (d, J=8.3 Hz, 2H), 7.42 (d, J=8.3 Hz, 2H), 8.49 (s, 1H); MS (ES⁺) m/z 446, 448 (M+H)⁺.

Step 9: [5-(4-chlorophenyl)-6-cyclohexyl-3-formyl-2-(methoxycarbonyl)-4H-thieno[3,2-b]pyrrol-4-yl]acetic acid A solution (0.23 M) of methyl 5-(4-chlorophenyl)-6-cyclohexyl-3-(1,3-dioxolan-2-yl)-4-methyl-4H-thieno[3,2-b]pyrrole-2-carboxylate in DMF at 0° C. was treated with NaH (2 eq., 60% dispersion in mineral oil), and the suspension was stirred at RT for 30 min, then tert-butyl bromoacetate (4 eq.) was added. The reaction mixture was heated at 50° C. for 3.5 h then it was quenched by addition of aqueous NH₄Cl (saturated solution) and diluted with Et₂O. The aqueous phase was separated and extracted with Et₂O. The combined organic phase was washed sequentially with aqueous HCl (1 N), aqueous NaHCO₃ (saturated solution) and brine then dried and evaporated. The residue was purified by flash chromatography on silica gel (1:19 to 1:1 AcOEt/petroleum ether) to afford methyl 4-(2-tert-butoxy-2-oxoethyl)-5-(4-chlorophenyl)-6-cyclohexyl-3-(1,3-dioxolan-2-yl)-4H-thieno[3,2-b]pyrrole-2-carboxylate. This compound was dissolved in DCM and the resulting solution (0.1 M) was treated with TFA (16 eq.). The reaction was stirred at RT for 3 h then solvents were evaporated under reduced pressure and the residue was purified by flash chromatography on silica gel (1:99 to 1:19 MeOH/DCM) to afford the title compound (55%).

¹H NMR (400 MHz, CDCl₃, 300 K) δ 1.20-1.25 (m, 3H), 1.63-1.75 (m, 7H), 2.35 (m, 1H), 3.92 (s; 3H), 4.90 (bs, 2H), 7.22 (d, J=8.1 Hz, 2H), 7.41 (d, J=8.1 Hz, 2H), 10.68 (s, 1H).

Step 10: methyl 5-(4-chlorophenyl)-6-cyclohexyl-3-formyl-4-{2-[(1-isopropylpyrrolidin-3-yl)(methyl)amino]-2-oxoethyl}-4H-thieno[3,2-b]pyrrole-2-carboxylate A solution (0.13 M) of [5-(4-chlorophenyl)-6-cyclohexyl-3-formyl-2-(methoxycarbonyl)-4H-thieno[3,2-b]pyrrol-4-yl]acetic acid in DMF was treated with DIEA (3 eq.), HATU (1.5 eq.) and a solution (0.5 M) of 1-isopropyl-N-methylpyrrolidin-3-amine (1.5 eq.) in DMF. The reaction mixture was stirred at RT for 3 h. The reaction was quenched with aqueous NaHCO₃ (saturated solution) and extracted with AcOEt. The combined organic phase was washed with brine and dried. Evaporation under reduced pressure gave a residue that was purified by flash chromatography on silica gel (1:49 Et₃N/AcOEt) to afford the title compound (62%) as a solid.

¹H NMR (400 MHz, DMSO-d₆, 300 K) 3 rotamers 2:1.5*: 1, δ 1.00 (bs, 6H), 1.17-1.23 (m, 3H), 1.50-1.74 (m, 8H), 2.00 (m, 1H), 2.10-2.50 (m, 5H), 2.50 (m, 1H), 2.73-2.86 (m, 1H), 2.73, 2.79*, 2.89 (s, 3H), 3.90 (s, 3H), 4.85**, 4.95, 5.10*(m, 2H), 7.29-7.32 (m, 2H), 7.57-7.59 (m, 2H), 10.53 (s, 1H); MS (ES⁺) m/z 584, 586 (M+H)⁺.

Step 11: 5-(4-chlorophenyl)-6-cyclohexyl-3-[(isobutylamino)methyl]-4-{2-[(1-isopropylpyrrolidin-3-yl)(methyl)amino]-2-oxoethyl}-4H-thieno[3,2-h]-pyrrole-2-carboxylic acid A solution (0.08 M) of methyl 5-(4-chlorophenyl)-6-cyclohexyl-3-formyl-4-{2-[(1-isopropylpyrrolidin-3-yl)(methyl)amino]-2-oxoethyl}-4H-thieno[3,2-b]pyrrole-2-carboxylate in MeOH was treated with isobutylamine (6 eq.) and stirred at RT for 15 min. After addition of ZnCl₂ (1.2 eq.) and NaBH₃CN (2.5 eq.) the pH was adjusted to 5 with methanolic HCl (1.25 M solution), then the reaction mixture was stirred for at RT for 2.5 days. After quenching with aqueous HCl (6 N), solvents were removed under reduced pressure. The resulting residue was treated with aqueous NaHCO₃ (saturated solution) and the mixture was extracted with DCM. The combined organic phase was dried and solvent was evaporated giving a crude that was dissolved in MeOH/THF (2:1). The resulting solution (0.05 M) was treated with aqueous KOH (1 N solution, 3 eq.) and heated to 50° C. for 3 h. After cooling down, solvents were evaporated under reduced pressure and the residue was purified by RP-HPLC (Conditions: Waters X-TERRA MS C18, 5 micron, 19×150 mm; flow: 20 mL/min; Gradient: A: H$_2$O+0.1% TFA; B: MeCN+0.1% TFA; 90% A isocratic for 1 min, linear to 50% A in 4 min, linear to 40% A in 1 min, 40% A isocratic for 1 min, linear to 30% A in 1 min, 30% A isocratic for 2 min, linear to 0% A in 5 min) to afford the title compound (31%) as its TFA salt.

$^1$H NMR (600 MHz, DMSO-d$_6$, 300 K) mixture of rotamers, δ 0.96-0.99 (m, 6H), 1.13-1.16 (m, 9H), 1.54-1.74 (m, 8H), 2.35-2.42 (m, 1H), 2.77*, 2.80 (s, 3H), 2.81 (m, 1H), 2.89-2.96 (m, 2H), 3.00-3.10 (m, 1H), 3.28-3.50 (m, 3H), 3.55-3.60, 3.60-3.67* (m, 1H), 4.37-4.46 (m, 2H), 4.83-4.98 (m, 3H), 7.26 (d, J=8.3 Hz, 2H), 7.63 (d, J=8.3 Hz, 2H), 8.51 (bs, 2H), 9.80, 9.88*, 10.16** (s, 1H); MS (ES$^+$) m/z 627, 629 (M+H)$^+$.

EXAMPLE 14

5-(4-chlorophenyl)-6-cyclohexyl-)-4K-thieno[3,2-b]pyrrole-2-carboxylic acid

Step 1: ethyl 4-nitrothiophene-2-carboxylate

A solution of nitric acid/sulfuric acid (1:2.5) was added dropwise to a stirred solution (2.7 M) of ethyl 2-thiophene carboxylate in sulfuric acid at −10° C. After stirring for an additional half an hour, the reaction mixture was poured into ice-water. The resulting precipitate was filtered, washed with water and dried to give the title compound (96%) as a mixture 1:1 of 4-nitro and 5-nitro regioisomers.

$^1$H NMR (300 MHz, DMSO-d$_6$, 300 K) δ 1.3-1.4 (m, 6H), 4.3-4.4 (m, 4H), 7.84 (d, J=4.21 Hz, 1H), 8.74 (d, J=4.20 Hz, 1H), 8.21 (d, J=1.77 Hz, 1H), 9.08 (d, J=1.77 Hz, 1H); MS (ES$^+$) m/z 202 (M+H)$^+$.

Step 2: ethyl 4-(acetylamino)thiophene-2-carboxylate

A solution (0.3 M) of the foregoing compound in a mixture of acetic acid/acetic anhydride (8:1) was treated with granulated iron (3.5 eq) then the mixture was heated to 90° C. for 18 h. After cooling down, it was quenched with ice, filtered through a pad of celite and washed with AcOEt. The filtrate was washed sequentially with aqueous NaHCO$_3$ (saturated solution) and brine then dried. Evaporation of the solvent under reduced pressure afforded the title compound (86%) as a mixture 1:1 of 4 acetylamino and 5-acetylamino regioisomers that was used as such in the following step.

$^1$H NMR (300 MHz, DMSO-d$_6$, 300 K) δ 1.3-1.4 (m, 6H), 2.06 (s, 3H), 2.15 (s, 3H), 4.24-4.35 (m, 4H), 6.69 (d, J=4.20 Hz, 1H), 7.61 (d, J=4.20 Hz, 1H), 7.80 (s, 2H), 10.44 (bs, 1H), 11.65 (bs, 1H); MS (ES$^+$) m/z 214 (M+H)$^+$.

Step 3: ethyl 4-[(tert-butoxycarbonyl)amino]thiophene-2-carboxylate

A solution (0.2 M) of ethyl 4-(acetylamino)thiophene-2-carboxylate in DCM was treated with Boc$_2$O (1.2 eq.), Et$_3$N (1.5 eq.) and DMAP (0.1 eq.). The solution was stirred at RT for 24 h. The solvent was partially evaporated, then the residue was diluted with AcOEt and washed sequentially with aqueous HCl (1 N), aqueous NaHCO$_3$ (saturated solution) and brine. The organic phase was separated and dried then concentrated to give an oil that was dissolved in EtOH. The resulting solution (0.2 M) was treated with aqueous hydrazine (1.5 eq., 35% solution) then heated to reflux for 3 h. After cooling down, evaporation of the solvent gave a residue which was dissolved in AcOEt then washed sequentially with aqueous HCl (1 N), aqueous NaHCO$_3$ (saturated solution) and brine. The organic phase was separated and dried then concentrated to afford the title compound (66%) as a mixture 1:1 of 4-(tertbutoxycarbonyl)amino and 5-(tert-butoxycarbonyl)amino regioisomers that was used as such in the following step.

$^1$H NMR (300 MHz, DMSO-d$_6$, 300 K) δ 1.28-1.35 (m, 6H), 1.51 (s, 9H), 1.53 (s, 9H), 4.24-4.34 (m, 4H), 6.58 (d, J=3.9 Hz, 1H), 7.54-7.57 (m, 2H), 7.70 (s, 1H), 9.82 (bs, 1H), 11.01 (bs, 1H); MS (ES$^+$) m/z 272 (M+H)$^+$.

Step 4: ethyl 5-bromo-4-[(tert-butoxycarbonyl)amino]thiophene-2-carboxylate

A solution (0.2 M) of ethyl 4-[(tert-butoxycarbonyl)amino]thiophene-2-carboxylate in DCM was cooled to 0° C. and treated with NBS (1.1 eq.) then stirred at 0° C. for 30 min. The mixture was quenched with aqueous Na$_2$S$_2$O$_3$ (saturated solution) and extracted with AcOEt. The organic phase was washed with aqueous Na$_2$S$_2$O$_3$ (saturated solution) and brine then dried and concentrated. The residue was purified by flash chromatography on silica gel (1:12 AcOEt/petroleum ether) to afford the title compound (48%) as a solid. $^1$H NMR (300 MHz, DMSO-d, 300 K) δ 1.32 (t, J=7.07 Hz, 3H), 1.50 (s, 9H), 4.32 (q, J=7.07 Hz, 2H), 7.81 (s, 1H), 9.13 (bs, 1H); MS (ES$^+$) m/z 350, 352 (M+H)$^+$;

along with ethyl 4-bromo-5-[(tert-butoxycarbonyl)amino]thiophene-2-carboxylate (47%). $^1$H NMR (400 MHz, DMSO-d$_6$, 300 K) δ 1.29 (t, J=7.20 Hz, 3H), 1.47 (s, 9H), 4.26 (q, J=7.20 Hz, 2H), 7.59 (s, 1H), 10.31 (bs, 1H); MS (ES$^+$) m/z 350, 352 (M+H)$^+$.

Step 5: ethyl 4-[(tert-butoxycarbonyl)amino]-5-[(trimethylsilyl)ethynyl]thiophene-2-carboxylate A solution (0.1 M) of ethyl 5-bromo-4-[(tert-butoxycarbonyl)amino]thiophene-2-carboxylate in THF was treated with trimethylsilylacetylene (1.3 eq.), Et$_3$N (1.5 eq.), CuI (0.04 eq.) and PdCl$_2$(PPh$_3$)$_2$ (0.01 eq.). The solution was heated at 50° C. for 3 h. After cooling down, it was filtered through a pad of celite and washed with AcOEt. The organic layer was washed with brine and dried then concentrated and the residue was purified by flash chromatography on silica gel (1:19 AcOEt/petroleum ether) to afford the title compound (70%) as a solid.

$^1$H NMR (300 MHz, DMSO-d$_6$, 300 K) δ 0.28 (s, 9H), 1.32 (t, J=7.07 Hz, 3H), 1.51 (s, 9H), 4.33 (q, J=7.07 Hz, 2H), 7.88 (s, 1H), 9.29 (s, 1H); MS (ES$^+$) m/z 368 (M+H)$^+$.

Step 6: ethyl 4H-thieno[3,2-b]pyrrole-2-carboxylate

A solution (0.3 M) of ethyl 4-[(tert-butoxycarbonyl)amino]-5-[(trimethylsilyl)ethynyl]thiophene-2-carboxylate in THF was treated with n-Bu$_4$NF (2 eq.). The mixture was irradiated in a microwave apparatus at 120° C. for 20 min. Evaporation of the solvent gave a residue that was purified by flash chromatography on silica gel (1:3 AcOEt/petroleum ether) to afford the title compound (94%) as a solid.

$^1$H NMR (300 MHz, DMSO-d$_6$, 300 K) δ 1.33 (t, J=7.07 Hz, 3H), 4.30 (q, J=7.07 Hz, 2H), 6.47 (m, 1H), 7.39 (m, 1H), 7.73 (m, 1H), 11.52 (s, 1H); MS (ES$^+$) m/z 196 (M+H)$^+$.

Step 7: 6-cyclohex-1-en-1-yl-4H-thieno[3,2-b]pyrrole-2-carboxylic acid

A solution (0.25 M) of ethyl 4H-thieno[3,2-b]pyrrole-2-carboxylate in EtOH was treated with cyclohexanone (2 eq.) and sodium ethoxide (2.05 eq.) then heated to reflux for 4 h. After cooling down, it was acidified with aqueous HCl (6 N) and the precipitate was filtered and dried, affording the title compound (98%) as a solid.

$^1$H NMR (300 MHz, DMSO-d$_6$, 300 K) δ 1.7-1.8 (m, 4H), 2.2-2.5 (m, 4H), 5.85 (bs, 1H), 7.39 (d, J=2.66 Hz, 1H), 7.67 (s, 1H), 11.45 (s, 1H); MS (ES$^+$) m/z 248 (M+H)$^+$.

Step 8: 6-cyclohexyl-4H-thieno[3,2-b]pyrrole-2-carboxylic acid

A solution (0.1 M) of 6-cyclohex-1-en-1-yl-4H-thieno[3,2-b]pyrrole-2-carboxylic acid in MeOH/AcOEt (2:1) was treated with 20% Pd(OH)$_2$/C (10% wt.). The resulting suspension was stirred for 18 h under 45 psi of hydrogen then purged with nitrogen and filtered. The filtrate was concentrated to afford the title compound (98%) as a solid.

$^1$H NMR (300 MHz, DMSO-d$_6$, 300 K) δ 1.2-2.2 (m, 10H), 2.61 (m, 1H), 7.12 (d, J=2.21 Hz, 1H), 7.62 (s, 1H), 11.18 (s, 1H), 12.63 (bs, 1H); MS (ES$^+$) m/z 250 (M+H)$^+$.

Step 9: methyl 4-(tert-butoxycarbonyl)-6-cyclohexyl-4H-thieno[3,2-b]pyrrole-2-carboxylate A solution (0.2 M) of 6-cyclohexyl-4H-thieno[3,2-b]pyrrole-2-carboxylic acid in DCM was treated with Boc$_2$O (1.1 eq.), Et$_3$N (1.1 eq.) and DMAP (0.1 eq.). The solution was stirred at RT for 24 h. The mixture was diluted with AcOEt then washed sequentially with aqueous HCl (1 N), aqueous NaHCO$_3$ (saturated solution) and brine. The organic phase was separated and dried the concentrated to give a solid that was dissolved in MeOH. The resulting solution (0.2 M) was cooled to 0° C. then treated with trimethylsilyldiazomethane (5 eq.). The reaction was stirred at RT for 18 h. Evaporation of the solvent gave a residue that was purified by flash chromatography on silica gel (1:5 AcOEt/petroleum ether) to afford the title compound (63%) as a solid.

$^1$H NMR (300 MHz, DMSO-d$_6$, 300 K) δ 1.2-2.2 (m, 10H), 1.62 (s, 9H), 2.61 (m, 1H), 3.87 (s, 3H), 7.48 (s, 1H), 7.89 (s, 1H).

Step 10: methyl 5-bromo-4-(tert-butoxycarbonyl)-6-cyclohexyl-4H-thieno[3,2-b]pyrrole-2-carboxylate A solution (0.1 M) of methyl 4-(tert-butoxycarbonyl)-6-cyclohexyl-4H-thieno[3,2-b]pyrrole-2-carboxylate in DCM was cooled to 0° C. and treated with NBS (1.1 eq.) then it was left to warm to RT. The reaction was quenched with aqueous Na$_2$S$_2$O$_3$ (saturated solution) and extracted with AcOEt. The organic phase was washed with aqueous Na$_2$S$_2$O$_3$ (saturated solution) and brine then dried and concentrated, affording the title compound (98%) as a solid.

$^1$H NMR (400 MHz, DMSO-d$_6$, 300 K) δ 1.2-1.8 (m, 10H), 1.66 (s, 9H), 2.74 (m, 1H), 3.85 (s, 3H), 7.87 (s, 1H); MS (ES$^+$) m/z 443, 445 (M+H)$^+$.

Step 11: methyl 4-(tert-butoxycarbonyl)-5-(4-chlorophenyl)-6-cyclohexyl-4H-thieno[3,2-b]pyrrole-2-carboxylate A solution (0.1 M) of methyl 5-bromo-4-(tert-butoxycarbonyl)-6-cyclohexyl-4H-thieno[3,2-b]pyrrole-2-carboxylate in EtOH/toluene (1:1) was treated with 4-chlorophenylboronic acid (1.3 eq.) and LiCl (2 eq.). Aqueous Na$_2$CO$_3$ (2 N, 2.5 eq.) was added and the solution was degassed, then Pd(PPh$_3$)$_4$ (0.1 eq.) was added. The mixture was heated to 80° C. for 18 h, then cooled and diluted with AcOEt. The organic phase was washed sequentially with water, aqueous HCl (1 N) and brine, then dried and concentrated giving a residue that was purified by flash chromatography on silica gel (1:9 AcOEt/petroleum ether) to afford the title compound (69%) as a solid.

$^1$H NMR (300 MHz, DMSO-d$_6$, 300 K) δ 1.3-1.8 (m, 10H), 1.32 (s, 9H), 3.89 (s, 3H), 7.45 (d, J=8.4 Hz, 2H), 7.57 (d, J=8.2 Hz, 2H), 8.02 (s, 1H); MS (ES$^+$) m/z 475, 477 (M+H)$^+$.

Step 12: 5-(4-chlorophenyl)-6-cyclohexyl-4H-thieno[3,2-b]pyrrole-2-carboxylic acid A solution (0.5 M) of methyl 4-(tert-butoxycarbonyl)-5-(4-chlorophenyl)-6-cyclohexyl-4H-thieno[3,2-b]pyrrole-2-carboxylate in DCM/TFA (1:1) was stirred at RT for 1 h. Evaporation of the solvent gave a solid that was dissolved in MeOH. The resulting solution (0.1N) was treated with aqueous NaOH (1 N solution, 12 eq.). The mixture was heated to reflux for 3 h then concentrated and acidified to pH 1 with aqueous HCl (1 N), the aqueous solution was diluted with MeCN and purified by RP-HPLC (Conditions: Waters X-TERRA MS C18, 5 micron, 19×150 mm; flow: 15 mL/min; Gradient: A: H$_2$O+0.05% TFA; B: MeCN+0.05% TFA; 60% A isocratic for 2 min then linear to 0% A in 10 min) to afford the title compound (53%) as a solid.

$^1$H NMR (400 MHz, DMSO-d$_6$, 300 K) δ 1.25-1.36 (m, 4H), 1.62-1.79 (m, 6H), 2.78 (m, 1H), 7.50-7.58 (m, 5H), 11.60 (s, 1H); MS (ES$^+$) m/z 360, 362 (M+H)$^+$.

EXAMPLE 15

5-(4-chlorophenyl)-6-cyclohexyl-4-[2-(dimethylamino)-2-oxoethyl]-4H-thieno[3,2-b]pyrrole-2-carboxylic acid A solution (0.5 M) of methyl 4-(tert-butoxycarbonyl)-5-(4-chlorophenyl)-6-cyclohexyl-4H-thieno[3,2b]pyrrole-2-carboxylate in DCM/TFA (1:1) was stirred at RT for 1 h. Evaporation of the solvent gave a solid that was dissolved in DMF. The resulting solution (0.1N) was cooled to 0° C. and treated with NaH (2 eq., 60% dispersion in mineral oil). The mixture was stirred at RT for 30 min then treated with 2-chloro-N,N-dimethylacetamide (3 eq.) and heated to 50° C. for 1 h. After cooling down, it was diluted with AcOEt then washed sequentially with aqueous HCl (1 N), aqueous NaHCO$_3$ (saturated solution), water and brine. The organic phase was separated and dried, then concentrated to give a solid that was dissolved in DCM. The resulting solution (0.1 M) was treated dropwise with BBr$_3$ (3 eq.) then stirred at RT for 1 h. After treatment with an additional quantity of BBr$_3$ (3 eq.) the mixture was stirred at RT for 18 h then concentrated under reduced pressure and the residue was purified by RP-HPLC (Conditions: Waters X-TERRA MS C18, 10 micron, 19×150 mm; flow: 20 mL/min; Gradient: A: H$_2$O+0.05% TFA; B: MeCN+0.05% TFA; 60% A isocratic for 2 min then linear to 0% A in 8 min) to afford the title compound (49%) as a solid.

$^1$H NMR (400 MHz, DMSO-d$_6$, 300 K) δ 1.2-1.4 (m, 3H), 1.5-1.8 (m, 7H), 2.4 (m, 1H), 2.80 (s, 3H), 2.90 (s, 3H), 4.83 (s, 2H), 7.32 (d, J=8.06 Hz, 2H), 7.56 (d, J=8.06 Hz, 2H), 7.77 (s, 1H); MS (ES$^+$) m/z 445, 447 (M+H)$^+$.

EXAMPLE 16 methyl 5-(4-chlorophenyl)-6-cyclohexyl-4-(2-morpholin-4-yl-2-oxoethyl)$_{49}$-thieno[3,2-b]pyrrole-2-carboxylate Step 1: methyl 4-(2-tert-butoxy-2-oxoethyl)-6-cyclohexyl-5-(4-chlorophenyl)-4H-thieno[3,2-b]pyrrole-2-carboxylate A solution (0.2 M) of methyl 5-(4-chlorophenyl)-6-cyclohexyl-4H-thieno[3,2-b]pyrrole-2-carboxylate (prepared as described in example 13, step 4) in DMF was treated with NaH (2 eq., 60% dispersion in mineral oil), and the suspension was stirred at RT for 30 min, then tert-butyl bromoacetate (3 eq.) was added. The reaction mixture was heated at 50° C. for 2 h then cooled down and diluted with AcOEt. The organic phase was washed sequentially with aqueous HCl (1 N), aqueous NaHCO$_3$ (saturated solution) and brine and dried. Evaporation of the solvent gave a residue that was purified by flash chromatography on silica gel (1:9 AcOEt/petroleum ether) to afford the title compound (93%).

¹H NMR (300 MHz, DMSO-d₆, 300 K) δ 1.15-1.30 (m, 3H), 1.32 (s, 9H), 1.56-1.82 (m, 7H), 2.48 (m, 1H), 3.86 (s, 3H), 4.80 (s, 2H), 7.38 (d, J=8.4 Hz, 2H), 7.62 (d, J=8.4 Hz, 2H), 8.02 (s, 1H); MS (ES⁺) m/z 489, 491 (M+H)⁺.

Step 2: [5-(4-chlorophenyl)-6-cyclohexyl-2-(methoxycarbonyl)-5-phenyl-4H-thieno[3,2-b]pyrrol-4-yl]acetic acid A solution (0.04 M) of methyl 4-(2-tert-butoxy-2-oxoethyl)-6-cyclohexyl-5-(4-chlorophenyl)-4H-thieno[3,2-b]pyrrole-2-carboxylate in DCM/TFA (1:1) was stirred at RT for 3 h. Evaporation of the solvent gave the title compound (94%) as a solid.

¹H NMR (300 MHz, DMSO-d₆, 300 K) δ 1.15-1.30 (m, 3H), 1.35-1.50 (m, 7H), 2.60 (m, 1H), 4.03 (s, 3H), 4.96 (s, 2H), 7.55 (d, J=8.4 Hz, 2H), 7.80 (d, J=8.4 Hz, 2H), 8.16 (s, 1H); MS (ES⁺) m/z 432, 434 (M+H)⁺.

Step 3: methyl 5-(4-chlorophenyl)-6-cyclohexyl-4-(2-morpholin-4-yl-2-oxoethyl)-4H-thieno[3,2-b]pyrrole-2-carboxylate A solution (0.05 M) of [5-(4-chlorophenyl)-6-cyclohexyl-2-(methoxycarbonyl)-4H-thieno[3,2-b]pyrrol-4-yl]acetic acid in DMF at RT was treated with morpholine (2 eq.), DIEA (1.5 eq.) and HATU (2.5 eq.). The mixture was stirred at RT for 8 h, then it was diluted with DCM and washed sequentially with aqueous HCl (1 N), aqueous NaHCO₃ (saturated solution) and dried. Evaporation of the solvent under reduced pressure gave a residue which was purified by RP-HPLC (Conditions: Waters X-TERRA MS C18, 10 micron, 19×150 mm; flow: 20 mL/min; Gradient: A: H₂O+0.05% TFA; B: MeCN+0.05% TFA; 90% A isocratic for 2 min then linear to 10% A in 9 min) to afford the title compound (51%) as a solid.

¹H NMR (400 MHz, DMSO-d₆, 300 K) δ 1.1-1.3 (m, 3H), 1.5-1.8 (m, 7H), 2.43 (m, 1H), 3.3-3.6 (m, 8H), 3.83 (s, 3H), 4.90 (s, 2H), 7.32 (d, J=8.0 Hz, 2H), 7.59 (d, J=8.0 Hz, 2H), 7.90 (s, 1H); MS (ES⁺) m/z 501, 503 (M+H)⁺.

EXAMPLE 17

5-(4-chlorophenyl)-6-cyclohexyl-4-(2-morpholin-4-yl-2-oxoethyl)-4H-thieno[3,2-b]pyrrole-2-carboxylic acid A solution (0.1 M) of methyl 5-(4-chlorophenyl)-6-cyclohexyl-4-(2-morpholin-4-yl-2-oxoethyl)-4H-thieno[3,2-b]pyrrole-2-carboxylate was treated with BBr₃ (4 eq.) and the mixture was stirred at RT. After 1 h an additional quantity of BBr₃ (2 eq.) was added and the mixture was stirred at RT for 1 h, then quenched with aqueous HCl (1 N) and extracted with AcOEt. The combined organic phase was dried and solvent was evaporated under reduced pressure to give a residue which was purified by RP-HPLC (Conditions: Waters X-TERRA MS C18, 10 micron, 19×150 mm; flow: 20 mL/min; Gradient: A: H₂O+0.05% TFA; B: MeCN+0.05% TFA; 90% A isocratic for 2 min then linear to 10% A in 9 min) to afford the title compound (47%) as a solid.

¹H NMR (400 MHz, DMSO-d₆, 300 K) δ 1.1-1.3 (m, 3H), 1.5-1.8 (m, 7H), 2.44 (m, 1H), 3.3-3.7 (m, 8H), 4.88 (s, 2H), 7.32 (d, J=11.2 Hz, 2H), 7.59 (d, J=11.2 Hz, 2H), 7.79 (s, 1H); MS (ES⁺) m/z 487, 489 (M+H)⁺.

EXAMPLE 18

5-(4-chlorophenyl)-6-cyclohexyl-N-methyl-4-(2-morpholin-4-yl-2-oxoethyl)-4H-thieno[3,2-b]pyrrole-2-carboxamide A solution (0.02 M) of 5-(4-chlorophenyl)-6-cyclohexyl-4-(2-morpholin-4-yl-2-oxoethyl)-4H-thieno[3,2-b]pyrrole-2-carboxylic acid in DCM at RT was treated with methylamine (2 N solution in THF, 1.5 eq.), DIEA (3 eq.) and HATU (2 eq.). The mixture was stirred at RT for 2 h, then it was diluted with DCM and washed sequentially with aqueous HCl (0.1 N), aqueous NaHCO₃ (saturated solution) and dried. Evaporation of the solvent under reduced pressure gave a residue which was purified by RP-HPLC (Conditions: Waters X-TERRA MS C18, 10 micron, 19×100 mm; flow: 20 mL/min; Gradient: A: H₂O+0.05% TFA; B: MeCN+0.05% TFA; 50% A isocratic for 1 min then linear to 20% A in 9 min) to afford the title compound (74%) as a solid.

¹H NMR (300 MHz, DMSO-d₆, 300 K) δ 1.1-1.3 (m, 3H), 1.5-1.8 (m, 7H), δ 2.44 (m, 1H), 2.76 (B, 3H), 3.3-3.6 (m, 8H), 4.79 (s, 2H), 7.30 (d, J=6.8 Hz, 2H), 7.58 (d, J=8.0 Hz, 2H), 7.61 (s, 1H), 8.26 (bs, 1H); MS (ES⁺) m/z 500, 502 (M+H)⁺.

EXAMPLE 19

5-(4-chlorophenyl)-6-cyclohexyl-N-(ethylsulfonyl)-4-(2-morpholin-4-yl-2-oxoethyl)-4H-thieno[3,2-b]pyrrole-2-carboxamide A solution (0.015 M) of 5-(4-chlorophenyl)-6-cyclohexyl-4-(2-morpholin-4-yl-2-oxoethyl)-4H-thieno[3,2-b]pyrrole-2-carboxylic acid in THF at RT was treated with CDI (1.1 eq.) and DMAP (1.1 eq.). After stirring for 1 h at RT, ethanesulfonamide (2 eq.) and DBU (2 eq.) were added. The mixture was heated to reflux for 5 h then cooled down and diluted with AcOEt. The organic phase was washed with aqueous HCl (0.1 N) and dried. Evaporation of the solvent under reduced pressure gave a residue which was purified by RP-HPLC (Conditions: Waters X-TERRA MS C18, 10 micron, 19×100 mm; flow: 20 mL/min; Gradient: A: H₂O+0.05% TFA; B: MeCN+0.05% TFA; 50% A isocratic for 1 min then linear to 20% A in 9 min) to afford the title compound (17%) as a solid.

¹H NMR (400 MHz, DMSO-d₆, 300 K) δ 1.1-1.3 (m, 7H), 1.5-1.8 (m, 8H), 2.44 (m, 1H), 3.4-3.6 (m, 8H), 4.83 (s, 2H), 7.33 (d, J=8.0 Hz, 2H), 7.61 (d, J=8.0 Hz, 2H), 8.07 (s, 1H), 11.91 (bs, 1H); MS (ES⁺) m/z 578, 580 (M+H)⁺.

EXAMPLE 20

6-cyclohexyl-5-(3-furyl)-4-{2-[(1-isopropylpyrrolidin-3-yl)(methyl)amino]-2-oxoethyl}-4H-thieno[3,2-b]pyrrole-2-carboxylic acid Step 1: tert-butyl 5-bromo-6-cyclohexyl-4H-thieno[3,2-b]pyrrole-2-carboxylate A solution (0.2 M) of 6-cyclohexyl-4H-thieno[3,2-b]pyrrole-2-carboxylic acid (prepared as described in example 14, step 8) in THF was treated with tert-butyl N,N'-diisopropylimidocarbamate (2 eq.). The reaction mixture was heated to reflux for 1 h. After cooling down, the mixture was filtered trough a pad of silica gel and washed with AcOEt. Evaporation under reduced pressure of the filtrate gave a residue that was dissolved in DCM. The resulting solution (0.2 M) was cooled at 0° C. and treated with NBS (1 eq.). The reaction mixture was stirred at 0° C. for 1 h, then it was quenched with aqueous Na₂S₂O₃ (saturated solution) and extracted with AcOEt. The combined organic phase was washed with aqueous Na₂S₂O₃ (saturated solution) and brine and dried. Evaporation of the solvent under reduced pressure afforded the title compound (37%) as a solid.

¹H NMR (300 MHz, DMSO-d₆, 300 K) δ 1.45-1.80 (m, 4H), 1.73 (s, 9H), 1.85-2.05 (m, 6H), 2.80 (m, 1H), 7.70 (s, 1H), 12.29 (s, 1H); MS (ES⁺) m/z 385, 387 (M+H)⁺.

Step 2: 6-cyclohexyl-5-(3-furyl)-4-{2-[(1-isopropylpyrrolidin-3-yl)(methyl)amino]-2-oxoethyl}-4H-thieno[3,2-b]pyrrole-2-carboxylic acid A solution (0.5 M) of tert-butyl 5-bromo-6-cyclohexyl-4H-thieno[3,2-b]pyrrole-2-carboxylate in DMF was treated with NaH (2 eq., 60% dispersion in mineral oil) and the suspension was stirred at RT for 30 min then methyl bromoacetate (3 eq.) was added. The reaction mixture was heated at 50° C. for 1 h, then after cooling down, it was diluted with AcOEt and aqueous HCl (1 M) was added. The aqueous phase was separated and extracted with AcOEt. The combined organic phase was washed sequentially with aqueous HCl (1 N), aqueous NaHCO$_3$ (saturated solution) and brine then dried. Evaporation of the solvent under reduced pressure gave a residue that was dissolved in DME. The resulting solution (0.2 M) was treated with 3-furylboronic acid (1.5 eq.) and aqueous Na$_2$CO$_3$ (1 M solution, 2 eq.), the mixture was degassed and PdCl$_2$(dppf)$_2$ (0.05 eq.) was added. The reaction was heated to 80° C. for 5 h under argon atmosphere. After cooling down, the reaction was treated with aqueous HCl (1 N) and extracted with AcOEt. The combined organic phase was washed with brine and dried. Evaporation of the solvent under reduced pressure gave a residue that was purified by flash chromatography on silica gel (1:9 AcOEt/petroleum ether) affording tert-butyl 6-cyclohexyl-5-(3-furyl)-4-(2-methoxy-2-oxoethyl)-4H-thieno[3,2-b]pyrrole-2-carboxylate that was dissolved in MeOH. The resulting solution (0.1 M) was treated with aqueous NaOH (2 N solution, 6 eq.). The reaction mixture was heated to reflux for 2 h. After cooling down, the reaction was concentrated and acidified to pH 1 with aqueous HCl (6 N). The acidic layer was extracted with AcOEt and the combined organic phase was washed with HCl (1 M) and brine, then dried. Evaporation of the solvent under reduced pressure gave a residue that was dissolved in DCM. The resulting solution (0.1 M) was treated with DIEA (2.5 eq.), 1-isopropyl-N-methylpyrrolidin-3-amine (1.1 eq.) and HATU (1.5 eq.). The reaction mixture was stirred at RT overnight, then it was diluted with AcOEt and washed sequentially with aqueous NaHCO$_3$ (saturated solution) and brine then dried. Evaporation of the solvent under reduced pressure gave a residue that was treated with methanolic HCl (1.2 M solution, 25 eq.). The resulting solution (0.1 M) was stirred at RT for 2 h. Evaporation of the solvent under reduced pressure gave a residue that was purified by RP-HPLC (Conditions: Waters X-TERRA MS C18, 5 micron, 19×150 mm; flow: 20 mL/min; Gradient: A: H$_2$O+0.1% TFA; B: MeCN+0.1% TFA; linear from 95% A to 5% A in 10 min) to afford the title compound (14%) as its TFA salt.

$^1$H NMR (500 MHz, pyridine-d, 300 K) mixture of rotamers, δ 1.05-1.15 (m, 7H), 1.15-1.25 (m, 3H), 1.50-1.75 (m, 3H), 1.75-1.95, 2.00-2.15* (m, 5H), 2.80 (m, 4H), 2.90-3.10 (m, 4H), 3.10-3.30 (m, 2H), 5.09, 5.10-5.40* (s and m, 2H), 6.76 (s, 1H), 7.79 (s, 1H), 7.97 (s, 1H), 8.25 (s, 1H); MS (ES$^+$) m/z 500 (M+H)$^+$.

EXAMPLE 21

6-cyclohexyl-4-methyl-5-(1,3-oxazol-5-yl)-4H-thieno[3,2-b]pyrrole-2-carboxylic acid A solution (0.5 M) of 6-cyclohexyl-4H-thieno[3,2-b]pyrrole-2-carboxylic acid in DMF was treated with K$_2$CO$_3$ (2 eq.) and MeI (4 eq.). The reaction mixture was stirred at RT for 2 days. After dilution with AcOEt it was washed with water, brine and dried. Evaporation of the solvent gave a residue that was purified by flash chromatography on silica gel (1:4 AcOEt/petroleum ether) affording methyl 6-cyclohexyl-4-methyl-4H-thieno[3,2-b]pyrrole-2-carboxylate that was dissolved in DCE. POCl$_3$ (1.4 eq.) was poured in a flask and cooled at 0° C. under nitrogen atmosphere. DMF (1.2 eq.) was added and the resulting oil was stirred at RT for 6 h, and then cooled again to 0° C. To this cool oil was added the previously prepared solution (0.02 M) in DCE. After stirring for 12 h, the reaction mixture was treated with aqueous Na$_2$CO$_3$ (30% solution) and extracted with AcOEt. The combined organic phase was washed with brine, dried. Evaporation of the solvent under reduced pressure gave a crude that was dissolved in dry MeOH. The resulting solution (0.1 M) was treated with K$_2$CO$_3$ (1 eq.) and TosMIC (1 eq.). The reaction mixture was heated to reflux for 12 h, then cooled and diluted with water. The aqueous phase was extracted with AcOEt. The combined organic phase was washed with water and brine and dried. After concentration under vacuum, the resulting crude was dissolved in MeOH. The resulting solution (0.1 M) was treated with aqueous NaOH (2 N solution, 4 eq.). The reaction mixture was heated to 80° C. for 1 h. After cooling down, the reaction was acidified at pH 2 with aqueous HCl (3 M) affording a precipitate that was filtered, dissolved in the minimum amount of DMSO and purified by RP-HPLC (Conditions: Waters X-TERRA MS C18, 5 micron, 19×150 mm; flow: 20 mL/min; Gradient: A: H$_2$O+0.1% TFA; B: MeCN+0.1% TFA; linear from 95% A to 5% A in 10 min) to afford the title compound (3%) as a solid.

$^1$H NMR (400 MHz, DMSO-d$_6$, 300 K) δ 1.2-1.8 (m, 10H), 2.69 (m, 1H), 3.74 (s, 3H), 7.49 (s, 1H), 7.90 (s, 1H), 8.59 (s, 1H); MS (ES$^+$) m/z 331 (M+H)$^+$.

EXAMPLE 22 methyl 6-benzyl-4-cyclohexyl-5-phenyl-6H-thieno[2,3-b]pyrrole-2-carboxylate

Step 1: methyl 2-cyano-4-oxo-4-phenylbutanoate

A solution (1 M) of phenacyl bromide in THF was added dropwise to a solution (5.5 M) of methyl cyanoacetate (1.1 eq.) and DIEA (2.4 eq.) in THF at RT. The resulting solution was stirred at RT for 20 h then the mixture was filtered and the filtrate was concentrated in vacuo to obtain an oil that was treated with little portions of aqueous HCl (1 N). The organic phase was washed with brine, dried and concentrated affording the title compound (97%) as an oil that solidified when stored in the fridge.

$^1$H NMR (400 MHz, CDCl$_3$, 300 K) δ 3.58 (dd, J$_1$=18.1 Hz, J$_2$=5.5 Hz 1H), 3.80 (dd, J$_1$=18.1 Hz, J$_2$=6.9 Hz, 1H), 3.88 (s, 3H), 4.18 (m, 1H), 7.51 (t, J=7.6 Hz, 2H), 7.64 (t, J=6.9 Hz, 1H), 7.97 (d, J=8.13 Hz, 2H); MS (ES$^+$) m/z 218 (M+H)$^+$.

Step 2: methyl 2-chloro-5-phenyl-1H-pyrrole-3-carboxylate

A solution (0.05 M) of methyl 2-cyano-3-oxo-3-phenylpropanoate in chloroform/Et$_2$O (1:1) at RT was prepared. Hydrogen chloride gas was then bubbled into the solution until TLC (1:4 AcOEt/petroleum ether) indicated the absence of starting material. During the introduction of gas, the temperature of the reaction was kept below 30° C. with cooling. The mixture was filtered and the filtrate was washed several times with water. The organic layer was dried and concentrated to give a residue that was purified by flash chromatography on silica gel (1:4 AcOEt/petroleum ether) to afford the title compound (40%) as a solid.

$^1$H NMR (300 MHz, CDCl$_3$, 300 K) δ 3.87 (s, 3H), 6.86 (d, J=3.1 Hz, 1H), 7.29 (m, 1H), 7.4 (m, 4H), 8.67 (bs, 1H); MS (ES$^+$) m/z 234, 236 (M+H)$^+$.

Step 3: methyl 1-benzyl-2-chloro-5-phenyl-1H-pyrrole-3-carboxylate

A solution (7 M) of methyl 2-chloro-5-phenyl-1H-pyrrole-3-carboxylate in DMF at 0° C. was treated with NaH (1.2 eq., 60% dispersion in mineral oil), and the suspension was stirred at RT for 30 min then it was treated with benzyl bromide (1.2 eq.). The reaction mixture was stirred at RT for 90 min then poured into water and extracted with AcOEt. The combined organic phase was washed with water and dried. Evaporation of the solvent gave a residue that was purified by flash chromatography on silica gel (1:8 AcOEt/petroleum ether) to afford the title compound (71%) as a solid.

$^1$H NMR (300 MHz, CDCl$_3$, 300 K) δ 3.86 (s, 3H), 5.21 (s, 2H), 6.71 (s, 1H), 6.91 (d, J=6.2 Hz, 2H), 7.2-7.3 (m, 8H); MS (ES$^+$) m/z 326, 328 (M+H)$^+$.

Step 4: (1-benzyl-2-chloro-5-phenyl-1H-pyrrol-3-yl)methanol

A solution (0.24 M) of methyl 1-benzyl-2-chloro-5-phenyl-1H-pyrrole-3-carboxylate in DCM at −78° C. was treated with diisobutylaluminium hydride (1 M solution in DCM, 2.5 eq.). The resulting solution was stirred at −78° C. for 2 h then it was warmed to 0° C. and quenched with MeOH. The Rochelle solution (10% wt sodium and potassium tartrate) was added and the mixture was stirred at RT for 1 h (until two phases came out). The mixture was extracted with DCM and the combined organic phase was treated with brine and dried. Evaporation of the solvent afforded the title compound (90%) as an oil.

$^1$H NMR (300 MHz, CDCl$_3$, 300 K) δ 4.61 (s, 2H), 5.18 (s, 2H), 6.35 (s, 1H), 6.94 (d, J=6.6 Hz, 2H), 7.2-7.3 (m, 8H); MS (ES$^+$) m/z 298, 300 (M+H)$^+$.

Step 5: 1-benzyl-2-chloro-5-phenyl-1H-pyrrole-3-carbaldehyde

A solution (0.1 M) of (1-benzyl-2-chloro-5-phenyl-1H-pyrrol-3-yl)methanol in DCM at 0° C. was treated with N-methylmorpholine oxide (1.5 eq.) and TPAP (0.05 eq.). The mixture was stirred at RT for 1 h then it was filtered through a pad of silica gel and washed with DCM. The combined organic phase was concentrated affording the title compound (77%) as an oil.

$^1$H NMR (300 MHz, CDCl$_3$, 300 K) δ 5.22 (s, 2H), 6.71 (s, 1H), 6.93 (d, J=6.8 Hz, 2H), 7.2-7.4 (m, 8H), 9.93 (s, 1H); MS (ES$^+$) m/z 296, 298 (M+H)$^+$.

Step 6: methyl 6-benzyl-5-phenyl-6H-thieno[2,3-b]pyrrole-2-carboxylate

A solution (1.1 M) of 1-benzyl-2-chloro-5-phenyl-1H-pyrrole-3-carbaldehyde in THF at 0° C. was treated with methyl thioglycolate (1.5 eq.) and a solution (2 M) of potassium tert-butoxide (2.5 eq.) in THF. The mixture was stirred at 0° C. for 2 h then at RT for 40 h. The reaction was quenched with water and pH was turned to neutral value by addition of aqueous ammonium chloride (saturated solution). The mixture was extracted with AcOEt and the combined organic phase was washed with brine and dried. Evaporation of the solvent gave a residue that was purified by flash chromatography on silica gel (1:30 acetone/toluene) to afford the title compound (38%) as a solid.

$^1$H NMR (400 MHz, CDCl$_3$, 300 K) δ 3.87 (s, 3H), 5.21 (s, 2H), 6.58 (s, 1H), 7.13 (d, J=6.6 Hz, 2H), 7.2-7.4 (m, 8H), 7.83 (s, 1H); MS (ES$^+$) m/z 348 (M+H)$^+$.

Step 7: methyl 6-benzyl-4-cyclohex-1-en-1-yl-5-phenyl-6H-thieno[2,3-b]pyrrole-2-carboxylate A solution (0.2 M) of methyl 6-benzyl-5-phenyl-6H-thieno[2,3-b]pyrrole-2-carboxylate in acetic acid was treated with acetic anhydride (10 eq.), cyclohexanone (10 eq.) and 85% phosphoric acid (2.3 eq.). The mixture was heated at 80° C. for 3 h, then was poured into ice cold ammonium hydroxide. The product was extracted with AcOEt and the combined organic phase was washed sequentially with aqueous HCl (1 N), aqueous NaHCO$_3$ (saturated solution) and brine then dried and concentrated. The crude was purified by flash chromatography on silica gel (1:30 acetone/toluene) affording the title compound (95%) as a solid.

$^1$H NMR (300 MHz, CDCl$_3$, 300 K) δ 1.5-1.6 (m, 4H) 1.9-2.1 (m, 4H), 3.84 (s, 3H), 4.95 (s, 2H), 5.85 (m, 1H), 7.0-7.1 (m, 2H), 7.2-7.4 (m, 8H), 7.91 (s, 1H); MS (ES$^+$) m/z 428 (M+H)$^+$.

Step 8: 6-benzyl-4-cyclohexyl-5-phenyl-6H-thieno[2,3-b]pyrrole-2-carboxylic acid A solution (0.7 M) of methyl 6-benzyl-4-cyclohex-1-en-1-yl-5-phenyl-6H-thieno[2,3-b]pyrrole-2-carboxylate in TFA at 0° C. was treated with triethylsilane (1.5 eq.). The mixture was stirred at 0° C. for 1 h then concentrated to give a residue that was purified by flash chromatography on silica gel (1:30 acetone/toluene) affording methyl 6-benzyl-4-cyclohexyl-5-phenyl-6H-thieno[2,3-b]pyrrole-2-carboxylate as a solid that was dissolved in THF/MeOH (1:1). The resulting solution (0.04 M) was treated with aqueous KOH (1 N solution, 4 eq.) then the mixture was heated to 80° C. for 4 h. After cooling down, the mixture was concentrated then the resulting residue was diluted with water and pH was turned to neutral value by addition of aqueous ammonium chloride (saturated solution). The mixture was concentrated to give a residue that was purified by RP-HPLC (Conditions: Waters X-TERRA MS C18, 10 micron, 10×150 mm; flow: 20 mL/min; Gradient: A: H$_2$O+0.05% TFA; B: MeCN+0.05% TFA; 50% A isocratic for 2 min then linear to 0% A in 10 min) to afford the title compound (58%) as a solid.

$^1$H NMR (400 MHz, DMSO-d$_6$, 300 K) δ 1.1-1.4 (m, 3H) 1.6-1.9 (m, 7H), 2.42 (bt, 1H), 5.01 (s, 2H), 7.0-7.1 (m, 2H), 7.2-7.6 (m, 8H), 7.83 (s, 1H) 12.63 (bs, 1H); MS (ES$^+$) m/z 416 (M+H)$^+$.

EXAMPLE 23

4-cyclohexyl-5-phenyl-6H-thieno[2,3-b]pyrrole-2-carboxylic acid

Step 1: ethyl 5-[(tert-butoxycarbonyl)amino]-4-(phenylethynyl)thiophene-2-carboxylate Pd(PhCN)$_2$Cl$_2$ (0.03 eq.) and CuI (0.02 eq.) were added to a dry septum-capped vial, which was then sparged with argon and charged with ethyl 4-bromo-5-[(tert-butoxycarbonyl)amino]thiophene-2-carboxylate (prepared as described in example 14, step 4) (1 M solution in dioxane), DIEA (1.2 eq.), P(t-Bu)$_3$ (0.06 eq., 0.8 M solution in dioxane) and phenylacetylene (1.2 eq.). The reaction was stirred overnight at RT, then diluted with AcOEt and filtered trough a small pad of silica gel. The filtrate was concentrated giving a residue that was purified by flash chromatography on silica gel (1:5 AcOEt/petroleum ether) to afford the title compound (96%) as a solid.

$^1$H NMR (300 MHz, DMSO-d, 300 K) δ 1.28 (t, J=7.1 Hz, 3H), 1.52 (s, 9H), 4.25 (q, J=7.1 Hz, 2H), 7.40-7.44 (m, 3H), 7.56-7.66 (m, 3H), 10.91 (s, 1H); MS (ES$^+$) m/z 372 (M+H)$^+$.

Step 2: 4-tert-butyl 2-ethyl 5-phenyl-6H-thieno[2,3-b]pyrrole-2,4-dicarboxylate

A solution (0.2 M) of ethyl 5-[(tertbutoxycarbonyl)amino]-4-(phenylethynyl)thiophene-2-carboxylate in anhydrous THF was treated with potassium carbonate (2 eq.). The mixture was sparged with argon and Pd$_2$(dba)$_3$ (0.01 eq.) and P(tBu)$_3$ (0.06 eq., 0.8 M solution in dioxane) were added. The reaction was heated to 80° C. under argon atmosphere overnight. After cooling down, the reaction was acidified with aqueous HCl (1 N) and extracted with AcOEt. The combined organic phase was washed with brine and dried. Evaporation of the solvent gave a residue that was purified by flash chromatography on silica gel (1:4 AcOEt/petroleum ether) to afford the title compound (66%) as a solid.

$^1$H NMR (300 MHz, DMSO-d$_6$, 300 K) δ 1.32 (t, J=7.1 Hz, 3H), 1.37 (s, 9H), 4.31 (q, J=7.1 Hz, 2H), 6.89 (s, 1H), 7.35-7.50 (m, 5H), 8.04 (s, 1H); MS (ES$^+$) m/z 372 (M+H)$^+$.

Step 3: ethyl 4-cyclohexyl-5-phenyl-6H-thieno[2,3-b]pyrrole-2-carboxylate

A solution (0.2 M) of 4-tert-butyl 2-ethyl 5-phenyl-6H-thieno[2,3-b]pyrrole-2,4-dicarboxylate in acetic acid was treated with acetic anhydride (2.5 eq.), cyclohexanone (10 eq.) and 85% phosphoric acid (2.3 eq.). The mixture was heated at 80° C. overnight, then it was poured into ice cold ammonium hydroxide. The product was extracted with AcOEt and the combined organic layers were washed sequentially with aqueous HCl (1 N), aqueous NaHCO$_3$ (saturated solution) and brine then dried and concentrated. The crude was dissolved in TFA and cooled to 0° C. The resulting solution (0.1 M) was treated with triethylsilane (2 eq.) and stirred at 0° C. for 1 h then solvent was evaporated to give a residue that was purified by flash chromatography on silica gel (1:9 AcOEt/petroleum ether) to afford the title compound (58%) as a solid.

$^1$H NMR (300 MHz, DMSO-d$_6$, 300 K) δ 1.20-1.41 (m, 6H), 1.65-1.85 (m, 7H), 2.75 (m, 1H), 4.28 (q, J=7.1 Hz, 2H), 7.31-7.39 (m, 1H), 7.41-7.51 (m, 4H), 7.91 (s, 1H), 11.72 (s, 1H); MS (ES$^+$) m/z 354 (M+H)$^+$.

Step 4: 4-cyclohexyl-5-phenyl-6H-thieno[2,3-b]pyrrole-2-carboxylic acid

A solution (0.07 M) of ethyl 4-cyclohexyl-5-phenyl-6H-thieno[2,3-b]pyrrole-2-carboxylate in THF/MeOH (1:1) was treated with aqueous NaOH (2 N solution, 4 eq.). The mixture was heated to reflux for 6 hours. After cooling down, the reaction was concentrated and acidified to pH 1 with aqueous HCl (6 N). The resulting mixture was dissolved with DMSO and purified by RP-HPLC (Conditions: Waters X-TERRA MS C18, 5 micron, 19×150 mm; flow: 20 mL/min; Gradient: A: H$_2$O+0.1% TFA; B: MeCN+0.1% TFA; linear from 95% A to 5% A in 10 min) to afford the title compound (54%) as a solid.

$^1$H NMR (400 MHz, DMSO-d$_6$, 300 K) δ 1.29-1.38 (m, 4H), 1.69-1.80 (m, 6H), 2.76 (m, 1H), 7.36 (t, J=7.2 Hz, 1H), 7.43-7.51 (m, 4H), 7.82 (s, 1H), 11.63 (s, 1H); MS (ES$^+$) m/z 326 (M+H)$^+$.

EXAMPLE 24

4-cyclohexyl-6-[2-(dimethylamino)-2-oxoethyl]-5-phenyl-6H-thieno[2,3-b]pyrrole-2-carboxylic acid A solution (0.5 M) of ethyl 4-cyclohexyl-5-phenyl-6H-thieno[2,3-b]pyrrole-2-carboxylate in DMF was treated with NaH (2 eq., 60% dispersion in mineral oil), and the suspension was stirred at RT for 30 min, then 2-chloro-N,N-dimethylacetamide (3 eq.) was added. The reaction mixture was heated at 50° C. for 1 h and 25 min. After cooling down, it was diluted with AcOEt and aqueous HCl (1 M) was added. The aqueous phase was separated and extracted with AcOEt. The combined organic phase was washed sequentially with aqueous HCl (1 N), aqueous NaHCO$_3$ (saturated solution) and brine then dried and evaporated. The residue was dissolved in THF/MeOH (1:1). The resulting solution (0.07 M) was treated with NaOH (2 N, 6 eq.). The reaction mixture was heated to reflux overnight. After cooling down, the reaction was concentrated and acidified to pH 1 with aqueous HCl (3 N). The resulting mixture was diluted with DMSO and purified by RP-HPLC (Conditions: Waters X-TERRA MS C18, 5 micron, 19×150 mm; flow: 20 mL/min; Gradient: A: H$_2$O+ 0.1% TFA; B: MeCN+0.1% TFA; linear from 95% A to 5% A in 10 min) to afford the title compound (27%) as a solid.

$^1$H NMR (400 MHz, DMSO-d$_6$, 300 K) δ 1.17-1.32 (m, 4H), 1.63-1.75 (m, 6H), 2.41 (m, 1H), 2.81 (s, 3H), 2.84 (s, 3H), 4.68 (s, 2H), 7.28 (d, J=7.0 Hz, 2H), 7.43-7.53 (m, 3H), 7.84 (s, 1H); MS (ES$^+$) m/z 411 (M+H)$^+$.

TABLE 1

Additional Examples (N-substituted thieno[3,2-b]pyrroles)

| No. | STRUCTURE | Molecular Ion [M + H]$^+$ |
|---|---|---|
| 101 | 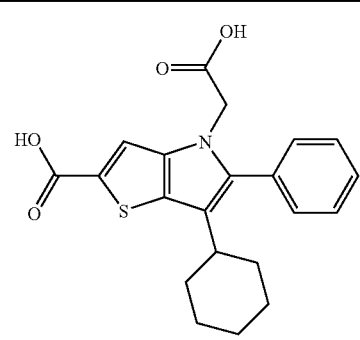 | 384 |

TABLE 1-continued

Additional Examples (N-substituted thieno[3,2-b]pyrroles)

| No. | STRUCTURE | Molecular Ion [M + H]+ |
|---|---|---|
| 102 | | 466 |
| 103 | | 437 |
| 104 | | 397 |

TABLE 1-continued
Additional Examples (N-substituted thieno[3,2-b]pyrroles)
| No. | STRUCTURE | Molecular Ion [M + H]+ |
|---|---|---|
| 105 | 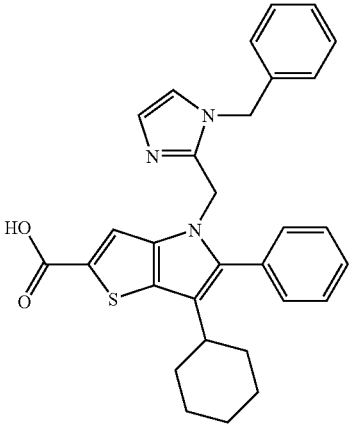 | 496 |
| 106 | 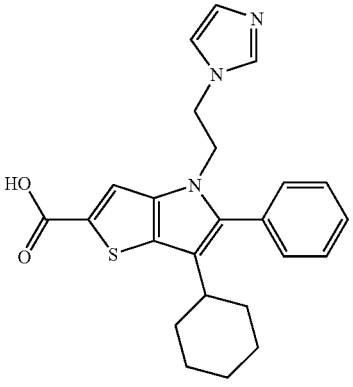 | 420 |
| 107 | 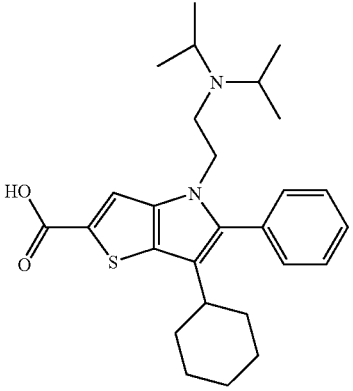 | 453 |

TABLE 1-continued

Additional Examples (N-substituted thieno[3,2-b]pyrroles)

| No. | STRUCTURE | Molecular Ion [M + H]+ |
|---|---|---|
| 108 | 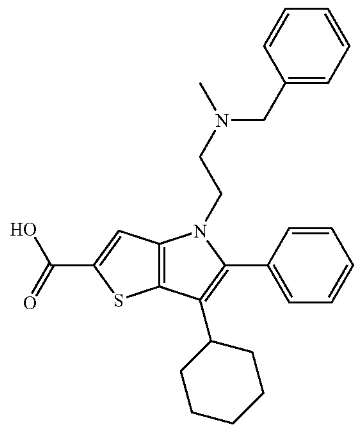 | 473 |
| 109 | 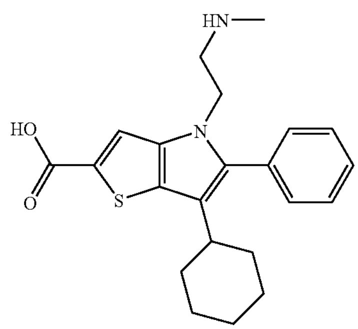 | 383 |
| 110 | 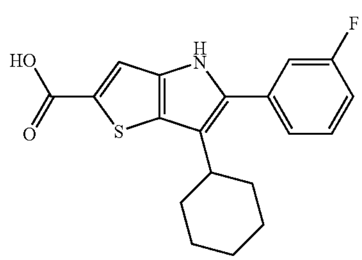 | 344 |
| 111 | 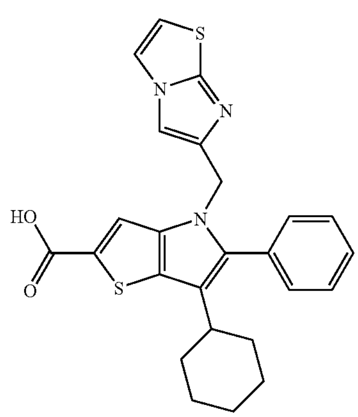 | 462 |

TABLE 1-continued

Additional Examples (N-substituted thieno[3,2-b]pyrroles)

| No. | STRUCTURE | Molecular Ion [M + H]+ |
|---|---|---|
| 112 | 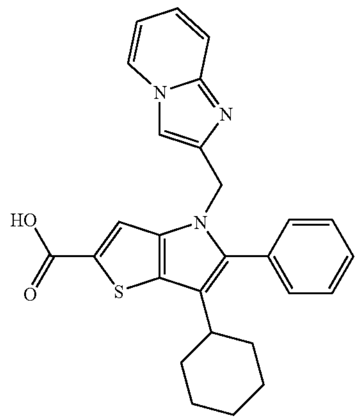 | 457 |
| 113 | 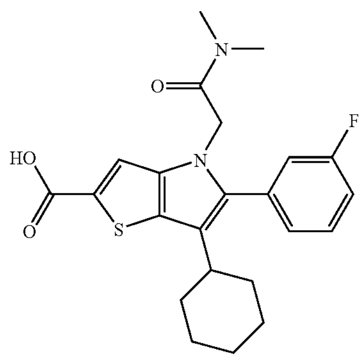 | 429 |
| 114 | 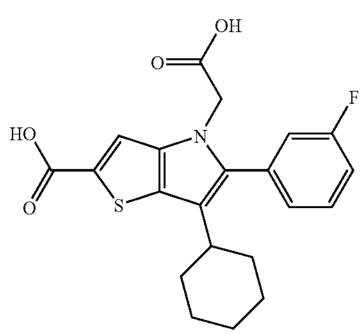 | 402 |
| 115 | 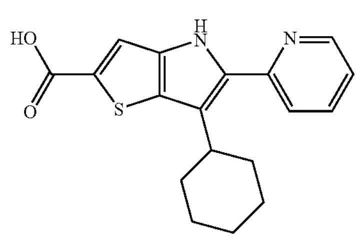 | 327 |

TABLE 1-continued

Additional Examples (N-substituted thieno[3,2-b]pyrroles)

| No. | STRUCTURE | Molecular Ion [M + H]+ |
|---|---|---|
| 116 | (5-methylisoxazol-3-yl)methyl N-substituted thieno[3,2-b]pyrrole with carboxylic acid, phenyl, and cyclohexyl substituents | 421 |
| 117 | carbamoylmethyl N-substituted thieno[3,2-b]pyrrole with carboxylic acid, phenyl, and cyclohexyl substituents | 383 |
| 118 | (pyridin-2-yl)methyl N-substituted thieno[3,2-b]pyrrole with carboxylic acid, phenyl, and cyclohexyl substituents | 417 |
| 119 | (pyridin-4-yl)methyl N-substituted thieno[3,2-b]pyrrole with carboxylic acid, phenyl, and cyclohexyl substituents | 417 |

TABLE 1-continued

Additional Examples (N-substituted thieno[3,2-b]pyrroles)

| No. | STRUCTURE | Molecular Ion [M + H]+ |
|-----|-----------|------------------------|
| 120 | 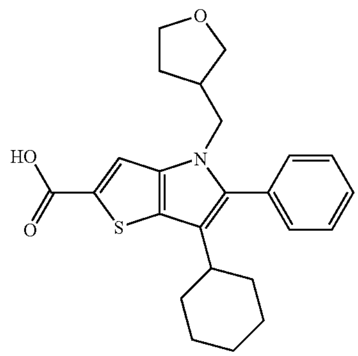 | 410 |
| 121 | 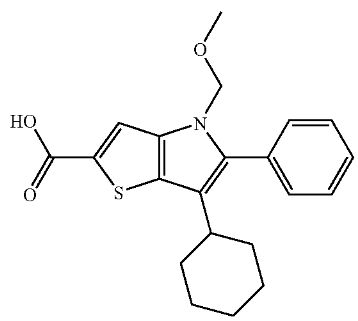 | 370 |
| 122 | 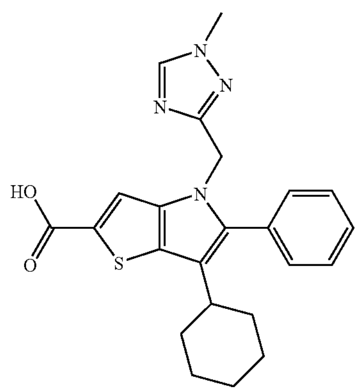 | 421 |
| 123 | 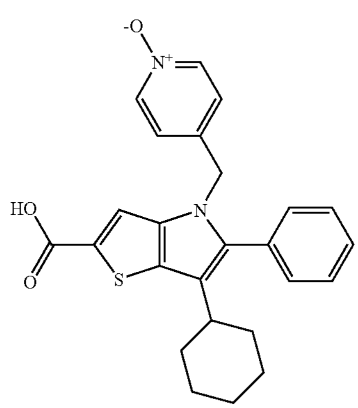 | 433 |

TABLE 1-continued
Additional Examples (N-substituted thieno[3,2-b]pyrroles)
| No. | STRUCTURE | Molecular Ion [M + H]+ |
|---|---|---|
| 124 | 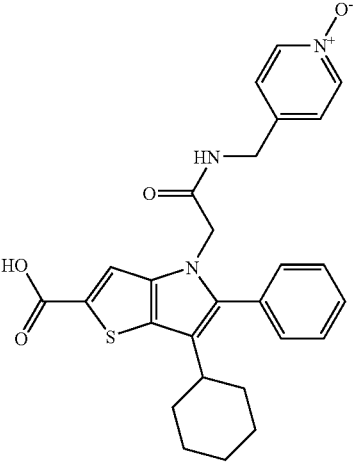 | 490 |
| 125 | 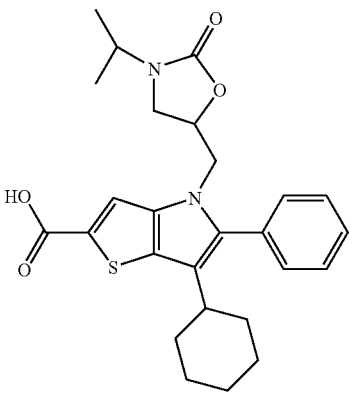 | 467 |
| 126 | 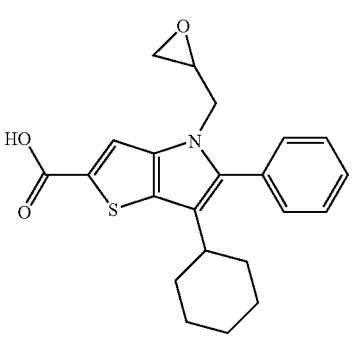 | 382 |

TABLE 1-continued

Additional Examples (N-substituted thieno[3,2-b]pyrroles)

| No. | STRUCTURE | Molecular Ion [M + H]$^+$ |
|---|---|---|
| 127 | 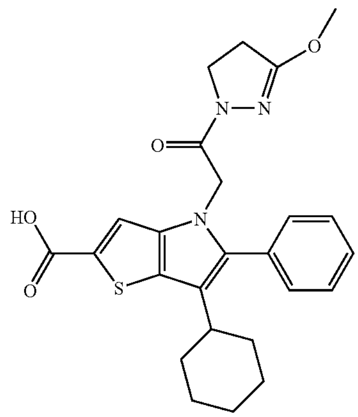 | 466 |
| 128 | 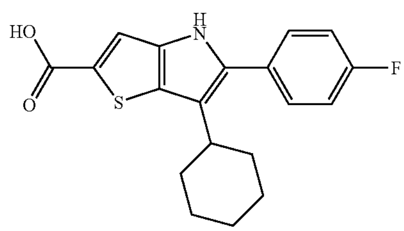 | 344 |
| 129 | 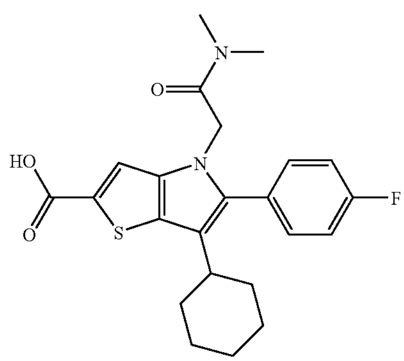 | 429 |
| 130 | 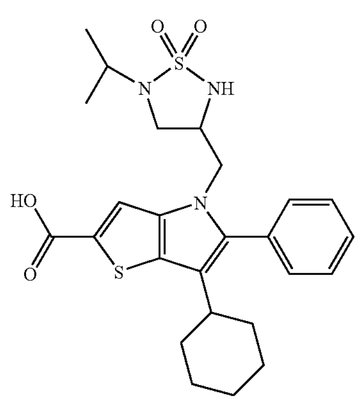 | 502 |

TABLE 1-continued
Additional Examples (N-substituted thieno[3,2-b]pyrroles)
| No. | STRUCTURE | Molecular Ion [M + H]+ |
|---|---|---|
| 131 | 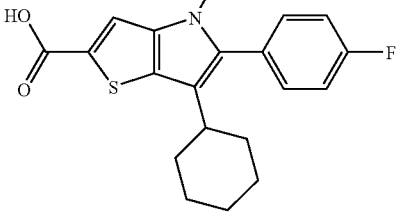 | 356 |
| 132 | 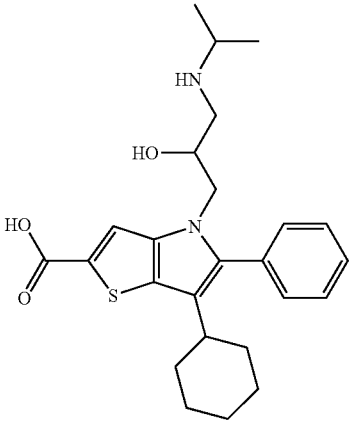 | 441 |
| 133 | 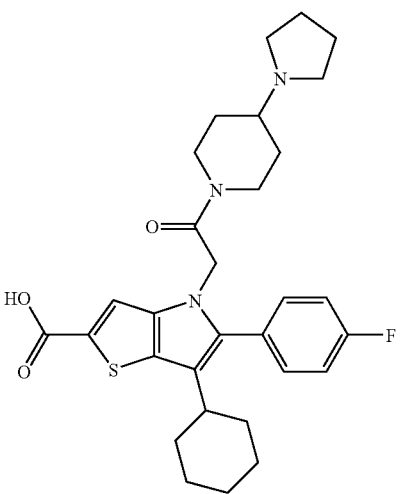 | 539, 541 |

TABLE 1-continued
Additional Examples (N-substituted thieno[3,2-b]pyrroles)
| No. | STRUCTURE | Molecular Ion [M + H]+ |
|---|---|---|
| 134 | 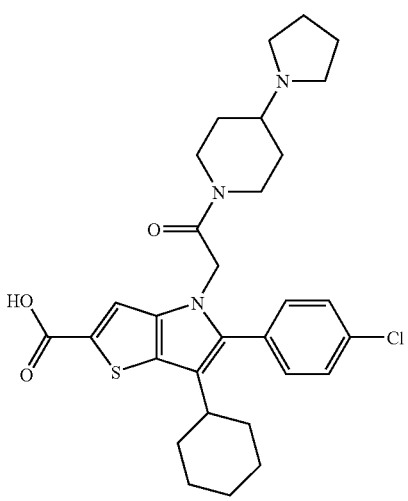 | 556, 558 |
| 135 | 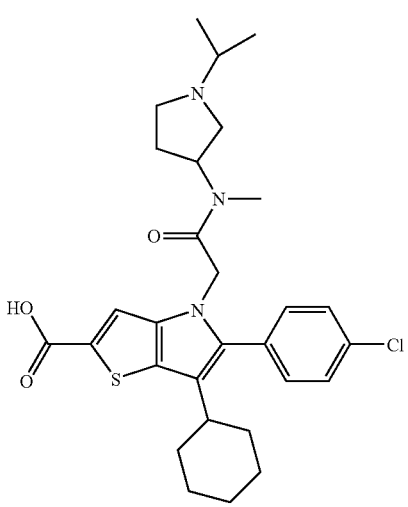 | 543, 545 |
| 136 | 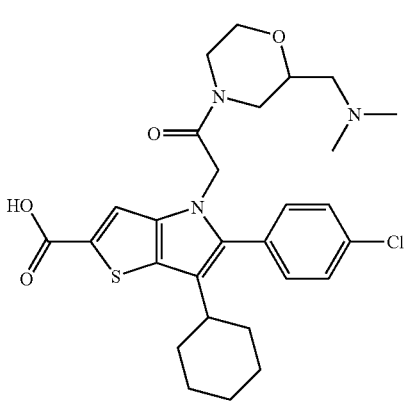 | 546, 548 |

TABLE 1-continued
Additional Examples (N-substituted thieno[3,2-b]pyrroles)
| No. | STRUCTURE | Molecular Ion [M + H]+ |
|---|---|---|
| 137 | 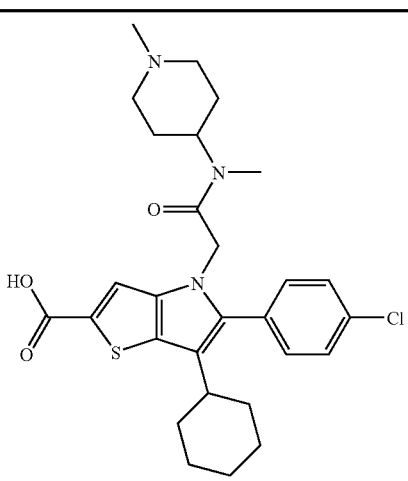 | 529, 531 |
| 138 | 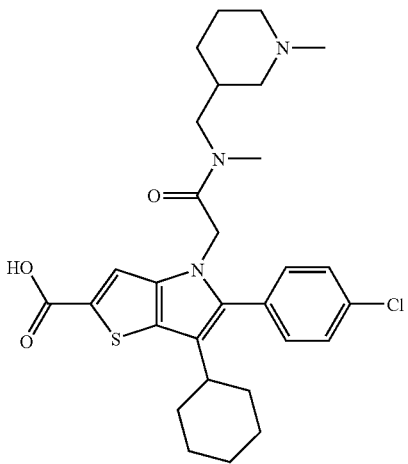 | 544, 546 |
| 139 | 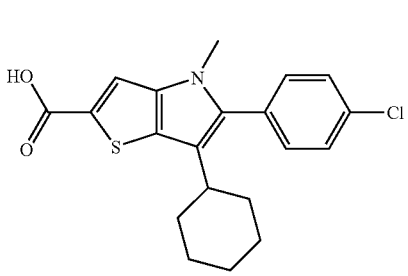 | 374, 376 |

TABLE 1-continued
Additional Examples (N-substituted thieno[3,2-b]pyrroles)
| No. | STRUCTURE | Molecular Ion [M + H]+ |
|---|---|---|
| 140 | 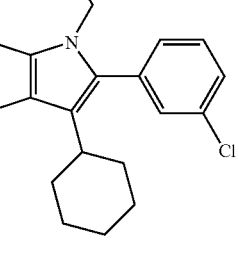 | 488, 490 |
| 141 | 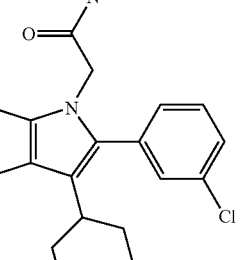 | 445, 447 |
| 142 | 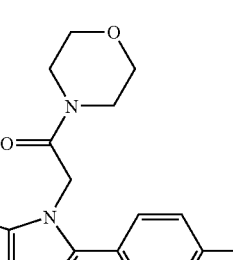 | 483 |

TABLE 1-continued
Additional Examples (N-substituted thieno[3,2-b]pyrroles)
| No. | STRUCTURE | Molecular Ion [M + H]+ |
|---|---|---|
| 143 | 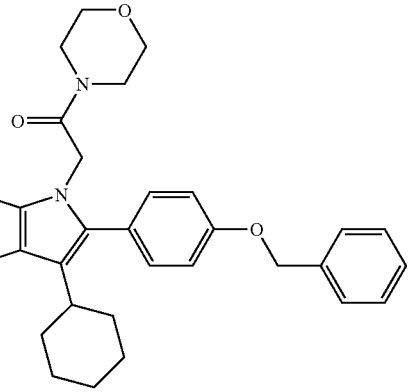 | 559 |
| 144 | 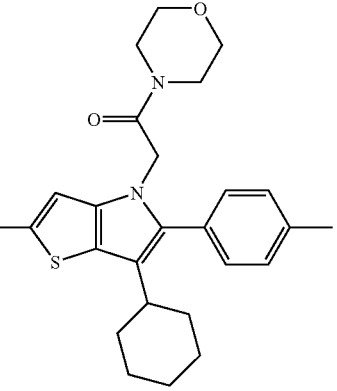 | 467 |
| 145 | 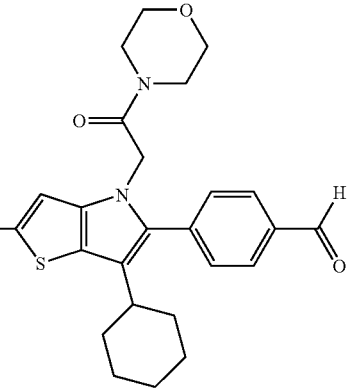 | 481 |

TABLE 1-continued

Additional Examples (N-substituted thieno[3,2-b]pyrroles)

| No. | STRUCTURE | Molecular Ion [M + H]+ |
|-----|-----------|------------------------|
| 146 | 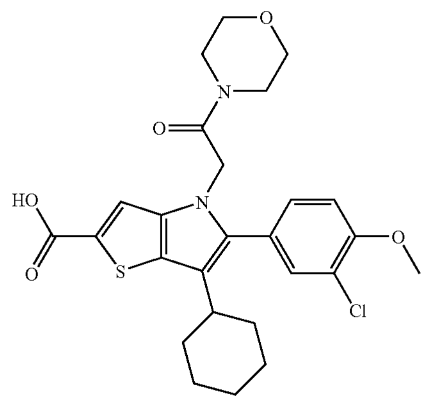 | 518, 520 |
| 147 | 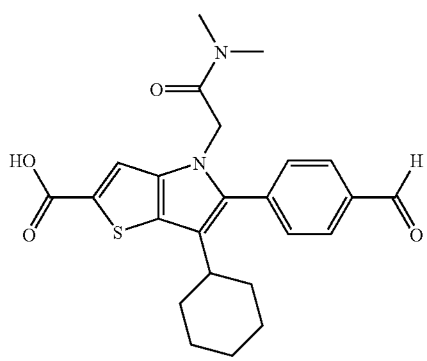 | 439 |
| 148 | 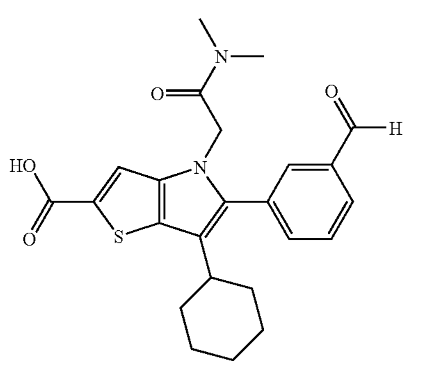 | 439 |
| 149 | 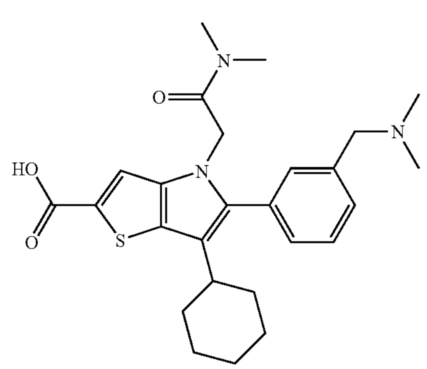 | 469 |

TABLE 1-continued

Additional Examples (N-substituted thieno[3,2-b]pyrroles)

| No. | STRUCTURE | Molecular Ion [M + H]+ |
|---|---|---|
| 150 | 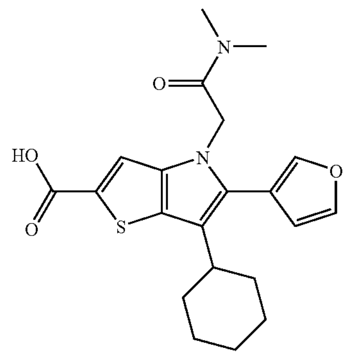 | 401 |
| 151 | 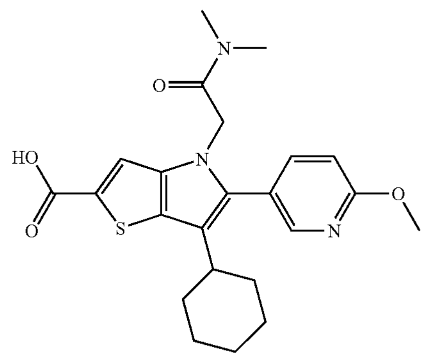 | 442 |
| 152 | 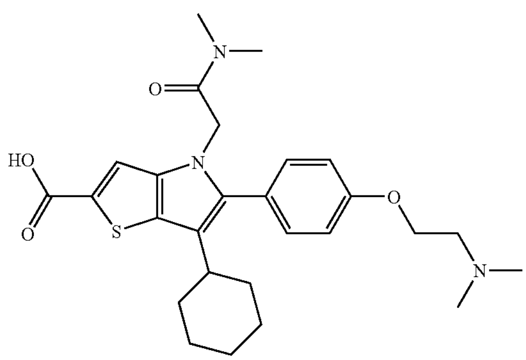 | 498 |
| 153 | 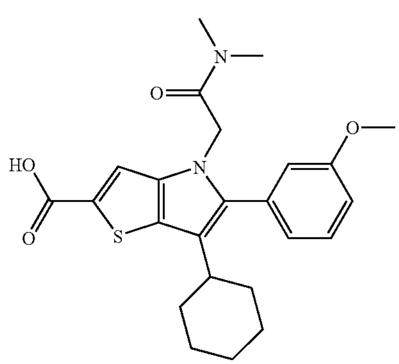 | 441 |

TABLE 2

Additional Examples (C-3 Substituted thieno[3,2-b]pyrroles)

| No. | STRUCTURE | Molecular Ion [M + H]+ |
|---|---|---|
| 201 | 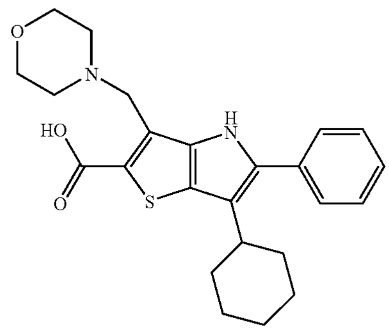 | 425 |
| 202 | 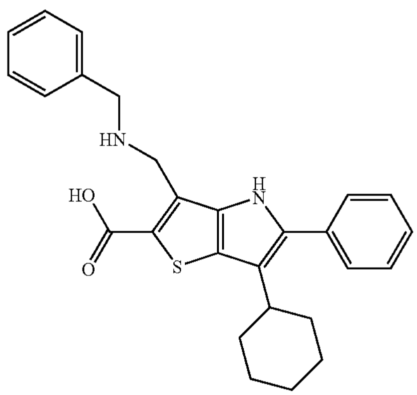 | 445 |
| 203 | 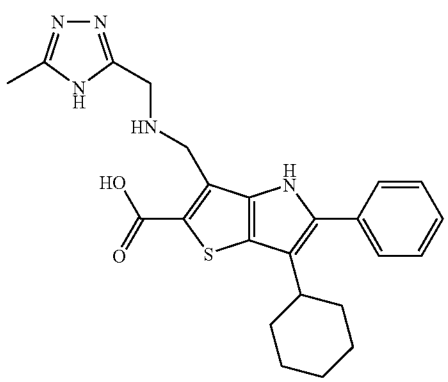 | 450 |
| 204 | 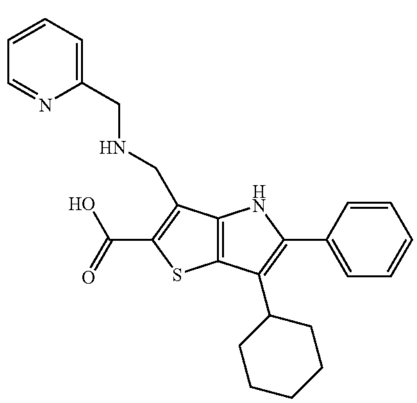 | 446 |

TABLE 2-continued

Additional Examples (C-3 Substituted thieno[3,2-b]pyrroles)

| No. | STRUCTURE | Molecular Ion [M + H]+ |
|---|---|---|
| 205 | 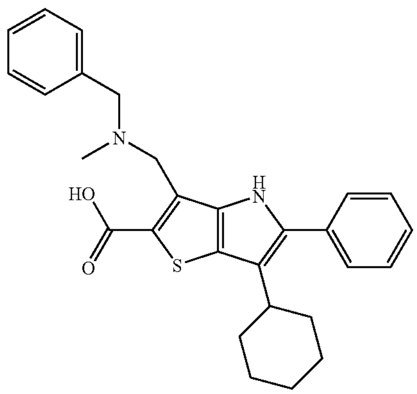 | 459 |

TABLE 3

Additional Examples (C-3, N-Disubstituted thieno[3,2-b]pyrroles)

| No. | STRUCTURE | Molecular Ion [M + H]+ |
|---|---|---|
| 301 | 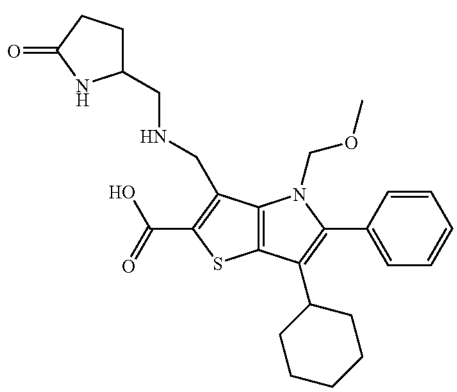 | 496 |
| 302 | 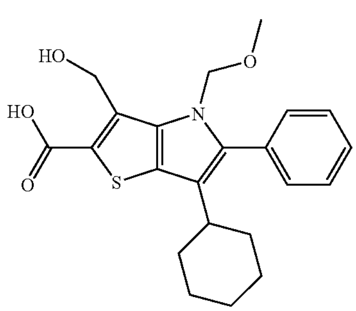 | 400 |

TABLE 3-continued
Additional Examples (C-3, N-Disubstituted thieno[3,2-b]pyrroles)
| No. | STRUCTURE | Molecular Ion [M + H]+ |
|---|---|---|
| 303 | 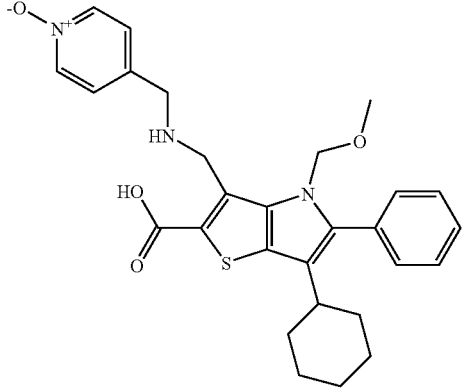 | 506 |
| 304 | 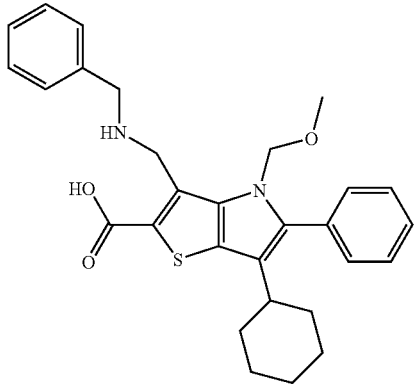 | 489 |
| 305 | 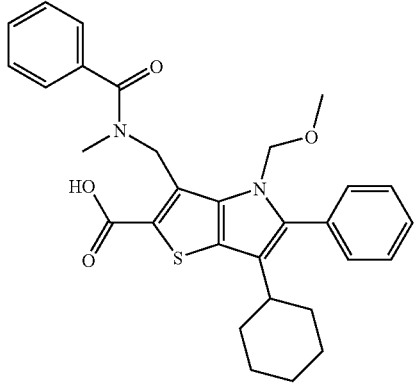 | 517 |

TABLE 3-continued

Additional Examples (C-3, N-Disubstituted thieno[3,2-b]pyrroles)

| No. | STRUCTURE | Molecular Ion [M + H]+ |
|---|---|---|
| 306 | 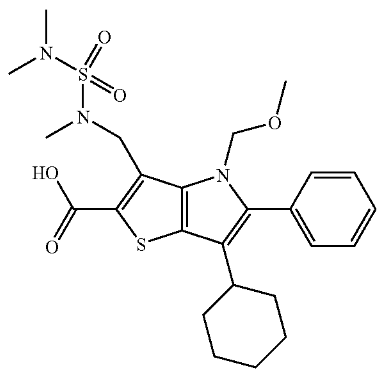 | 520 |
| 307 | 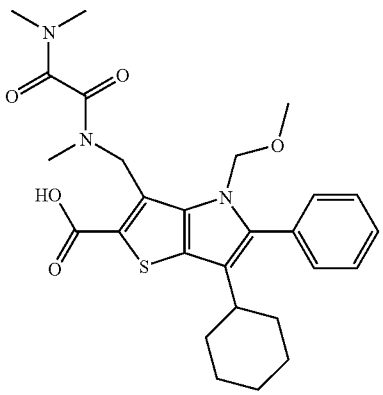 | 512 |
| 308 | 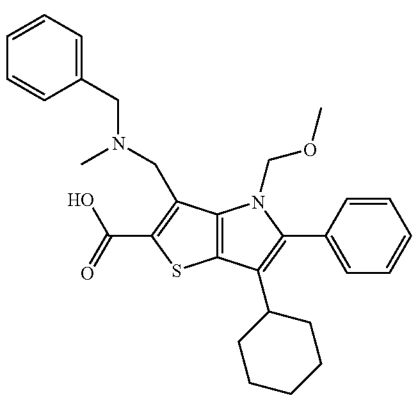 | 503 |
| 309 | 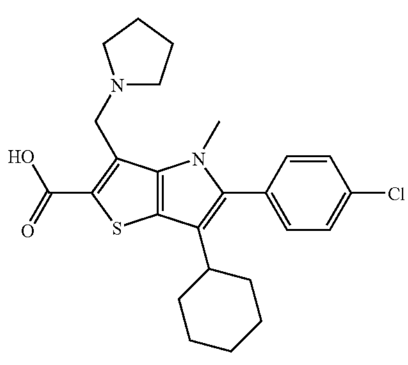 | 457, 459 |

TABLE 3-continued
Additional Examples (C-3, N-Disubstituted thieno[3,2-b]pyrroles)
| No. | STRUCTURE | Molecular Ion [M + H]+ |
|---|---|---|
| 310 | 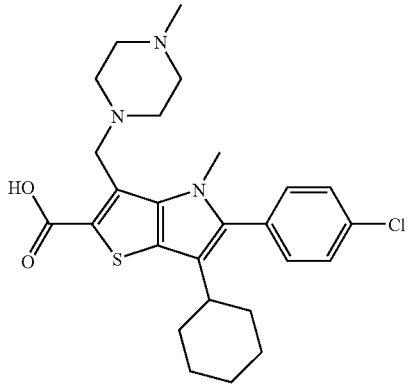 | 486, 488 |
| 311 | 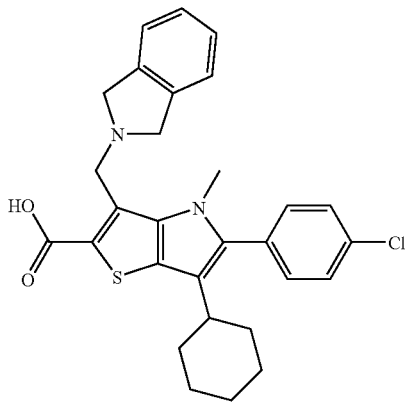 | 505, 507 |
| 312 | 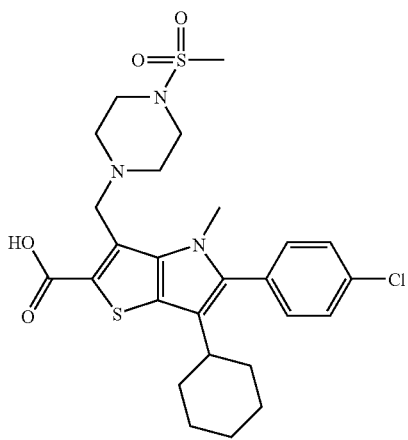 | 550, 552 |

TABLE 3-continued
Additional Examples (C-3, N-Disubstituted thieno[3,2-b]pyrroles)
| No. | STRUCTURE | Molecular Ion [M + H]+ |
|---|---|---|
| 313 | 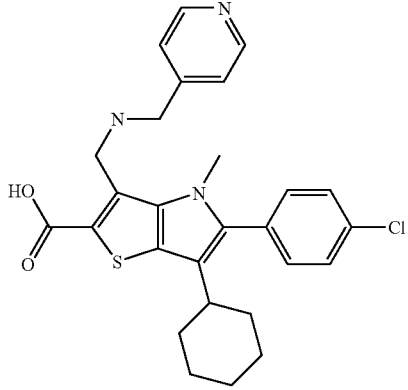 | 494, 496 |
| 314 | 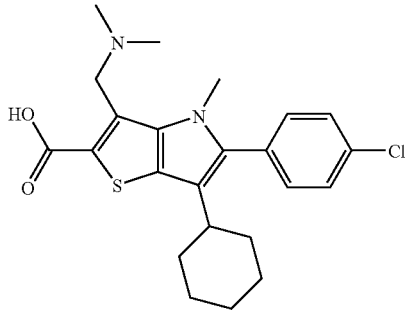 | 431, 433 |
| 315 | 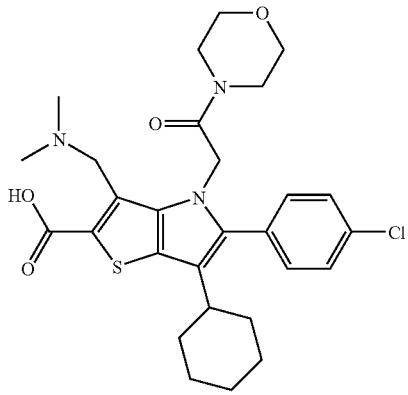 | 544, 546 |
| 316 | 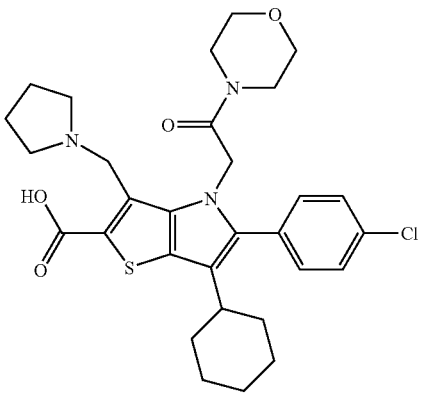 | 570, 572 |

TABLE 3-continued
Additional Examples (C-3, N-Disubstituted thieno[3,2-b]pyrroles)
| No. | STRUCTURE | Molecular Ion [M + H]+ |
|---|---|---|
| 317 | 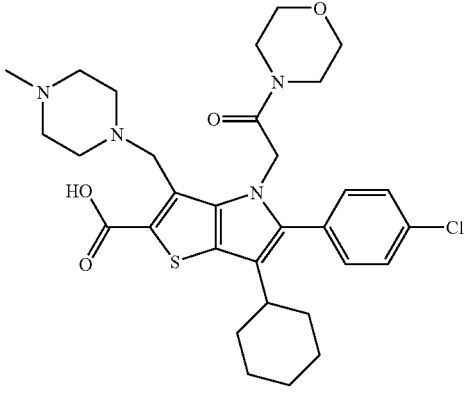 | 599, 601 |
| 318 | 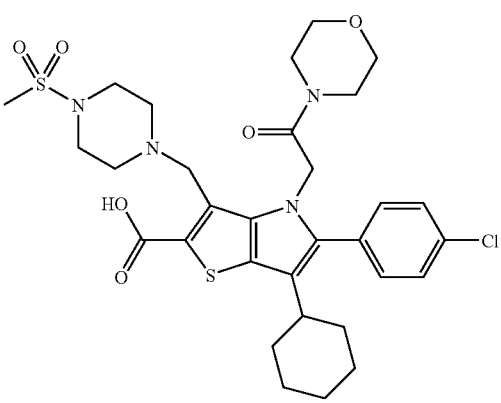 | 663, 665 |
| 319 | 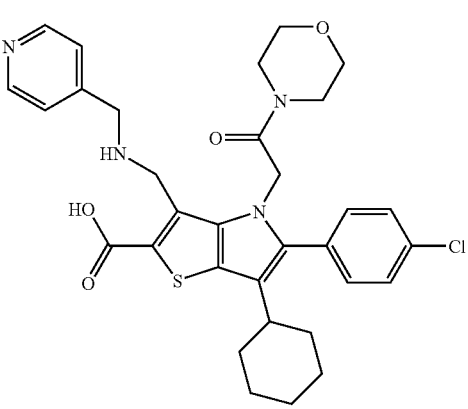 | 607, 607 |

TABLE 3-continued
Additional Examples (C-3, N-Disubstituted thieno[3,2-b]pyrroles)
| No. | STRUCTURE | Molecular Ion [M + H]+ |
|---|---|---|
| 320 | 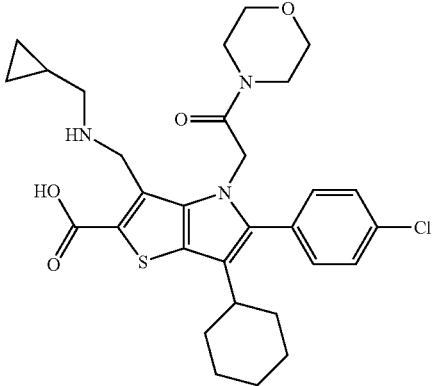 | 570, 572 |
| 321 | 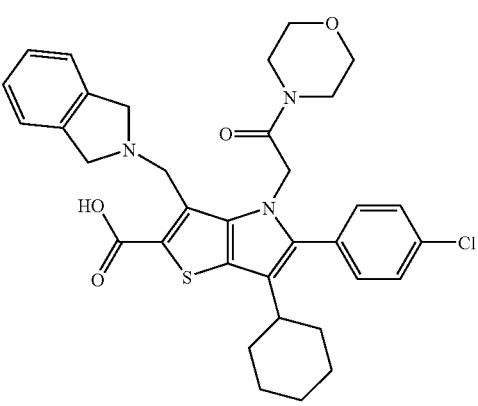 | 618, 620 |
| 322 | 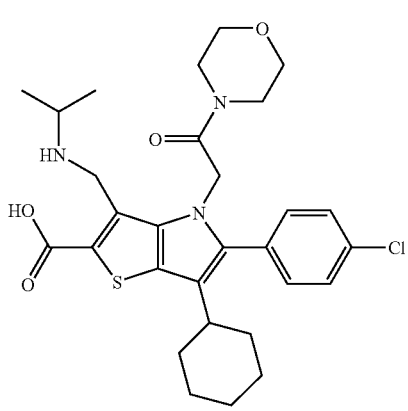 | 558, 560 |

TABLE 3-continued

Additional Examples (C-3, N-Disubstituted thieno[3,2-b]pyrroles)

| No. | STRUCTURE | Molecular Ion [M + H]+ |
|---|---|---|
| 323 | 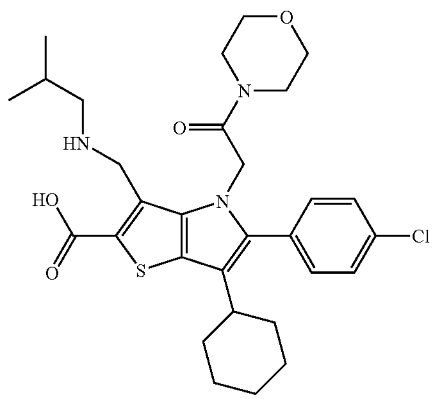 | 572, 574 |

TABLE 4

Additional Examples (N-Substituted thieno[2,3-b]pyrroles)

| No. | STRUCTURE | Molecular Ion [M + H]+ |
|---|---|---|
| 401 | 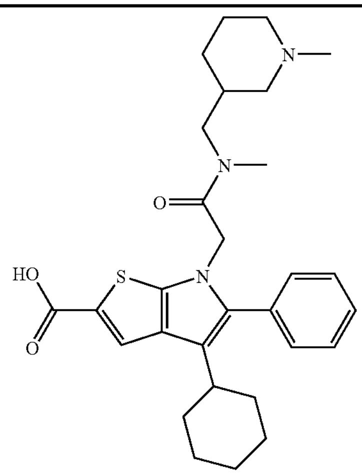 | 509 |

The invention claimed is:

1. A compound of the formula (I) or a pharmaceutically acceptable salt thereof:

(I)

wherein:
A is C—$C_tH_{2t}X^2$ and the dotted line indicates a bond that commences at C—$C_tH_{2t}X^2$;

B is S;
Y is cyclopentyl or cyclohexyl;
Ar is a moiety selected from the group consisting of phenyl, fluorophenyl, chlorophenyl, hydroxyphenyl, trifluoromethylphenyl, methoxyphenyl, difluorophenyl, methylphenyl, benzyloxyphenyl, formylphenyl, methoxychlorophenyl, dimethylaminomethylphenyl, dimethylaminoethoxyphenyl, pyridyl, furyl, oxazolyl, and thienyl;
n is 0, 1 or 2;
t is 0, 1 or 2;
Z is a C(O)OR$^{10}$ or CONR$^{10}$R$^{11}$ group where R$^{10}$ is hydrogen or $C_{1-6}$ alkyl and R$^{11}$ is hydrogen, $C_{1-6}$ alkyl or $S(O)_2C_{1-6}$alkyl;
X$^1$ is selected from hydrogen, methoxy, $C_{1-6}$alkyl, $C_{1-6}$alkyl$C_{1-6}$alkoxy, carboxy, C(OH)HCH$_2$NH($C_{1-6}$ alkyl); or (i) a moiety containing at least one aromatic ring and possesses 5-, 6-, 8-, 9- or 10-ring atoms up to 4 of which may be selected from O, N or S of which not more than one may be O or S and when N is present may be a N-oxide thereof; which ring may be substituted by $C_{1-6}$alkyl, $C_{4-10}$aryl, $C_{4-10}$aryl$C_{1-6}$alkyl, fluorine or chlorine; (ii) a non-aromatic ring of 3 to 8 ring atoms up to 4 of which may be selected from O, NH or S and which ring may be substituted by one or more groups selected from $C_{1-6}$alkyl, $C_{2-6}$alkenyl, $C_{1-6}$alkoxy, oxo, hydroxy or tautomers thereof; (iii) CONR$^4$R$^5$; or (iv) NR$^6$R$^7$;
X$^2$ is selected from hydrogen, hydroxyl and NR$^6$R$^7$;
R$^4$ is hydrogen or methyl;
R$^5$ is hydrogen, methyl, N-oxidepyrid-4-ylmethyl, 1-methylpiperidin-3-ylmethyl or 1-methylpiperidin-4-yl;
or R$^4$ and R$^5$ are joined to form a ring selected from 4-methylpiperazin-1-yl, morpholinyl, 4-pyrrolidinyl-piperazin-1-yl, dimethylaminomethyl-2-morpholin-4-yl or

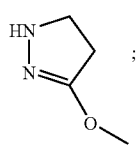
;

R[6] and R[7] are independently selected from hydrogen, C$_{1-6}$alkyl, —CO-phenyl, —SO$_2$N(C$_{1-6}$alkyl)$_2$, —(CO)$_2$N(C$_{1-6}$alky)$_2$, or methyl substituted by a ring selected from cyclopropyl, phenyl, pyrid-2-yl, pyrid-4-yl, N-oxide pyrid-4-yl, 5-methyl-1,2,4-triazo-3-yl,

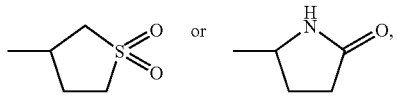

or R[6] and R[7] and the nitrogen atom to which they are attached form a morpholinyl, pyrrolidinyl, piperazinyl or isoindolinyl ring, which ring is optionally substituted by C$_{1-4}$alkyl or S(O)$_2$C$_{1-4}$alkyl.

2. The compound as claimed in claim 1 selected from:

6-cyclohexyl-5-phenyl-4H-thieno[3,2-b]pyrrole-2-carboxylic acid;

6-cyclohexyl-4-[2-(dimethylamino)-2-oxoethy]-5-phenyl-4H-thieno[3,2-b ]pyrrole-2-carboxylic acid;

6-cyclohexyl-1-4-(2-morpholin-4-yl-2-oxoethyl)-5-phenyl-4H-thieno[3,2-b ]pyrrole-2-carboxylic acid;

3-{[[(2-carboxy-6-cyclohexyl-5-phenyl-4H-thieno[3,2-b]pyrrol-4-yl)acetyl](methy)amino]methyl}-1-methylpiperidinium trifluoroacetate;

4-benzyl-6-cyclohexyl-5-phenyl-4H-thieno[3,2-b]pyrrole-2-carboxylic acid;

3-[(2-carboxy-6-cyclohexyl-5-phenyl-4H-thieno[3,2-b]pyrrol-4-yl)ethyl]pyridinium trifluoroacetate;

1-[2-(2-carboxy-6-cyclohexy1-5-phenyl-4H-thieno[3,2-b]pyrrol-4-yl)ethyl]pyrrolidinium trifluoroacetate;

6-cyclohexyl-4-methyl-5-phenyl-4H-thieno[3,2-b]pyrrole-2-carboxylic acid;

6-cyclopentyl-5-phenyl-4H-thieno[3,2-b]pyrrole-2-carboxylic acid;

[2-carboxy-6-cyclohexyl-4-(methoxymethyl)-5-phenyl-4H-thieno[3,2-b]pyrrol-3-yl]-N-[(1,1-dioxidotetrahydro-3-thienyl)methyl]methanaminium trifluoroacetate;

3-[(benzylamino)methyl]-6-cyclohexyl-4-(methoxymethyl)-5-phenyl-4H-thieno[3,2-b]pyrrole-2-carboxylic acid;

6-cyclohexyl-3-[(dimethylamino)methyl]-5-phenyl-4H-thieno[3,2-b]pyrrole-2-carboxylic acid;

5-(4-chlorophenyl)-6-cyclohexyl-4H-thieno[3,2-b]pyrrole-2-carboxylic acid;

5-(4-chlorophenyl)-6-cyclohexyl-4-[2-(dimethylamino)-2-oxoethyl]-4H-thieno[3,2-b]pyrrole-2-carboxylic acid;

methyl 5-(4-chlorophenyl)-6-cyclohexyl-4-(2-morpholin-4-yl-2-oxoethyl)-4H-thieno[3,2-b]pyrrole-2-carboxylate;

5-(4-chlorophenyl)-6-cyclohexyl-4-(2-morpholin-4-yl-2-oxoethyl)-4H-thieno[3,2-b]pyrrole-2-carboxylic acid;

5-(4-chlorophenyl)-6-cyclohexyl-N-methyl-4-(2-morpholin-4-yl-2-oxoethyl)-4H-thieno[3,2-b]pyrrole-2-carboxamide;

5-(4-chlorophenyl)-6-cyclohexyl-N-(ethylsulfonyl)-4-(2-morpholin-4-yl-2-oxoethyl)-4H-thieno[3,2-b]pyrrole-2-carboxamide;

6-cyclohexyl-4-methyl-5-(1,3-oxazol-5-yl)-4H-thieno[3,2-b]pyrrole-2-carboxylic acid;

5-(4-chlorophenyl)-6-cyclohexy1-4-(2-{2-[(dimethylamino)methyl]morpholinyl-4-yl}2-oxoethyl)-4H-thieno[3,2-b]pyrrole-2-carboxylic acid;

5-(4-chlorophenyl)-6-cyclohexyl-4-{2-[methyl(1-methylpiperidin-4-yl)amino]-2-oxoethyl}-4H-thieno[3,2-b]pyrrole-2-carboxylic acid;

5-(4-chlorophenyl)-6-cyclohexyl-4-(2-{methyl[(1-methylpiperidin-3-yl)methyl]amino}-2-oxoethyl)-4H-thieno[3,2-b]pyrrole-2-carboxylic acid;

5-(4-chlorophenyl)-6-cyclohexyl-4-methyl-4H-thieno[3,2-b]pyrrole-2-carboxylic acid;

5-(3-chlorophenyl)-6-cyclohexyl-4-(2-morpholin-4-yl-2-oxoethyl)-4H-thieno[3,2-b]pyrrole-2-carboxylic acid;

5-(3-chlorophenyl)-6-cyclohexyl-4-[2-(dimethylamino)-2-oxoethyl]-4H-thieno[3,2-b]pyrrole-2-carboxylic acid;

6-cyclohexyl-5-(4-methoxyphenyl)-4-(2-morpholin-4-yl-2-oxoethyl)-4H-thieno[3,2-b]pyrrole-2-carboxylic acid;

5-[4-(benzyloxy)phenyl]-6-cyclohexyl-4-(2-morpholin-4-yl-2-oxoethyl)-4H-thieno[3,2-b]pyrrole-2-carboxylic acid;

6-cyclohexyl-5-(4-methylphenyl)-4-(2-morpholin-4-yl-2-oxoethyl)-4H-thieno[3,2-b]pyrrole-2-carboxylic acid;

6-cyclohexyl-5-(4-formylphenyl)-4-(2-morpholin-4-yl-2-oxoethyl)-4H-thieno[3,2-b]pyrrole-2-carboxylic acid;

5-(3-chloro-4-methoxyphenyl)-6-cyclohexyl-4-(2-morpholin-4-yl-2-oxoethyl)-4H-thieno[3,2-b]pyrrole-2-carboxylic acid;

6-cyclohexyl-4-[2-(dimethylamino)-2-oxoethyl]-5-(4-formylphenyl)-4H-thieno[3,2-b]pyrrole-2-carboxylic acid;

6-cyclohexyl-4-[2-(dimethylamino)-2-oxoethyl]-5-(3-formylphenyl)-4H-thieno[3,2-b]pyrrole-2-carboxylic acid;

6-cyclohexyl-5-{3-[(dimethylamino)methyl]phenyl}-4-[2-(dimethylamino)-2-oxoethyl]-4H-thieno[3,2-b]pyrrole-2-carboxylic acid;

6-cyclohexyl-4-[2-(dimethylamino)-2-oxoethyl]-5-(3-furyl)-4H-thieno[3,2-b]pyrrole-2-carboxylic acid;

6-cyclohexyl-5-{4-[2-(dimethylamino)ethoxy]phenyl}-4-[2-(dimethylamino)-2-oxoethyl]-4H-thieno[3,2-b]pyrrole-2-carboxylic acid;

6-cyclohexyl-4-[2-(dimethylamino)-2-oxoethyl]-5-(3-methoxyphenyl)-4H-thieno[3,2-b]pyrrole-2-carboxylic acid;

3-{[benzyl(methyl)amino]methyl}-6-cyclohexyl-4-(methoxymethyl)-5-phenyl-4H-thieno[3,2-b]pyrrole-2-carboxylic acid;

5-(4-chlorophenyl)-6-cyclohexyl-4-methyl-3-(pyrrolidin-1-ylmethyl)-4H-thieno[3,2-b]pyrrole-2-carboxylic acid;

5-(4-chlorophenyl)-6-cyclohexyl-4-methyl-3-[(4-methylpiperazin-1-yl)methyl]-4H-thieno[3,2-b]pyrrole-2-carboxylic acid;

5-(4-chlorophenyl)-6-cyclohexyl-3-(1,3-dihydro-2H-isoindol-2-ylmethyl)-4-methyl-4H-thieno[3,2-b]pyrrole-2-carboxylic acid;

5-(4-chlorophenyl)-6-cyclohexyl-4-methyl-3-{[4-(methylsulfonyl)piperazin-1-yl]methyl}-4H-thieno[3,2-b]pyrrole-2-carboxylic acid;

5-(4-chlorophenyl)-6-cyclohexyl-4-methyl-3-{[(pyridin-4-ylmethyl)amino]methyl}-4H-thieno[3,2-b]pyrrole-2-carboxylic acid;

5-(4-chlorophenyl)-6-cyclohexyl-3-[(dimethylamino)methyl]-4-methyl-4H-thieno[3,2-b]pyrrole-2-carboxylic acid;

5-(4-chlorophenyl)-6-cyclohexyl-3-[(dimethylamino)methyl]-4-(2-morpholin-4-yl-2-oxoethyl)-4H-thieno[3,2-b]pyrrole-2-carboxylic acid;

5-(4-chlorophenyl)-6-cyclohexyl-4-(2-morpholin-4-yl-2-oxoethyl)-3-(pyrrolidin-1-ylmethyl)-4H-thieno[3,2-b]pyrrole-2-carboxylic acid;

5-(4-chlorophenyl)-6-cyclohexyl-3-[(4-methylpiperazin-1-yl)methyl]-4-(2-morpholin-4-yl-2-oxoethyl)-4H-thieno[3,2-b]pyrrole-2-carboxylic acid;

5-(4-chlorophenyl)-6-cyclohexyl-3-{[4-(methylsulfonyl)piperazin-1-yl]methyl}-4-(2-morpholin-4-yl-2-oxoethyl)-4H-thieno[3,2-b]pyrrole-2-carboxylic acid;

5-(4-chlorophenyl)-6-cyclohexyl-4-(2-morpholin-4-yl-2-oxoethyl)-3-{[(pyridin-4-ylmethyl)amino]methyl}-4H-thieno[3,2-b]pyrrole-2-carboxylic acid;

5-(4-chlorophenyl)-6-cyclohexyl-3-{[(cyclopropylmethyl)amino]methyl }-4-(2-morpholin-4-yl-2-oxoethyl)-4H-thieno[3,2-b]pyrrole-2-carboxylic acid;

5-(4-chlorophenyl)-6-cyclohexyl-3-(1,3-dihydro-2H-isoindol-2-ylmethyl)-4-(2-morpholin-4-yl-2-oxoethyl)-4H-thieno[3,2-b]pyrrole-2-carboxylic acid;

5-(4-chlorophenyl)-6-cyclohexyl-3-[(isopropylamino)methyl]-4-(2-morpholin-4-yl-2-oxoethyl)-4H-thieno[3,2-b]pyrrole-2-carboxylic acid; and 5-(4-chlorophenyl)-6-cyclohexyl-3-[(isobutylamino)methyl]-4-(2-morpholin-4-yl-2-oxoethyl)-4H-thieno[3,2-b]pyrrole-2-carboxylic acid;

or a pharmaceutically acceptable salt thereof.

3. A pharmaceutical composition comprising a compound as claimed in claim 1 or a pharmaceutically acceptable salt thereof together with a pharmaceutically acceptable carrier.

4. The pharmaceutical composition as claimed in claim 3, which further comprises one or more agents for the treatment of a viral infection.

5. A method of inhibiting hepatitis C virus polymerase and/or of treating a hepatitis C viral infection, which comprises administering to a human or animal subject suffering from the infection a therapeutically effective amount of a compound as claimed in claim 1, or a pharmaceutically acceptable salt thereof.

6. A method of preparation of a pharmaceutical composition, which comprises admixing at least one compound as claimed in claim 1, or a pharmaceutically acceptable salt thereof, with one or more pharmaceutically acceptable adjuvants, diluents or carriers and/or with one or more therapeutically active agents.

7. A process for the preparation of a compound as claimed in claim 1 which comprises the reaction of a compound of formula (IV) with a compound of formula (V):

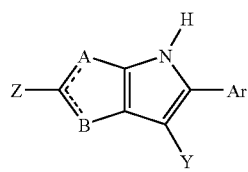

(IV)

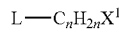

(V)

wherein A, B, Z, Ar, $X^1$, n and Y are as defined in claim 1 and L is a leaving group.

8. A method for inhibiting hepatitis C virus polymerase or treating a hepatitis C viral infection, which comprises administering to a human or animal subject suffering from the infection a therapeutically effective amount of the pharmaceutical composition of claim 3.

* * * * *